(12) United States Patent
Constantin et al.

(10) Patent No.: US 11,766,194 B2
(45) Date of Patent: Sep. 26, 2023

(54) SYSTEM AND METHOD FOR DECISION SUPPORT

(71) Applicant: DexCom, Inc., San Diego, CA (US)

(72) Inventors: Alexandra Elena Constantin, San Diego, CA (US); Scott M. Belliveau, San Diego, CA (US); Naresh C. Bhavaraju, San Diego, CA (US); Jennifer Blackwell, San Diego, CA (US); Eric Cohen, San Diego, CA (US); Basab Dattaray, San Diego, CA (US); Anna Leigh Davis, San Diego, CA (US); Rian Draeger, San Diego, CA (US); Arturo Garcia, San Diego, CA (US); John Michael Gray, San Diego, CA (US); Hari Hampapuram, San Diego, CA (US); Nathaniel David Heintzman, San Diego, CA (US); Lauren Hruby Jepson, San Diego, CA (US); Matthew Lawrence Johnson, San Diego, CA (US); Apurv Ullas Kamath, San Diego, CA (US); Katherine Yerre Koehler, San Diego, CA (US); Phil Mayou, San Diego, CA (US); Patrick Wile McBride, San Diego, CA (US); Michael Robert Mensinger, San Diego, CA (US); Sumitaka Mikami, San Diego, CA (US); Andrew Attila Pal, San Diego, CA (US); Nicholas Polytaridis, San Diego, CA (US); Philip Thomas Pupa, San Diego, CA (US); Eli Reihman, San Diego, CA (US); Peter C. Simpson, San Diego, CA (US); Tomas C. Walker, San Diego, CA (US); Daniel Justin Wiedeback, San Diego, CA (US); Subrai Girish Pai, San Diego, CA (US); Matthew T. Vogel, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 109 days.

(21) Appl. No.: 16/269,480

(22) Filed: Feb. 6, 2019

(65) Prior Publication Data

US 2019/0246973 A1 Aug. 15, 2019

Related U.S. Application Data

(60) Provisional application No. 62/628,895, filed on Feb. 9, 2018.

(51) Int. Cl.
*A61B 5/145* (2006.01)
*G16H 70/20* (2018.01)
(Continued)

(52) U.S. Cl.
CPC ........ *A61B 5/14532* (2013.01); *A61B 5/0022* (2013.01); *A61B 5/01* (2013.01);
(Continued)

(58) Field of Classification Search
CPC ..... A61B 5/0024; A61B 5/01; A61B 5/02055; A61B 5/0022; A61B 5/024; A61B 5/0816;
(Continued)

(56) References Cited

U.S. PATENT DOCUMENTS 6,001,067 A 12/1999 Shults et al.
6,424,847 B1 7/2002 Mastrototaro et al.
(Continued)

FOREIGN PATENT DOCUMENTS

JP 2012200271 A 10/2012
JP 2017515520 A 6/2017
(Continued)

OTHER PUBLICATIONS

Cernazanu-Glavan C., et al., "DeeDee—a mobile Intelligent System able to Assist a Type 1 Diabetic Through the Daily Life", 2014 IEEE 9th International Symposium on Applied Computational Intelligence and Informatics (SACI), IEEE., May 15, 2014, 5 pages.
(Continued)

*Primary Examiner* — Patrick Fernandes
*Assistant Examiner* — Anna Roberts
(74) *Attorney, Agent, or Firm* — PATTERSON + SHERIDAN, LLP

(57) ABSTRACT

Systems and methods are provided to provide guidance to a user regarding management of a physiologic condition such
(Continued)

as diabetes. The determination may be based upon a patient glucose concentration level. The glucose concentration level may be provided to a stored model to determine a state. The guidance may be determined based at least in part on the determined state.

22 Claims, 49 Drawing Sheets

(51) Int. Cl.
| | |
|---|---|
| A61B 5/00 | (2006.01) |
| G06N 20/00 | (2019.01) |
| G06N 5/045 | (2023.01) |
| A61B 5/11 | (2006.01) |
| A61B 5/01 | (2006.01) |
| A61B 5/0205 | (2006.01) |
| G16H 50/20 | (2018.01) |
| A61B 5/024 | (2006.01) |
| A61B 5/08 | (2006.01) |

(52) U.S. Cl.
CPC ........ *A61B 5/02055* (2013.01); *A61B 5/1118* (2013.01); *A61B 5/486* (2013.01); *A61B 5/4839* (2013.01); *A61B 5/4866* (2013.01); *A61B 5/7221* (2013.01); *A61B 5/7275* (2013.01); *A61B 5/7282* (2013.01); *A61B 5/746* (2013.01); *A61B 5/7475* (2013.01); *G06N 5/045* (2013.01); *G06N 20/00* (2019.01); *G16H 70/20* (2018.01); *A61B 5/024* (2013.01); *A61B 5/0816* (2013.01); *G16H 50/20* (2018.01)

(58) Field of Classification Search
CPC ..... A61B 5/1118; A61B 5/4839; A61B 5/486; A61B 5/4866; A61B 5/7275; A61B 5/7221; A61B 5/7282; A61B 5/7435; A61B 5/7475; A61B 5/746; A61B 5/14532; A61B 2560/0242; A61B 2562/0219; G06N 5/045; G06N 20/00; G16H 20/17; G16H 40/67; G16H 50/20; G16H 50/50; G16H 70/20
See application file for complete search history.

(56) References Cited

U.S. PATENT DOCUMENTS

| | | | |
|---|---|---|---|
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,653,930 B1 | 11/2003 | Bonomo et al. | |
| 6,923,763 B1 | 8/2005 | Kovatchev et al. | |
| 7,022,072 B2 | 4/2006 | Fox et al. | |
| 7,025,425 B2 | 4/2006 | Kovatchev et al. | |
| 7,052,472 B1 | 5/2006 | Miller et al. | |
| 7,137,951 B2 | 11/2006 | Pilarski | |
| 7,261,691 B1 | 8/2007 | Asomani | |
| 7,344,251 B2 | 3/2008 | Marshall | |
| 7,384,396 B2 | 6/2008 | Samuels et al. | |
| 7,438,418 B2 | 10/2008 | Marshall | |
| 7,591,801 B2 | 9/2009 | Brauker et al. | |
| 7,727,147 B1 | 6/2010 | Osorio et al. | |
| 7,768,386 B2 | 8/2010 | Hayter et al. | |
| 7,828,728 B2 | 11/2010 | Boock et al. | |
| 7,874,985 B2 | 1/2011 | Kovatchev et al. | |
| 7,905,832 B1 | 3/2011 | Lau et al. | |
| 7,988,630 B1 | 8/2011 | Osorio et al. | |
| 8,226,556 B2 | 7/2012 | Hayes et al. | |
| 8,269,634 B2 | 9/2012 | Fischell et al. | |
| 8,290,562 B2 | 10/2012 | Goode, Jr. et al. | |
| 8,301,231 B2 | 10/2012 | Fischell et al. | |
| 8,514,086 B2 | 8/2013 | Harper et al. | |
| 8,538,703 B2 | 9/2013 | Kovatchev et al. | |
| 8,548,544 B2 | 10/2013 | Kircher et al. | |
| 8,562,587 B2 | 10/2013 | Kovatchev et al. | |
| 8,585,593 B2 | 11/2013 | Kovatchev et al. | |
| 8,589,082 B2 | 11/2013 | Chakrabarty et al. | |
| 8,798,934 B2 | 8/2014 | Wei et al. | |
| 8,808,228 B2 | 8/2014 | Brister et al. | |
| 8,884,767 B2 | 11/2014 | Kidmore | |
| 8,922,352 B2 | 12/2014 | Tsui et al. | |
| 8,930,222 B2 | 1/2015 | Rhine-Pallas et al. | |
| 8,930,290 B2 | 1/2015 | Cragun et al. | |
| 8,954,373 B2 | 2/2015 | Atlas et al. | |
| 8,974,385 B2 | 3/2015 | Lee et al. | |
| 8,974,746 B2 | 3/2015 | Matsumura | |
| 8,992,475 B2 | 3/2015 | Mann et al. | |
| 9,041,730 B2 | 5/2015 | Johnson et al. | |
| 9,076,317 B2 | 7/2015 | Nothacker et al. | |
| 9,092,555 B2 * | 7/2015 | Gunaratnam | G16H 40/67 |
| 9,119,528 B2 | 9/2015 | Cobelli et al. | |
| 9,135,402 B2 | 9/2015 | Mensinger et al. | |
| 9,330,237 B2 | 5/2016 | Cohen et al. | |
| 9,386,522 B2 | 7/2016 | San Vicente et al. | |
| 9,398,869 B2 | 7/2016 | Kovatchev et al. | |
| 9,430,022 B2 | 8/2016 | Kovachev et al. | |
| 9,439,602 B2 | 9/2016 | Sparacino et al. | |
| 9,446,194 B2 | 9/2016 | Kamath et al. | |
| 9,579,456 B2 | 2/2017 | Budiman et al. | |
| 9,622,691 B2 | 4/2017 | Budiman | |
| 9,730,621 B2 | 8/2017 | Cohen et al. | |
| 9,885,698 B2 | 2/2018 | Islam | |
| 9,974,903 B1 | 5/2018 | Davis et al. | |
| 9,980,671 B2 | 5/2018 | Refvik | |
| 10,052,073 B2 | 8/2018 | Davis et al. | |
| 10,328,204 B2 | 6/2019 | Davis et al. | |
| 10,406,287 B2 | 9/2019 | Davis et al. | |
| 10,748,658 B2 * | 8/2020 | McRaith | G16H 10/60 |
| 2001/0047125 A1 | 11/2001 | Quy | |
| 2003/0125612 A1 | 7/2003 | Fox et al. | |
| 2003/0191376 A1 | 10/2003 | Samuels et al. | |
| 2003/0195404 A1 | 10/2003 | Knobbe et al. | |
| 2005/0027182 A1 | 2/2005 | Siddiqi et al. | |
| 2005/0228245 A1 | 10/2005 | Quy | |
| 2006/0020187 A1 | 1/2006 | Brister et al. | |
| 2006/0203197 A1 | 9/2006 | Marshall | |
| 2007/0027385 A1 | 2/2007 | Brister et al. | |
| 2007/0213657 A1 * | 9/2007 | Jennewine | A61B 5/4839 |
| | | | 604/66 |
| 2007/0291232 A1 | 12/2007 | Marshall | |
| 2008/0071157 A1 | 3/2008 | McGarraugh et al. | |
| 2008/0119703 A1 | 5/2008 | Brister et al. | |
| 2008/0154513 A1 | 6/2008 | Kovatchev et al. | |
| 2008/0220403 A1 | 9/2008 | Marling et al. | |
| 2009/0033482 A1 | 2/2009 | Hayter et al. | |
| 2009/0082692 A1 | 3/2009 | Hale et al. | |
| 2009/0137887 A1 | 5/2009 | Brister et al. | |
| 2009/0143725 A1 | 6/2009 | Peyser et al. | |
| 2009/0163793 A1 | 6/2009 | Koehler et al. | |
| 2009/0171589 A1 | 7/2009 | Kovatchev | |
| 2009/0192366 A1 | 7/2009 | Mensinger et al. | |
| 2009/0234213 A1 | 9/2009 | Hayes et al. | |
| 2010/0138203 A1 | 6/2010 | Alferness et al. | |
| 2010/0145174 A1 | 6/2010 | Alferness et al. | |
| 2010/0161236 A1 | 6/2010 | Cohen et al. | |
| 2010/0174553 A1 | 7/2010 | Kaufman et al. | |
| 2010/0179768 A1 | 7/2010 | Kovatchev et al. | |
| 2010/0198520 A1 | 8/2010 | Breton et al. | |
| 2010/0214104 A1 | 8/2010 | Goode, Jr. et al. | |
| 2010/0222648 A1 | 9/2010 | Tan | |
| 2010/0249561 A1 | 9/2010 | Patek et al. | |
| 2010/0261987 A1 | 10/2010 | Kamath et al. | |
| 2010/0292634 A1 | 11/2010 | Kircher et al. | |
| 2010/0302042 A1 | 12/2010 | Barnett et al. | |
| 2010/0317952 A1 | 12/2010 | Budiman et al. | |
| 2010/0324932 A1 | 12/2010 | Galley et al. | |
| 2011/0021898 A1 | 1/2011 | Wei et al. | |
| 2011/0027127 A1 | 2/2011 | Simpson et al. | |

(56) References Cited

U.S. PATENT DOCUMENTS

| | | |
|---|---|---|
| 2011/0054264 A1 | 3/2011 | Fischell et al. |
| 2011/0054334 A1 | 3/2011 | Fischell et al. |
| 2011/0071365 A1 | 3/2011 | Lee et al. |
| 2011/0098548 A1* | 4/2011 | Budiman ............... G06F 19/00 600/365 |
| 2011/0118578 A1 | 5/2011 | Timmerman |
| 2011/0193704 A1 | 8/2011 | Harper et al. |
| 2011/0201911 A1 | 8/2011 | Johnson et al. |
| 2012/0004512 A1 | 1/2012 | Kovatchev et al. |
| 2012/0078067 A1 | 3/2012 | Kovatchev et al. |
| 2012/0123234 A1 | 5/2012 | Atlas et al. |
| 2012/0231431 A1 | 9/2012 | Angelides |
| 2012/0235820 A1 | 9/2012 | Kidmose |
| 2012/0245556 A1 | 9/2012 | Kovatchev et al. |
| 2013/0011819 A1 | 1/2013 | Horseman |
| 2013/0035563 A1 | 2/2013 | Angelides |
| 2013/0035871 A1 | 2/2013 | Mayou et al. |
| 2013/0072765 A1 | 3/2013 | Kahn et al. |
| 2013/0076531 A1 | 3/2013 | San Vicente et al. |
| 2013/0109944 A1 | 5/2013 | Sparacino et al. |
| 2013/0116649 A1 | 5/2013 | Breton et al. |
| 2013/0184548 A1 | 7/2013 | Matsumura |
| 2013/0282302 A1 | 10/2013 | Harper |
| 2013/0307636 A1 | 11/2013 | Kimbara et al. |
| 2013/0307686 A1 | 11/2013 | Frauenthal et al. |
| 2013/0325352 A1 | 12/2013 | Greene et al. |
| 2014/0006322 A1 | 1/2014 | Cragun et al. |
| 2014/0012510 A1 | 1/2014 | Mensinger et al. |
| 2014/0031786 A1 | 1/2014 | Kircher et al. |
| 2014/0039383 A1 | 2/2014 | Dobbles et al. |
| 2014/0046159 A1 | 2/2014 | Kovatchev et al. |
| 2014/0066889 A1 | 3/2014 | Grosman et al. |
| 2014/0088393 A1 | 3/2014 | Bernstein et al. |
| 2014/0107449 A1 | 4/2014 | Ecoff et al. |
| 2014/0118138 A1 | 5/2014 | Cobelli et al. |
| 2014/0118166 A1 | 5/2014 | Hampapuram et al. |
| 2014/0121488 A1 | 5/2014 | Budiman |
| 2014/0128803 A1 | 5/2014 | Dobbles et al. |
| 2014/0184422 A1 | 7/2014 | Mensinger et al. |
| 2014/0188398 A1 | 7/2014 | Cohen et al. |
| 2014/0200426 A1 | 7/2014 | Taub et al. |
| 2014/0200559 A1 | 7/2014 | Doyle, III et al. |
| 2014/0243637 A1 | 8/2014 | Rahman et al. |
| 2014/0253323 A1 | 9/2014 | Berven |
| 2014/0276238 A1 | 9/2014 | Osorio |
| 2014/0288494 A1 | 9/2014 | Brister et al. |
| 2014/0324800 A1 | 10/2014 | Soni et al. |
| 2014/0361900 A1 | 12/2014 | Nothacker et al. |
| 2014/0371816 A1 | 12/2014 | Matos |
| 2014/0379273 A1 | 12/2014 | Petisce et al. |
| 2014/0380218 A1 | 12/2014 | Johnnie |
| 2015/0018633 A1 | 1/2015 | Kovachev et al. |
| 2015/0045632 A1 | 2/2015 | Bagan |
| 2015/0061890 A1 | 3/2015 | Rees et al. |
| 2015/0118658 A1 | 4/2015 | Mayou et al. |
| 2015/0118668 A1 | 4/2015 | Mayou et al. |
| 2015/0119655 A1 | 4/2015 | Mayou et al. |
| 2015/0119667 A1 | 4/2015 | Roihman et al. |
| 2015/0119668 A1 | 4/2015 | Mayou et al. |
| 2015/0120317 A1 | 4/2015 | Mayou et al. |
| 2015/0123810 A1 | 5/2015 | Hernandez-Rosas et al. |
| 2015/0134356 A1 | 5/2015 | Atlas et al. |
| 2015/0164390 A1 | 6/2015 | Larvenz et al. |
| 2015/0190098 A1 | 7/2015 | Patek et al. |
| 2015/0190100 A1 | 7/2015 | Fox et al. |
| 2015/0208975 A1 | 7/2015 | Ghajar |
| 2015/0227710 A1 | 8/2015 | Pappada |
| 2015/0250429 A1 | 9/2015 | Hampapuram et al. |
| 2015/0282767 A1 | 10/2015 | Stivoric et al. |
| 2015/0285759 A1 | 10/2015 | Javitt et al. |
| 2015/0289821 A1 | 10/2015 | Rack-Gomer et al. |
| 2015/0289823 A1 | 10/2015 | Rack-Gomer et al. |
| 2015/0305658 A1 | 10/2015 | Islam |
| 2015/0324520 A1 | 11/2015 | Aykroyd et al. |
| 2016/0004813 A1 | 1/2016 | Kovatchev et al. |
| 2016/0081597 A1 | 3/2016 | Bhavaraju et al. |
| 2016/0171183 A1 | 6/2016 | Breton et al. |
| 2016/0174911 A1 | 6/2016 | Palerm et al. |
| 2016/0213290 A1 | 7/2016 | Park et al. |
| 2016/0328527 A1 | 11/2016 | Christensen et al. |
| 2016/0328991 A1 | 11/2016 | Simpson et al. |
| 2016/0331310 A1 | 11/2016 | Kovatchev et al. |
| 2017/0049386 A1 | 2/2017 | Abraham et al. |
| 2017/0056591 A1 | 3/2017 | Breton et al. |
| 2017/0105104 A1* | 4/2017 | Ulmansky ............... H04W 4/42 |
| 2017/0132120 A1 | 5/2017 | Salameh et al. |
| 2017/0147769 A1 | 5/2017 | Bernstein et al. |
| 2017/0177825 A1 | 6/2017 | Wolpert |
| 2017/0185953 A1 | 6/2017 | Dalforno et al. |
| 2017/0203039 A1 | 7/2017 | Desborough et al. |
| 2017/0216518 A1 | 8/2017 | Davis et al. |
| 2017/0220750 A1 | 8/2017 | Davis et al. |
| 2017/0220751 A1 | 8/2017 | Davis et al. |
| 2017/0293732 A1 | 10/2017 | Cohen et al. |
| 2017/0311903 A1 | 11/2017 | Davis et al. |
| 2017/0311904 A1 | 11/2017 | Davis et al. |
| 2017/0316320 A1* | 11/2017 | Jamjoom ............. G06Q 10/109 |
| 2017/0329933 A1 | 11/2017 | Brust et al. |
| 2017/0347971 A1 | 12/2017 | Davis et al. |
| 2018/0060495 A1* | 3/2018 | Mahapatra ............. G16H 50/50 |
| 2018/0126074 A1 | 5/2018 | Davis et al. |
| 2018/0153410 A1 | 6/2018 | Islam |
| 2018/0174675 A1* | 6/2018 | Roy ....................... G16H 50/20 |
| 2018/0200437 A1 | 7/2018 | Mazlish et al. |
| 2018/0200438 A1* | 7/2018 | Mazlish ................ G16H 20/17 |
| 2018/0292377 A1 | 10/2018 | Islam |
| 2018/0326150 A1 | 11/2018 | Davis et al. |
| 2018/0353112 A1 | 12/2018 | Dassau et al. |
| 2019/0223791 A1 | 7/2019 | Sayani et al. |
| 2019/0246914 A1 | 8/2019 | Constantin et al. |
| 2019/0251456 A1 | 8/2019 | Constantin et al. |
| 2019/0252079 A1 | 8/2019 | Constantin et al. |
| 2019/0320976 A1 | 10/2019 | Roslin et al. |

FOREIGN PATENT DOCUMENTS

| | | |
|---|---|---|
| JP | 2017225602 A | 12/2017 |
| WO | WO 2005-082436 | 9/2005 |
| WO | WO 2007-149533 | 12/2007 |
| WO | WO 2008-101172 | 8/2008 |
| WO | WO 2009-048462 | 4/2009 |
| WO | WO 2010-111660 | 9/2010 |
| WO | WO 2012-175181 | 12/2012 |
| WO | WO 2014-011488 | 1/2014 |
| WO | WO 2015-026579 | 2/2015 |
| WO | WO 2015-056259 | 4/2015 |
| WO | WO 2015-066051 | 5/2015 |
| WO | 2015156965 A1 | 10/2015 |
| WO | WO-2015148313 A1 | 10/2015 |
| WO | WO 2015-187366 | 12/2015 |
| WO | WO 2016-025874 | 2/2016 |
| WO | WO-2016040927 A2 | 3/2016 |
| WO | WO 2016-133879 | 8/2016 |
| WO | WO 2016-201120 | 12/2016 |
| WO | WO 2017-040927 | 3/2017 |
| WO | WO 2017-132663 | 8/2017 |
| WO | WO 2018/031803 | 2/2018 |

OTHER PUBLICATIONS

Donsa K., et al., "Towards Personalization of Diabetes Therapy Using Computerized Decision Support and Machine Learning: Some Open Problems and Challenges", International Conference on Computer Analysis of Images and Patterns, CAIP 2017, Jan. 1, 2015, Springer, Heidelberg vol. 8700, pp. 237-260.

International Search Report and Written opinion for Application No. PCT/US2019/016922, dated Jul. 23, 2019, 13 pages.

Marling C. et al., "The 4 Diabetes Support System: a case study in CBR Research and Development", Sep. 12, 2011, International Conference on Computer Analysis of Images and Patterns, Computer Analysis of Images and Patterns, pp. 137-150.

(56) References Cited

OTHER PUBLICATIONS

Zarkogianni K., et al., "A Review of Emerging Technologies for the management of Diabetes Mellitus," IEEE Transactions on Biomedical Engineering, IEEE Service Center, Piscataway, NJ, USA, vol. 62(12), 17 pages.

Ambrosiadou et al. 1996. Computer Methods and Programs in Biomedicine 49:105-115. Clinical evaluation of the Diabetes expert system for decision support by multiple regimen.

Benharref et al. 2014. Conf Proc. IEEE Eng. Med. Biol. Soc. 2014:2698-1701. Closing the loop from continuous M-health monitoring to fuzzy logic-based optimized recommendatio.

Carlson et al. 2013. Association for the Advancement of Artificial Intelligence, the MITRE Corporation Innovation Program, Project 51MS661-CA (Approved for Public Release, Di.

Desai, Junjal 2012, University of Massachusetts Lowell Ph.D. Thesis, Modeling Trust to Improve Human-Robot Interaction. [225 pages].

Glorennec et al. 1995. Predictive Fuzzy Model of Glycaemic Variations, pp. 411-420 in Fuzzy Logic and Soft Computing.

Herrero et al. 2012. J. Diabetes Science and Technology 6(5):1131-1141. Robust Fault Detection System for Insulin Pump Therapy Using Continuous Glucose Monitoring.

Herrero et al. Apr. 2015. Computer Methods and Programs in Biomedicine 119(1):1-8. Method for automatic adjustment of an insulin bolus calculator: In silico robustness evalu.

Herrera et al. Apr. 2013. DOI 10.1109/JBHI.2014.2331896, IEEE Journal of Biomedical and Health Informatics. Advanced Insulin Bolus Advisor based on Run-to-Run Control and C.

Herrero et al. Feb. 2015 (pre-pubn). Comput. Methods Programs Biomed. (2015), http://dx.doi.org/10.1016/j.cmpb.2015.02.003. Method for automatic adjustment of an insulin bolu.

Herrero et al. Jun. 2014 (pre-pubn), Pubn May 2015. IEEE J. Biomed. and Health Inform. 19(3):1087-1096 (2015). Advanced Insulin Bolus Advisor based on Run-to-Run Control and.

Hsu et al. 2016 Diabetes Technology and Therapeutics 18:59-68. Utilization of a cloud-based diabetes management program for insulin initiation and titration enables collabo.

http://www.wired.com/2014/06/trust-robots-2/, Printed Mar. 4, 2015. You Should Learn to Trust your Robots. It's for Your Own Good.

Lee & See 2004. Human Factors 46(1):50-80. Trust in Automation: Designing for Appropriate Reliance.

Lee, John D. 2008. Human Factors 50(3):404-410. Review of Pivotal Human Factors Article: "Humans and Automation: Use, Misuse, Disuse, Abuse."

Parasumaman 1997. Human Factors 39(2):230-253. Humans and Automation: Use, Misuse, Disuse, Abuse.

Parasuraman et al. 2000. IEEE Transactions on Systems, Man and Cybernetics—Part A: Systems and Humans 30(3):286-297. A Model for Types and Levels of Human Interaction wit.

Pesl et al. 2015. IEEE J Biomedical and Health Informatics, DOI 10.1109/JBHI.2015.2464088. An Advanced Bolus Calculator for Type 1 Diabetes: System Architecture and Usabili.

Pesl et al. Aug. 2015 (pre-pubn). IEEE Journal of Biomedical and Health Informatics DOI 10.1109/JBHI.2015.2464088. An Advanced Bolus Calculator for Type 1 Diabetes: Syste.

Pesl et al. Feb. 2014. A Mobile-Based Advanced Bolus Calculator for Diabetes Management. (Poster) Imperiod Collegel London, UK.

Pesl et al. Jan. 2015. J. Diabetes Technology & Therapeutics 17:A129 (abstract & poster). Acceptability of a Patient and Clinical Platform of an Advanced Bolus Calculator for.

Pesl et al. Jan. 2016. IEEE Journal of Biomedical and Health Informatics 20(1):11-17, an Advanced Bolus Calculator for Type 1 Diabetes: System Architecture and Usability Res.

Reddy et al. 2015. Clinical Safety Evaluation of an Advanced Bolus Calculator for Type 1 Diabetes (ABC4D) (poster). Imperiod College of London, UK.

Reddy et al. Feb. 2015. J. Diabetes Technology & Therapeutics 17:A129-A130 (poster & abstract). Clinical Safety Evaluation of an Advanced Bolus Calculator for Type 1 Diabetes.

Scheiner 2015. Practical CGM: a Guide to Improving Outcomes through Continuous Glucose Monitoring. Chapter 2, pp. 17-34, American Diabetes Association, Inc., Alexandra, VA.

Schwartz et al. Nov. 2010. J. Diabetes Science & Technology 4(6):1563-1569. Evaluationg the automated blood glucose pattern detection and case-retrieval modules of the 4 dia.

Scott 2014, SMBG Bolus Calculator Design. Abbott Diabetes Care presentation.

Stadelmann et al. 1990. Computer Methods and Programs in Biomedicine 32:333-337. DIABETEX decision module 2—calculation of insulin dose proposals and situation recognition.

Walsh et al. 2014. J. Diabetes Science & Technology 8(1):170-178. Confuslon regarding duration of insulin action: a potential source for major insulin dose errors by bolus.

Office Action from European Patent Application No. 19751580.2, dated Sep. 16, 2020, 3 pages.

Contreras I., et al., "Artificial Intelligence for Diabetes Management and Decision Support: a Literature Review," Journal of Medical Internet Research May 2018, pp. 1-37.

Extended European Search Report for Application No. 19751580.2, dated Sep. 9, 2021, 7 pages.

Rajalakshmi K. et al., "Decision Support System in Healthcare Industry," International Journal of Computer Applications (0975-8887), vol. 26 (9), Jul. 2011, pp. 42-44.

\* cited by examiner

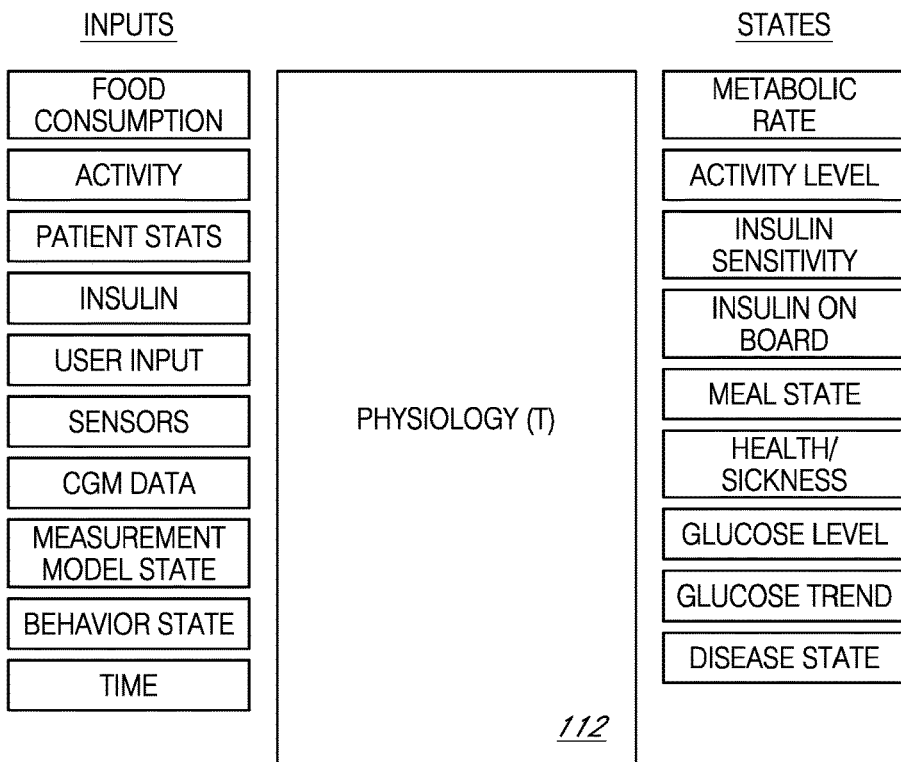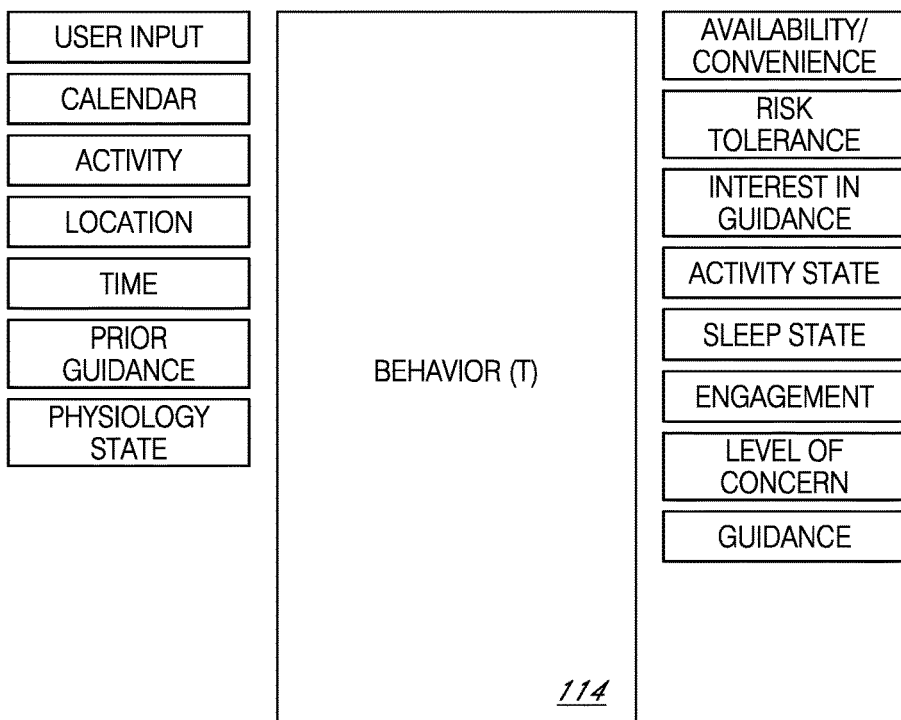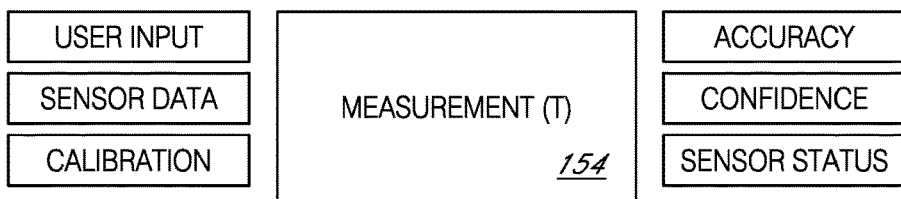
FIG. 2B

FIG. 3A

| ACTIVITY | MEAL | AVAILABLE | MEETING | AVAILABLE | MEETING |
|---|---|---|---|---|---|

| MEAL | AVAILABLE | DRIVING | AVAILABLE | DRIVING | NOT PRESENT | DRIVING | AVAILABLE |
|---|---|---|---|---|---|---|---|

| MEAL | AVAILABLE | RIDING | BASKETBALL GAME |
|---|---|---|---|

| MEAL | AVAILABLE | SLEEP | WAKE STATE | SLEEP | WAKE - MORNING |
|---|---|---|---|---|---|

| NOT AVAILABLE | AVAILABLE | NOT AVAILABLE | AVAILABLE | NOT AVAILABLE | AVAILABLE |
|---|---|---|---|---|---|

| SLEEPING | AWAKE |
|---|---|

| NOT COMMUTING | COMMUTE | NOT COMMUTING |
|---|---|---|

| NO MEETING | MEETING | NO MEETING |
|---|---|---|

*340*

| CATEGORY OF INPUT | SUB-CATEGORY | SUB-SUB-CATEGORY | SUB-SUB-SUB-CATEGORY | EXEMPLARY FUZZY INPUTS | EXEMPLARY CRISP INPUTS | Type of Context (Lifestyle, situational, clinical, Device) |
|---|---|---|---|---|---|---|
| | Data from Sensors | Physiological Sensors | CGM | Hyperglycemia | | |
| | | | | Euglycemia | 120 mg/dL | clinical |
| | | | | Hypoglycemia | | |
| | | | SMBG | Hyperglycemia | | |
| | | | | Euglycemia | 120 mg/dL | clinical |
| | | | | Hypoglycemia | | clinical |
| | | | physiologic uncertainty/confidence | | | |
| | | | Body Temperature (as temperature affects insulin absorption rate) | cold/normal/fever | 98.6 | clinical |
| | | | gait analysis | | | |
| | | | Skin Conductivity (stress or emotion) | unstressed / stressed | | clinical |
| | | | Hormone Data, e.g., cortisol, epinephrine, and so on | energy in/energy out, and so on | | clinical |
| | | | Heart Rate | low/normal/high | 70 bpm | clinical |
| | | Data from Pump | | basal / bolus | 1 unit basal | clinical |
| | | Non-Physiological Sensors | GPS | home / away | at gym on Main St. | situational |
| | | | Atmospheric pressure, e.g., flying | | flying / not flying | situational |
| | | | Accelerometer (can be used to detect exertion, sleep level) | low / medium / high exertion | ran 30 minutes | situational/ Lifestyle |
| | | | Exercise from sensor triboelectric effects, GPS | low / medium / high exertion | ran 30 minutes | lifestyle |

FIG. 16

| | | | | |
|---|---|---|---|---|
| | | Sensor Accuracy / Confidence Range / Signal Quality. May also include device uncertainty/confidence. E.g., CGM will only make decision recommendation if three previous five-minute values exist/are reported/are good, and are accompanied by trend arrow | 5% accuracy, 10% accuracy | device |
| | | External Temperature | cold / normal / high | 108 deg | situational |
| | SMBG | | hypo/eu/hyper | 120 mg/dL | clinical |
| | Exercise | Direct user input, calendar data and/or pattern data | strenuous / medium / easy | burned 1000 calories, walked 3 miles | lifestyle |
| | Goal (self-management, social goals, decision-support goals) | e.g., level of interaction, level of discretion, tight control, good control at work/school, good control before sleep so as to avoid being disturbed (may include calendar/clock as a input) | tight control at school & looser control | I want to wake up with my glucose at 100 | lifestyle/clinical |
| | Problem to be Solved | nightly lows | stay within euglycemic range | stay within 20 mg/dL of desired target | lifestyle |
| | A Desire for Therapy (level of therapy aggressiveness) | | "alert me a lot" | alert me 3x/day | lifestyle |
| User-Entered Data | Stress / Emotion / Feeling Data | | stressed out / feeling fine | heart rate elevated by x% | lifestyle/clinical |
| | Pain level (can even be considered its own sensitivity) | | low/medium/high | pain level 1-10 | lifestyle/clinical |
| | Sleep level | | high / low | slept 6.5 hours | lifestyle/clinical |
| | Data from a follower device | | acknowledgement / advice | therapy recommendation | lifestyle |
| | User Feedback | | prompt me for more feedback/prompt me for less feedback | prompt me for feedback no more than 1x/day | lifestyle/ situational |

FIG. 16 (CONT.)

| | | | | | |
|---|---|---|---|---|---|
| Real Time Data | | type of insulin | | | clinical |
| | | Desired readiness for upcoming activities (may sync with calendar data too); e.g., user has big event coming up, so they want to be reminded a lot before, but not during the event | | | |
| | | Meal Data | | big/medium/small | lifestyle |
| | | | GPS (e.g., Restaurant data combined with pattern data) | home / away | lifestyle |
| | | | Calendar data, e.g., combined with pattern data | | lifestyle |
| | | Meal Data | data from a microphone, e.g., "always on", Smart phone can identify when ordering at a restaurant, e.g., in combination with GPS | | lifestyle |
| | | | Inferred from signal, e.g., glucose signal or rate of change | | lifestyle |
| | | | Pattern Recognition | | lifestyle |
| | | Calendar | Derived from Camera App | small / medium / large | lifestyle |
| | | | | weekend/weekday | lifestyle |
| | | GPS | | home / away | lifestyle/ situational |
| | | CGM App | | hypo/eu/hyper | clinical |
| | Data from Apps, via a suitable API | Historical Data or Other Information | | categorized pattern of X or Y | clinical |
| | | SMBG (where such is not user entered) | | hypo/eu/hyper | clinical |
| | | Temperature Monitor (external or body) (where such is not user entered) | | cold / normal / hot | clinical |
| | | HealthKit | | acknowledgement / advice | various |
| | | Data from follower, e.g., from text messaging app | | therapy recommendation | lifestyle |

| Column | Value |
|---|---|
| Meal Data row | 20 g carbs |
| GPS row | at gym on Main St. |
| Calendar row | 30 g carbs |
| (weekend row) | Tuesday |
| GPS row | at gym on Main St. |
| CGM App row | 84 mg/dL |
| SMBG row | 84 mg/dL |
| Temperature row | 101 deg |

FIG. 16 (CONT.)

| | | | | |
|---|---|---|---|---|
| Bolus Calculator App (including not just bolus info but type/brand of insulin, and duration of delivery) | | big bolus / medium bolus / small bolus | 1.5 units | clinical |
| Time of Day | | day / night | | 1654 situational |
| "Relative" Time - one aspect of DS is that the user may want to bolus but that we know a more preferable time for them to bolus - so we prompt them accordingly, based on patterns, which then triggers a bolus calculator | | | | lifestyle/ situational |
| Big Data | patient categorization | obese / normal | patients over X BMI should consider Y | various |
| analyte rate of change or acceleration | | rise / rapid rise | 10 mg/dL/hour | clinical |
| | insulin | high/med/low | | lifestyle |
| sensitivities / resistances | sleep | high/med/low | | lifestyle |
| | meal | high/med/low | | lifestyle |
| | exercise | high/med/low | | lifestyle |
| Hierarchy within Risk Stratification (as more/less data is available, move down/up risk stratification) | | high risk / med risk / low risk | | various |
| glucose variability | | high/med/low | 25 mg/dL | clinical |
| Derived Data (data derived in real time) — User Emotion / Feeling, e.g., depression, whether user is talking with others a lot, whether they are trying to distract themselves by playing games, etc. Large # of emails, low bank balance, etc. | | | | |
| ability to distribute insulin, e.g., after boluses delivered, e.g., "take a walk" | | | | lifestyle |
| User desire for interaction with device (derived from level of interaction) | | | wants constant notification | clinical |
| | | high/med/low | | lifestyle |

FIG. 16 (CONT.)

| | Field | Description | Value | Category |
|---|---|---|---|---|
| | Sensor accuracy / confidence range / signal quality | may bear on decision-support mode, e.g., a device determined decision-support mode | high/med/low | 10% device |
| | recognized patterns | nightly lows | typical / atypical | lifestyle |
| | | post-prandial highs, etc. | typical / atypical | lifestyle |
| | SMBG | | hypo/eu/hyper | clinical |
| | type and brand of insulin | fast acting, slow acting, and so on | | clinical |
| | User savviness with technology | | neophyte / normal / savvy | lifestyle |
| | Goal | Hypoglycemia avoidance versus hyper-glycemia avoidance, more/less interaction, more/less alerts/alarms | high/med/low level of interaction | desire for specific low GV | lifestyle |
| | Problem to be Solved | | | lifestyle |
| | Desire (e.g., level of user discretion, desired level of interaction) | | | lifestyle |
| | decision-support mode | therapeutic, non-therapeutic, adjunctive, non-adjunctive, user goal mode, right problem to be solved mode, decision to be made mode | | lifestyle/device |
| | Target glucose | | within eu range | 100 mg/dL +/-10% | lifestyle/clinical |
| User-Entered Data | type of diabetes (and whether they are insulin-dependent) | If insulin-dependent, are they intensive insulin dependent or non-intensive insulin-dependent (intensive insulin-dependent typically associated with higher glucose rates of change as compared to non-insulin users) | | clinical |
| | Workout Data (to allow patterns in post workout glycemic fluctuations to be found, and for appropriate automatic or manual therapy modifications to be made) | cardio 1, cardio 2 and so on | | lifestyle |
| | Age | | child/teen/young adult/ middle age adult / old adult / elderly | 45 years old | Demographic |

FIG. 16 (CONT.)

| | | | | |
|---|---|---|---|---|
| | | Cardio Health / Cholesterol | | clinical |
| | | Gender | good/poor | demographic |
| | | | M/F | M/F |
| | | Type of Mathematical Calculation (may be entered by physician/technician/user- may be related to desired level of accuracy / interaction) | fuzzy/approx versus as precise as possible | device |
| | | Illness / Pregnancy / Menstruation | type/level of illness, whether pregnant or menstruating | various |
| | | Medications / Smoking / Alcohol | smoker/non-smoker | lifestyle |
| | | Goal | 10 cigs / day | lifestyle |
| | | Historical Patterns | see patterns above | lifestyle/clinical |
| | | Gastric Emptying Duration, note that the same may also be user entered | | clinical |
| | Derived Data (data derived from analysis of past data) (overlaps in some cases with derived data from real time data) | decision-support mode | time duration | lifestyle/device |
| | | situational parameter associated with variable or poorly predicted glucose levels, e.g., time of day, day of week, type of event, etc. May also be associated with glucose variability | | various |
| | | user savviness/level of comfort with technology | "I really like data" versus "I don't want any interruptions" | lifestyle |
| | | Other Historical Conclusions About Data | glucose variability | various |
| Non-Real Time Data, typically Historic Data, e.g., Stored Data | Other non-real- time data | data about follower, e.g., tone of communication, language used | follower desires updates or not | lifestyle |
| | | | follower desires hourly updates | lifestyle |

FIG. 16 (CONT.)

SYSTEM AND METHOD FOR DECISION SUPPORT

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/628,895, filed on Feb. 9, 2018. The aforementioned application is incorporated by reference herein in its entirety, and is hereby expressly made a part of this specification.

TECHNICAL FIELD

The present development relates generally to medical devices such as analyte sensors, including systems and methods for using the same to provide support for treatment decision-making.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels.

Diabetes conditions are sometimes referred to as "Type 1" and "Type 2". A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This document discusses, among other things, systems and methods to determine a time for delivery or determination of decision-support guidance for a patient or caregiver.

An example (e.g., "Example 1") of subject matter (e.g., a method or system) may include measuring, determining, or receiving a first real-time datum associated with a patient, determining a state the patient is in using at least in part a model and the first real-time datum, determining a guidance message, wherein the guidance message is based at least in part on the determined state, and providing the determined personalized guidance message through a user interface at a time calculated to enable intervention prior to a transition to an undesirable physiologic state.

In Example 2, the subject matter of Example 1 may be configured such that determining a guidance message is further based on a timing of the determining the guidance message or a time associated with the determined state.

In Example 3, the subject matter of Example 1 or 2 may be configured such that the model includes a state indicative of a convenience or availability of the patient to participate in an intervention.

In Example 4, the subject matter of any one or any combination of Examples 1-3 may be configured such that the guidance message is based at least in part on a projected transition to the undesirable physiologic state.

In Example 5, the subject matter of any one or any combination of Examples 1-4 may be configured such that the guidance message is based at least in part on a determination that a projected transition from a present state to a projected state is a low-probability transition.

In Example 6, the subject matter of any one or any combination of Examples 1-5 may be configured such that the model includes a patient physiology model and determining a state the patient is in is based at least on applying the first real-time datum to the patient physiology model.

In Example 7, the subject matter of any one or any combination of Examples 1-6 may be configured such that the model includes a behavior model.

In Example 8, the subject matter of any one or any combination of Examples 1-7 may be configured such that a behavior model is based on a machine-learned characteristic of the patient, the machine-learned characteristic being based on a behavioral or contextual pattern.

In Example 9, the subject matter of any one or any combination of Examples 1-8 may be configured such that the behavior model is based on a set of one or more steps determined to be likely to be performed by the patient.

In Example 10, the subject matter of any one or any combination of Examples 1-9 may be configured such that a behavior model is based on a set of one or more objectives determined to be likely attainable by the patient.

In Example 11, the subject matter of any one or any combination of Examples 1-10 may be configured such that the model includes a behavior model that is a pattern.

In Example 12, the subject matter of any one or any combination of Examples 1-11 may be configured such that the model includes a patient physiology model based on a physiological pattern and a behavior model based on a behavioral pattern.

In Example 13, the subject matter of any one or any combination of Examples 1-12 may be configured such that the first real-time datum indicates a deviation from an expected behavioral pattern.

In Example 14, the subject matter of any one or any combination of Examples 1-13 may be configured such that a behavior model indicates a tendency to over correct at a meal associated with a meal time, the first real-time datum indicates that a mealtime is imminent, and the guidance message corresponds to a lessened overcorrection at the mealtime.

In Example 15, the subject matter of any one or any combination of Examples 1-14 may be configured such that the model includes a behavioral pattern that includes a long-term behavioral pattern based on long-term patterns of behavior and a short-term behavioral pattern associated with current behavior.

In Example 16, the subject matter of Example 15 may be configured such that the behavior model is based on the long-term behavioral pattern and is further based on the short-term behavioral pattern.

In Example 17, the subject matter of Example 16 may be configured such that the short-term behavioral pattern is based on one or more selected from the group consisting of: engagement with a mobile device, accelerometer data, frequency of checking glucose concentration, calendar data, and any combinations thereof.

In Example 18, the subject matter of any one or any combination of Examples 1-17 may be configured such that the state is based in part on a measurement model.

In Example 19, the subject matter of Example 18 may be configured such that the measurement model is based on a continuous glucose concentration monitoring system associated with the patient.

In Example 20, the subject matter of any one or any combination of Examples 1-19 may further include measuring glucose concentration data subsequent to the rendering a guidance message and using the measured subsequent data to improve one or more of the models.

In Example 21, the subject matter of any one or any combination of Examples 1-19 may be configured such that the glucose concentration data measured subsequent to the rendering is fed back to a measurement model or the behavior model or the patient physiology model, or to a combination thereof.

In Example 22, the subject matter of any one or any combination of Examples 1-21 may be configured such that the model includes a pattern selected from the group consisting of: a physiological pattern, a contextual pattern, or a behavioral pattern, or a combination of these patterns.

In Example 23, the subject matter of any one or any combination of Examples 1-22 may be configured such that the physiological pattern is based on a physiology model.

In Example 24, the subject matter of any one or any combination of Examples 1-23 may be configured such that the model is a based on a combination of patterns selected from the group consisting of: a physiological pattern, a contextual pattern, or a behavioral pattern.

In Example 25, the subject matter of any one or any combination of Examples 1-24 may be configured such that the determining a guidance message includes determining multiple guidance messages based on the state and the first real-time datum and selecting one of the determined multiple guidance messages further based on the state and the first real-time datum.

In Example 26, the subject matter of Example 25 may be configured such that the selecting is further based on a ranking scheme, a prioritization scheme, or based on a comparing of the multiple guidance messages to one or more associated thresholds.

In Example 27, the subject matter of any one or any combination of Examples 1-26 may further include determining an expected diabetic response of the patient based on the state and the first real-time datum, wherein the guidance message is personalized to the patient further based on the expected diabetic response, wherein the patient is provided with an actionable message calculated to move the expected diabetic response towards a desired diabetic response.

In Example 28, the subject matter Example 27 may be configured such that the desired diabetic response is relative to the state and the first real-time datum, wherein the desired diabetic response is selected from the group consisting of: an improved diabetic response, a potential improved diabetic response, an idealized response, or an optimized response.

In Example 29, the subject matter of any one or any combination of Examples 1-28 may be configured such that the guidance message is based on a functional relationship between expected diabetic response and a desired diabetic response.

In Example 30, the subject matter of Example 29 may be configured such that the functional relationship is a difference between a glucose concentration level associated with the expected diabetic response and a glucose concentration level associated with the desired diabetic response.

In Example 31, the subject matter of Example 30 may be configured such that the glucose concentration level associated with the desired diabetic response is a target glucose concentration level or a target glucose concentration range.

In Example 32, the subject matter of any one or any combination of Examples 29-31 may be configured such that the functional relationship is based on whether the expected diabetic response matches a predetermined condition associated with the desired diabetic response.

In Example 33, the subject matter of Example 32 may be configured such that the predetermined condition is a target glucose concentration level, a target glucose concentration range, a glucose concentration signal signature, a rate of change associated with a glucose concentration level, or a combination thereof.

In Example 34, the subject matter of any one or any combination of Examples 1-33 may be configured such that the guidance message further comprises one or more reasons associated with the functional relationship, whereby the patient may be informed as to why the guidance message is being rendered.

In Example 35, the subject matter of any one or any combination of Examples 1-34 may be configured such that the guidance message includes an actionable prompt.

In Example 36, the subject matter of Example 34 may be configured such that the guidance message includes an actionable prompt that is calculated to cause the patient's glucose concentration level to move towards a target level or a target range.

In Example 37, the subject matter of any one or any combination of Examples 1-36 may be configured such that the guidance message includes an affirmation of current actions associated with the patient.

In Example 38, the subject matter of any one or any combination of Examples 1-37 may be configured such that the first real-time datum is measured, received, or determined by a smart phone.

In Example 39, the subject matter of any one or any combination of Examples 1-38 may be configured such that the first real-time datum is measured, received, or determined by a wearable device.

In Example 40, the subject matter of any one or any combination of Examples 1-39 may be configured such that the first real-time datum is measured, received, or determined by a wearable device in combination with a smart phone.

In Example 41, the subject matter of any one or any combination of Examples 1-40 may be configured such that the first real-time datum is measured, received, or determined by an external device.

In Example 42, the subject matter of Example 41 may be configured such that the external device is an accelerometer.

In Example 43, the subject matter of any one or any combination of Examples 1-42 may be configured such that the first real-time datum includes a time of day, a characteristic or signature signal measured by an accelerometer, or a location determined by a GPS circuit.

In Example 44, the subject matter of any one or any combination of Examples 1-43 may be configured such that the first real-time datum includes a change of state.

In Example 45, the subject matter of any one or any combination of Examples 1-44 may be configured such that the change of state is detected by a clock, an accelerometer, or a GPS circuit.

In Example 46, the subject matter of any one or any combination of Examples 1-45 may be configured such that the first real-time datum includes a user request for a decision support prompt.

In Example 47, the subject matter of any one or any combination of Examples 1-46 may be configured such that the first real-time datum includes data received from a continuous glucose concentration monitoring system.

In Example 48, the subject matter of any one or any combination of Examples 1-47 may further include measuring, determining, or receiving a second real-time datum, wherein the second real-time datum is used in determining the state the patient is in.

In Example 49, the subject matter of any one or any combination of Examples 1-48 may be configured such that the determined personalized guidance message occurs at a time calculated to be useful in management of a patient glucose concentration level.

Example 50 is a system comprising: a glucose concentration sensor configured to detect a patient glucose concentration level; a communication circuit configured to receive the patient glucose concentration level from the glucose concentration sensor; a memory circuit including a stored model; and a processor configured to: receive the patient glucose concentration level; execute stored instructions to apply the patient glucose concentration level to the stored model to determine a state; and determine a guidance message based at least in part on the determined state.

In Example 51, the subject matter of Example 50 optionally includes the processor being configured to determine the guidance message based at least in part on a temporal pattern.

In Example 52, for the subject matter of any one or more of Examples 50-51, optionally, the model includes a physiologic model, determining a state includes determining a physiologic state.

In Example 53, the subject matter of Example 52 optionally includes the processor being configured to: determine a behavioral state; and determine the guidance message based at least in part on the behavior state.

In Example 54, the subject matter of any one or more of Examples 50-53 optionally includes the processor being configured to provide a therapy recommendation based at least in part on the determined state.

In Example 55, for the subject matter of any one or more of Examples 50-54, optionally, the system includes a mobile device, the mobile device including the memory circuit, and the processor.

In Example 56, for the subject matter of Example 55, optionally, the mobile device includes the communication circuit, and the glucose concentration sensor includes a glucose concentration sensor communication circuit configured to communicate with the communication circuit.

In Example 57, for the subject matter of Example 56, optionally, the mobile device communication circuit includes a first wireless transceiver, and the glucose concentration sensor communication circuit includes a second wireless transceiver, wherein the mobile device communication circuit and the glucose concentration sensor communication circuit communicate using a wireless communication protocol.

In Example 58, for the subject matter of any one or more of Examples 55-57, optionally, the mobile device includes a user interface configured to provide guidance message.

In Example 59, the subject matter of Example 58 optionally includes the mobile device being configured to receive user input through the user interface, and the processor is configured to receive the user input and apply both the user input and the patient glucose concentration level to the model to determine the state.

In Example 60, the subject matter of any one or more of Examples 55-59 optionally includes an insulin delivery system.

In Example 61, for the subject matter of Example 60, optionally, the insulin delivery system includes an insulin pump.

In Example 62, for the subject matter of any one or more of Examples 60-61, optionally, the insulin delivery system includes an insulin pen.

In Example 63, the subject matter of any one or more of Examples 50-62 optionally includes a user interface configured to provide the guidance message to a patient.

Example 64 is a method of delivering physiologic glucose concentration management guidance comprising: receiving a datum indicative of a glucose concentration level; determining a state by applying the datum to a model; and determining a guidance message based at least in part on the state and a temporal pattern.

In Example 65, for the subject matter of Example 64, optionally, the temporal pattern includes a learned pattern of patient behavior.

In Example 66, for the subject matter of any one or more of Examples 64-65, optionally, the temporal pattern includes a calendar.

In Example 67, the subject matter of Example 66 optionally includes determining a guidance message being based at least in part on an upcoming event in the calendar.

In Example 68, the subject matter of Example 67 optionally includes determining a guidance message being based at least in part on a projected change in insulin sensitivity calculated based at least in part on the upcoming event in the calendar.

In Example 69, for the subject matter of any one or more of Examples 64-68, optionally, the model includes a physiologic model, determining a state includes determining a physiologic state, and determining a guidance message includes determining from the temporal pattern and the physiologic model that a transition to an undesirable physiologic state is likely to occur.

In Example 70, for the subject matter of Example 69, optionally, determining a guidance message includes determining an intervention to avoid the transition to the undesirable physiologic state and determining, based at least in part on the temporal pattern, a time for delivery of the guidance message to enable intervention to prevent the transition.

In Example 71, the subject matter of any one or more of Examples 64-70 optionally includes determining a delivery time for delivery of the guidance message using the temporal pattern.

In Example 72, for the subject matter of Example 71, optionally, includes determining a delivery time includes selecting a delivery time when a host is likely to be available based at least in part on the temporal pattern.

In Example 73, for the subject matter of any one or more of Examples 71-72, optionally, wherein determining a delivery time includes identifying an upcoming period of patient unavailability and selecting a time for delivery of the guidance message prior to the period of patient unavailability.

In Example 74, for the subject matter of any one or more of Examples 64-73, optionally, determining a guidance message includes identifying a period of patient unavailability based at least in part on the temporal pattern, and wherein the guidance message is calculated to promote glucose concentration stability during the period of unavailability.

In Example 75, the subject matter of any one or more of Examples 64-74 optionally includes determining an engagement state; determining a messaging frequency based at least in part on the engagement state; and determining a time for delivering the guidance message based at least in part on the messaging frequency.

In Example 76, the subject matter of Example 75 optionally includes determining that the engagement state has changed to a changed engagement state; determining a new messaging frequency based at least in part on the changed engagement state; determining a second guidance message; and determining a second time for delivering the second guidance based at least in part on the new messaging frequency.

In Example 77, the subject matter of any one or more of Examples 64-76 optionally includes the state being a disease state describing a host disease stage.

In Example 78, the subject matter of Example 77 optionally includes receiving a second datum indicative of a second glucose concentration level; determining a second disease state describing a second host disease stage at least in part by applying the second datum to the model; and determining a second guidance message based at least in part on the second disease state.

In Example 79, for the subject matter of any one or more of Examples 64-78, optionally, determining a state includes determining a physiologic state.

In Example 80, for the subject matter of Example 79, optionally, determining a physiologic state includes determining an insulin state, an energy absorption state, and an energy expenditure state.

In Example 81, the subject matter of any one or more of Examples 64-80 optionally includes receiving a behavioral input, wherein determining a state includes applying both the datum and the behavioral input to the model.

In Example 82, for the subject matter of Example 81, optionally, includes receiving a behavioral input includes receiving patient activity information.

Example 83 is a method of delivering physiologic glucose concentration management guidance comprising: receiving a datum indicative of a glucose concentration; determining a physiologic state using the datum; determining a behavioral state; determining a guidance message based at least in part on the physiologic state and the behavioral state; and delivering the guidance message using a user interface.

In Example 84, the subject matter of Example 83 optionally includes determining a time to deliver guidance that enables timely intervention to affect the glucose concentration.

In Example 85, the subject matter of any one or more of Examples 83-84 optionally includes determining a level of interest in guidance based at least in part on the behavioral state and the physiologic state.

In Example 86, the subject matter of Example 85 optionally includes determining a level of interest in therapy guidance being based at least in part on prior user requests for guidance.

In Example 87, for the subject matter of any one or more of Examples 83-86, optionally determining a behavioral state includes receiving a behavioral input and applying the behavioral input to a behavior state model.

In Example 88, for the subject matter of any one or more of Examples 83-87 optionally determining a behavioral state includes consulting a user calendar of scheduled events.

In Example 89, for the subject matter of any one or more of Examples 83-88 optionally determining a physiologic state includes applying the datum to a physiology state model.

In Example 90, for the subject matter of Example 89 optionally, the physiology state model includes a glucose concentration level.

In Example 91, for the subject matter of Example 90, optionally, the physiology state model further includes one or more of an insulin state, an energy absorption state, and an energy expenditure state.

In Example 92, the subject matter of any one or more of Examples 83-91 optionally includes determining a measurement state, the measurement state including a degree of accuracy or precision of the datum indicative of the glucose concentration.

In Example 93, for the subject matter of any one or more of Examples 83-92, optionally, determining a guidance message includes determining that a low-probability physiologic state transition is likely to occur, wherein the guidance message provides advance notice of the low-probability physiologic state transition.

In Example 94, for the subject matter of Example 93, optionally, the low-probability physiologic state transition includes a transition to low glucose concentration level or a high glucose concentration level.

In Example 95, for the subject matter of any one or more of Examples 93-94, optionally, determining a guidance message includes determining that the low-probability physiologic state transition is likely to occur at a time that is inconvenient, and the guidance message provides advance warning of the projected low-probability physiologic state transition to enable intervention to avoid the low-probability physiologic state transition.

In Example 96, the subject matter of Example 95 optionally inlcudes determining that the low-probability physiologic state transition being likely to occur at a time that is inconvenient includes applying a behavior input to a behavioral state model.

In Example 97, the subject matter of any one or more of Examples 83-96 optionally includes receiving an additional physiologic parameter, wherein the physiologic state is determined using both the datum and the additional physiologic parameter.

In Example 98, for the subject matter of Example 97, optionally, the additional physiologic parameter includes a body temperature, a heart rate, or a respiration rate.

In Example 99, the subject matter of any one or more of Examples 83-98 optionally includes during a learning period, receiving a learning datum describing at least one of a physiologic state or the behavioral state, wherein at least one of the physiologic state or the behavioral state is determined after the learning period using the learning datum.

Example 100 is a method of determining and rendering a calculated guidance message personalized and useful to a patient for therapeutic management of the patient's diabetes, comprising: receiving data relating to a patient, the data including a real-time glucose concentration level; determining a patient state by applying the data to a state model; and providing a therapy recommendation based at least in part on the determined state.

In Example 101, for the subject matter of Example 100, optionally, the patient state includes an insulin on board state, an insulin sensitivity state, and a dietary consumption state.

In Example 102, the subject matter of any one or more of Examples 100-101 optionally includes the state model being a probabilistic state model.

In Example 103, for the subject matter of Example 102, optionally, the state model includes state transition probabilities are learned from retrospective data.

In Example 104, the subject matter of any one or more of Examples 100-103 optionally includes refining the state model using data received after delivery of the therapy recommendation.

Example 105 is a method of providing decision support functionality for a user, comprising: loading a model into a memory of a computing environment; receiving a datum indicative of a glucose concentration value of the user; and causing a display of a calculated insight on a user interface of the computing environment, the insight calculated using at least the model and the datum indicative of the glucose concentration value.

In Example 106, the subject matter of Example 105 optionally includes the causing a display being initiated by a user request.

In Example 107, the subject matter of Example 106 optionally includes the user request being associated with data entry of a planned activity, and where the calculated insight indicates a user act calculated by one or more of the models to result in a desired outcome associated with the glucose concentration value.

In Example 108, the subject matter of Example 107 optionally includes the desired outcome being a glucose concentration value within a predetermined target range.

In Example 109, the subject matter of any one or more of Examples 107-108 optionally includes the desired outcome being a glucose concentration value having a rate of change within a predetermined target range.

In Example 110, the subject matter of any one or more of Examples 107-109 optionally includes the planned activity being a meal, and wherein the calculated insight being a calculated or predicted effect of the meal on the glucose concentration value.

In Example 111, for the subject matter of any one or more of Examples 107-110 optionally, the calculated insight displayed includes an interactive recommendation and at least one factor used in determining the interactive recommendation.

In Example 112, the subject matter of any one or more of Examples 105-111 optionally includes causing a display of the calculated insight being initiated by an occurrence of an event that matches a predetermined condition.

In Example 113, the subject matter of any one or more of Examples 105-112 optionally includes causing a display of the calculated insight being initiated by an occurrence of an event that matches a calculated condition, the calculated condition calculated based at least in part on the model, or the datum indicative of the glucose concentration value, or a combination thereof.

In Example 114, the subject matter of Example 113 optionally includes when a therapy adjustment exposes the user to more risk than was present before the therapy adjustment, then alerts and/or alarms are adjusted to have additional sensitivity for a period of time following the therapy adjustment.

In Example 115, the subject matter of any one or more of Examples 113-114 optionally includes detecting when a time period exists following a potential treatment decision that triggers a more frequent instantiation of a CGM app than priori the potential treatment decision and increasing a messaging frequency of a decision support.

In Example 116, the subject matter of any one or more of Examples 113-115 optionally includes the messaging being sent to the user or to a follower of the user.

In Example 117, the subject matter of any one or more of Examples 105-116 optionally includes detecting an occurrence of a trend using the received datum, the trend associated with a recognized pattern.

In Example 118, the subject matter of any one or more of Examples 105-117 optionally includes receiving a datum from an external data source.

In Example 119, the subject matter of Example 118 optionally includes the external data source being an insulin pen or pump, and wherein the calculated insight includes information about insulin on board.

In Example 120, the subject matter of Example 119 optionally includes the external data source being an insulin pen or pump, and wherein the calculated insight is expressed with two values, one indicating for use if user exercise is planned, and another indicating for use if no user exercise is planned.

In Example 121, the subject matter of any one or more of Examples 119-120 optionally includes the external data source being an accelerometer, and wherein the calculated insight includes information about an effect of exercise on glucose concentration value.

In Example 122, the subject matter of any one or more of Examples 119-121 optionally includes the external data source being a camera or GPS receiver, and wherein the calculated insight includes information about an effect of meal size and composition on glucose concentration value.

In Example 123, the subject matter of any one or more of Examples 119-122 optionally inlcudes the external data source a user interface, wherein the user interface is configured to received data about user goals, and wherein the calculated insight includes information about percentage time in a target range and an indication of the target range.

In Example 124, the subject matter of any one or more of Examples 105-123 optionally includes loading into a memory of a computing environment a measurement model of a continuous glucose concentration monitoring system associated with the user, and the calculated insight is further based on the measurement model.

In Example 125, the subject matter of Example 124 optionally includes the calculated insight being calculated using an algorithm that is based at least in part on glucose concentration variability or likelihood and/or severity of glucose concentration excursions.

In Example 126, the subject matter of any one or more of Examples 105-125 optionally includes the causing a display being based on calculations performed on a periodic basis.

In Example 127, the subject matter of Example 126 optionally includes the periodic basis being determined based on of a series of mealtimes occurring at substantially the same time.

In Example 128, the subject matter of any one or more of Examples 126-127 optionally includes the periodic basis being determined based on of a series of similar glycemic responses.

In Example 129, the subject matter of Example 128 optionally includes the similar glycemic responses being spikes.

In Example 130, the subject matter of any one or more of Examples 126-129 optionally includes the periodic basis being determined based on of a series of similar dosing strategies.

In Example 131, the subject matter of any one or more of Examples 126-130 optionally includes the periodic basis being determined based on basis of a series of unreliable outcomes, where a glucose concentration level drifted over a specified percentage or amount away from a target zone following a potential treatment decision.

In Example 132, for the subject matter of any one or more of Examples 105-131 optionally, the display of the calculated insight includes the display of a probability cone, the probability cone based on prior data of the user.

In Example 133, for the subject matter of any one or more of Examples 105-132 optionally, the display of the calculated insight includes the display of a probability cone, the probability cone based on population data.

In Example 134, the subject matter of Example 133 optionally includes the population data being culled from persons having one or more demographic traits in common with the user.

In Example 135, for the subject matter of any one or more of Examples 105-134, optionally, the display of the calculated insight includes the display of two separate trend indicators, one determined using data measured during weekdays and one determined using data measured during weekends.

In Example 136, the subject matter of any one or more of Examples 105-135 optionally includes the insight being calculated by the computing environment.

In Example 137, the subject matter of any one or more of Examples 105-136 optionally includes the insight being calculated by a connected server.

In Example 138, for the subject matter of any one or more of Examples 105-137 optionally, the model includes a physiologic model and a behavior model.

In Example 139, the subject matter of Example 138 optionally includes the behavior model being configured to determine level of concern factors, the level of concern factors selected from the group consisting of: concern about physiologic state, consequence of treatment decisions, and/or potential future states.

In Example 140, the subject matter of Example 139 optionally includes the concern about physiologic state being determined by detecting a frequency of checking an application related to diabetes or detecting how often SMBG values are being entered.

In Example 141, the subject matter of any one or more of Examples 139-140 optionally includes the behavior model being configured to determine level of engagement factors, the level of engagement factors selected from the group consisting of: response time, level of treatment activity, and/or type of support.

In Example 142, the subject matter of any one or more of Examples 139-141 optionally includes the computing environment being a mobile device, the method further comprising learning the physiological model by a second computer system, wherein loading the model into a memory of a computing environment includes loading the learned physiological model into the mobile device.

In Example 143, the subject matter of Example 142 optionally includes learning the behavior model by a second computer system, wherein loading the model into a memory of a computing environment includes loading the learned behavior model into the mobile device.

In Example 144, for the subject matter of any one or more of Examples 142-143 optionally, the mobile device determines the calculated insight without requiring access to the second computer system.

Example 145 is a system comprising: a glucose concentration sensor configured to detect a host glucose concentration; a communication circuit configured to receive the host glucose concentration from the glucose concentration sensor; a memory circuit including a stored model; and a processor configured to: receive host glucose concentration data sensed by the glucose concentration sensor; determine a host state change associated with the host glucose concentration data; determine a guidance message based at least in part on the host state change; and delivering the guidance message through a user interface.

In Example 146, the subject matter of Example 145 optionally includes the processor being configured to determine that the host state change is atypical, wherein the determining of the guidance message is based at least in part on the atypicality of the state change.

In Example 147, for the subject matter of any one or more of Examples 145-146 optionally, determining the host state change comprises determining from a model that a low-probability state transition has occurred or is likely to occur, wherein the determining of the guidance message is based at least in part on the determination that the low-probability state transition has occurred or is likely to occur.

In Example 148, for the subject matter of any one or more of Examples 145-147 optionally, determining the host state change comprises identifying a likely transition to an undesirable host state and the guidance message is determined and delivered at a time such that the host can intervene to avoid the transition to the undesirable host state.

In Example 149, for the subject matter of any one or more of Examples 145-148 optionally, the system includes a mobile device, the mobile device including the memory circuit, and the processor.

In Example 150, for the subject matter of Example 149, optionally, the mobile device includes the communication circuit, and the glucose concentration sensor includes a glucose concentration sensor communication circuit configured to communicate with the communication circuit.

In Example 151, for the subject matter of any one or more of Examples 149-150, optionally, the mobile device communication circuit includes a first wireless transceiver, and the glucose concentration sensor communication circuit includes a second wireless transceiver, wherein the mobile device communication circuit and the glucose concentration sensor communication circuit communicate using a wireless communication protocol.

In Example 152, the subject matter of any one or more of Examples 145-151 optionally includes an insulin delivery system.

In Example 153, the subject matter of any one or more of Examples 145-152 optionally includes the state change being from a first disease state describing a first host disease stage to a second disease state indicating a second host disease stage, wherein the processor is further configured go determine a second guidance message based at least in part on the second disease stage.

Example 154 is a method of delivering physiologic glucose concentration management guidance comprising: receiving a datum indicative of a glucose concentration; determining a patient state by applying the datum to a model; determining whether the patient state is atypical; determining a guidance message based on the atypicality of the patient state; and delivering the guidance message through a user interface.

In Example 155, for the subject matter of Example 154, optionally, determining whether the patient state is atypical includes determining whether the patient state is atypical for a given set of conditions.

In Example 156, for the subject matter of any one or more of Examples 154-155 optionally, determining whether the patient state is atypical includes determining whether a low-likelihood state transition has occurred.

In Example 157, for the subject matter of any one or more of Examples 154-156 optionally, determining a guidance message includes determining whether a low-likelihood state transition is projected to occur.

In Example 158, for the subject matter of any one or more of Examples 154-157 optionally, determining a patient state includes determining a physiological state and a behavioral state and determining whether the physiological state is atypical for the determined behavioral state.

In Example 159, for the subject matter of any one or more of Examples 154-158 optionally, determining whether the patient state is atypical includes identifying a blood glucose concentration level that deviates from a controlled blood glucose concentration range a time or in a circumstance when blood glucose concentration is typically in a controlled range.

In Example 160, for the subject matter of any one or more of Examples 154-159 optionally, determining whether the patient state is atypical includes identifying a blood glucose concentration trend leading to a high or low blood glucose concentration state a time or in a circumstance when blood glucose concentration is typically in a controlled range.

In Example 161, for the subject matter of any one or more of Examples 154-160 optionally, determining whether the patient state is atypical includes anticipating a shift to a low blood glucose concentration state at a time or in a circumstance when blood glucose concentration is typically well controlled.

Example 162 is a method of delivering physiologic glucose concentration management guidance comprising: receiving a datum indicative of a glucose concentration; determining a patient state by applying the datum to a model; determining from the model that a low-probability state transition has occurred or is likely to occur; and delivering through a user interface a guidance message based on the determination that the low-probability state transition has occurred or is likely to occur.

In Example 163, for the subject matter of Example 162, optionally, the method includes determining that a low-probability state transition is likely to occur, wherein the guidance message provides advance notice of the low-probability state transition.

In Example 164, for the subject matter of any one or more of Examples 162-163 optionally, the low-probability physiologic state transition includes a transition to a low glucose concentration level or a high glucose concentration level.

In Example 165, for the subject matter of any one or more of Examples 162-164, optionally, determining a guidance message includes determining that the low-probability state transition is likely to occur at a time that is inconvenient.

In Example 166, for the subject matter of Example 165, optionally, determining that the low-probability state transition is likely to occur at a time that is inconvenient includes reference to user calendar of scheduled events.

In Example 167, for the subject matter of any one or more of Examples 165-166, optionally, determining that the low-probability state transition is likely to occur at a time that is inconvenient includes reference to a behavioral state model.

In Example 168, for the subject matter of any one or more of Examples 162-167, optionally, delivering the guidance message includes determining a time period when the patient or a caregiver is likely to be available to take action to prevent the low-probability state transition and delivering the guidance message during the determined time period.

In Example 169, for the subject matter of Example 168, optionally, determining a time period when the patient is likely to be available to take action to prevent the low-probability state transition includes referencing a calendar of scheduled events.

In Example 170, for the subject matter of any one or more of Examples 168-169 optionally, determining a time period when the patient or a caregiver is likely to be available to take action to prevent the low-probability state transition includes using the model.

In Example 171, for the subject matter of any one or more of Examples 168-170 optionally, using the model includes using a pattern of user activity or user location information to determine a time period when the patient or a caregiver is likely to be available.

Example 172 is a method of delivering physiologic glucose concentration management guidance comprising: receiving a datum indicative of a glucose concentration; receiving one or more behavioral, environmental or contextual inputs; identifying a likely transition to an undesirable patient state by applying the datum and the one or more behavioral, environmental or contextual input to a model; determining a guidance message based on the likely transition to an undesirable patient state; and delivering the guidance message, wherein the guidance message is determined and delivered at a time such that the patient can intervene to avoid the transition to an undesirable patient state.

In Example 173, for the subject matter of Example 172, optionally, receiving a behavioral, environmental or contextual input includes receiving accelerometer data.

In Example 174, for the subject matter of any one or more of Examples 172-173, optionally, receiving a behavioral, environmental or contextual input includes receiving information from a calendar about a scheduled event.

In Example 175, for the subject matter of any one or more of Examples 172-174, optionally, receiving a behavioral, environmental or contextual input includes receiving input from a user through a user interface.

In Example 176, for the subject matter of any one or more of Examples 172-175, optionally, receiving a behavioral, environmental or contextual input includes receiving information from a user about completion, initiation, or anticipation of exercise.

In Example 177, for the subject matter of any one or more of Examples 172-176, optionally, receiving a behavioral, environmental or contextual input includes detecting that a user is driving.

In Example 178, for the subject matter of any one or more of Examples 172-177, optionally, receiving one or more behavioral, environmental or contextual input includes receiving location information.

In Example 179, for the subject matter of any one or more of Examples 172-178, optionally, receiving one or more behavioral, environmental or contextual input includes receiving an ambient temperature or an ambient pressure.

In Example 180, the subject matter of any one or more of Examples 172-179 optionally includes receiving a body temperature, heart rate, or respiration rate.

In Example 181, the subject matter of Example 180 optionally includes learning the model based upon one or more patterns of received information.

In Example 182, for the subject matter of Example 181, optionally, learning the model includes learning a pattern of insulin sensitivity as a function of time.

In Example 183, for the subject matter of Example 182, optionally, learning the model includes learning a pattern of insulin sensitivity as a function of time elapsed after a period of physical exertion.

In Example 184, the subject matter of any one or more of Examples 172-183 optionally includes determining a user query and providing the user query to a user, wherein the behavioral, environmental or contextual input is received in response to the user query.

In Example 185, for the subject matter of any one or more of Examples 172-184, optionally, receiving a datum indicative of a glucose concentration includes receiving a datum from a continuous glucose concentration monitoring system.

Example 186 is a system comprising: a glucose concentration sensor configured to detect a host glucose concentration; a communication circuit configured to receive the host glucose concentration from the glucose concentration sensor; a memory circuit including a stored model; and a processor configured to: access a datum associated with a host; determine a state of the host using the datum; determine a guidance message based at least in part on the determined state; select a time for providing the guidance message; and provide the guidance message through a user interface at the selected time.

In Example 187, the subject matter of Example 186 optionally includes the time being calculated to enable intervention prior to a transition of the host to an undesirable physiologic state.

In Example 188, the subject matter of any one or more of Examples 186-187 optionally includes determining the guidance message being based at least in part on a personalized behavior model of the host, and the time being calculated to be useful to the host in therapeutic management of diabetes.

In Example 189, the subject matter of any one or more of Examples 186-188 optionally includes the determining of the state being based at least in part on a patient physiology model and a patient behavioral model.

Example 190 is a method of delivering physiologic glucose concentration management guidance comprising: measuring, determining, or receiving a first real-time datum associated with a patient; determining a state the patient is in using at least in part a model and the first real-time datum; determining a personalized guidance message, wherein the guidance message is based at least in part on the determined state; and providing the determined personalized guidance message through a user interface at a time calculated to enable intervention prior to a transition to an undesirable physiologic state.

In Example 191, the subject matter of Example 190 optionally includes determining a guidance message being further based on a timing of the determining the guidance message or a time associated with the determined state.

In Example 192, for the subject matter of any one or more of Examples 190-191, optionally, the model includes a state indicative of a convenience or availability of the patient to participate in an intervention.

In Example 193, the subject matter of any one or more of Examples 190-192 optionally includes the guidance message being based at least in part on a projected transition to the undesirable physiologic state.

In Example 194, the subject matter of Example 193 optionally includes the guidance message being based at least in part on a determination that a projected transition from a present state to a projected state is a low-probability transition.

In Example 195, for the subject matter of any one or more of Examples 190-194, optionally, the model includes a patient physiology model, and determining a state the patient is based at least on applying the first real-time datum to the patient physiology model.

In Example 196, for the subject matter of Example 195, optionally, the model further includes a behavior model.

In Example 197, the subject matter of Example 196 optionally includes the behavior model being based on a machine-learned characteristic of the patient, the machine-learned characteristic being based on a behavioral or contextual pattern.

In Example 198, the subject matter of any one or more of Examples 196-197 optionally includes the behavior model being based on a set of one or more steps determined to be likely to be performed by the patient.

In Example 199, the subject matter of any one or more of Examples 196-198 optionally includes the behavior model being based on a set of one or more objectives determined to be likely attainable by the patient.

In Example 200, for the subject matter of any one or more of Examples 196-199, optionally, the behavior model is a pattern.

In Example 201, the subject matter of any one or more of Examples 196-200 optionally includes the patient physiology model being based on a physiological pattern and the behavior model being based on a behavioral pattern.

In Example 202, the subject matter of Example 201 optionally includes the first real-time datum indicating a deviation from an expected behavioral pattern.

In Example 203, the subject matter of Example 202 optionally includes the behavior model indicating a tendency to over correct at a meal associated with a meal time, the first real-time datum indicating that a mealtime is imminent, and the guidance message corresponding to a lessened overcorrection at the mealtime.

In Example 204, for the subject matter of Example 203, optionally, the behavioral pattern includes a long-term behavioral pattern based on long-term patterns of behavior and a short-term behavioral pattern associated with current behavior.

In Example 205, the subject matter of Example 204 optionally includes the behavior model being based on the long-term behavioral pattern and being further based on the short-term behavioral pattern.

In Example 206, the subject matter of Example 205 optionally includes the short-term behavioral pattern being based on one or more selected from the group consisting of: engagement with mobile device, accelerometer data, frequency of checking glucose concentration, calendar data, and combinations of these.

In Example 207, the subject matter of any one or more of Examples 190-206 optionally includes determining a state being further based on a measurement model.

In Example 208, the subject matter of Example 207 optionally includes the measurement model being based on a continuous glucose concentration monitoring system associated with the patient.

In Example 209, the subject matter of Example 208 optionally includes measuring glucose concentration data subsequent to the determining a guidance message and using the measured subsequent data to improve one or more of the models.

In Example 210, the subject matter of Example 209 optionally includes the glucose concentration data measured subsequent to the determining being fed back to a measurement model or the behavior model or the patient physiology model, or to a combination thereof.

In Example 211, for the subject matter of any one or more of Examples 190-210, optionally, the model includes a pattern selected from the group consisting of: a physiological pattern, a contextual pattern, or a behavioral pattern, or a combination of these patterns.

In Example 212, the subject matter of Example 211 optionally includes the physiological pattern being based on a physiology model.

In Example 213, the subject matter of any one or more of Examples 190-212 optionally includes the model being a based on a combination of patterns selected from the group consisting of: a physiological pattern, a contextual pattern, or a behavioral pattern.

In Example 214, for the subject matter of any one or more of Examples 190-213, optionally, the determining a guidance message further comprises determining multiple guidance messages based on the state and the first real-time datum and selecting one of the determined multiple guidance messages further based on the state and the first real-time datum.

In Example 215, the subject matter of Example 214 optionally includes the selecting being further based on a ranking scheme, a prioritization scheme, or being based on a comparing of the multiple guidance messages to one or more associated thresholds.

In Example 216, the subject matter of any one or more of Examples 190-215 optionally includes determining an expected diabetic response of the patient based on the state and the first real-time datum, and the guidance message being personalized to the patient further based on the expected diabetic response, the patient being provided with an actionable message calculated to move the expected diabetic response towards a desired diabetic response.

In Example 217, the subject matter of Example 216 optionally includes the desired diabetic response being relative to the state and the first real-time datum, and the desired diabetic response being selected from the group consisting of: an improved diabetic response, a potential improved diabetic response, an idealized response, or an optimized response.

In Example 218, the subject matter of Example 217 optionally includes the guidance message being based on a functional relationship between the expected diabetic response and a desired diabetic response.

In Example 219, the subject matter of Example 218 optionally includes the functional relationship being a difference between a glucose concentration level associated with the expected diabetic response and a glucose concentration level associated with the desired diabetic response.

In Example 220, the subject matter of Example 219 optionally includes the glucose concentration level associated with the desired diabetic response being a target glucose concentration level or a target glucose concentration range.

In Example 221, the subject matter of Example 220 optionally includes the functional relationship being based on whether the expected diabetic response matches a predetermined condition associated with the desired diabetic response.

In Example 222, the subject matter of Example 221 optionally includes the predetermined condition being a target glucose concentration level, a target glucose concentration range, a glucose concentration signal signature, or a rate of change associated with a glucose concentration level.

In Example 223, for the subject matter of any one or more of Examples 217-222, optionally, the guidance message further comprises one or more reasons associated with the functional relationship, whereby the patient may be informed as to why the guidance message is being rendered.

In Example 224, for the subject matter of any one or more of Examples 190-223, optionally, the guidance message includes an actionable prompt.

In Example 225, for the subject matter of Example 224, optionally, the guidance message includes an actionable prompt that is calculated to cause the patient's glucose concentration level to move towards a target level or a target range.

In Example 226, for the subject matter of any one or more of Examples 190-225 optionally includes the guidance message includes an affirmation of current actions associated with the patient.

In Example 227, for the subject matter of any one or more of Examples 190-226, optionally, the first real-time datum is measured, received, or determined by a smart phone.

In Example 228, the subject matter of any one or more of Examples 190-227 optionally includes the first real-time datum being measured, received, or being determined by a wearable device.

In Example 229, the subject matter of any one or more of Examples 190-228 optionally includes the first real-time datum being measured, received, or determined by a wearable device in combination with a smart phone.

In Example 230, the subject matter of any one or more of Examples 190-229 optionally includes the first real-time datum being measured, received, or determined by an external device.

In Example 231, the subject matter of Example 230 optionally includes the external device being an accelerometer.

In Example 232, the subject matter of any one or more of Examples 190-231 optionally includes the first real-time datum being a time of day, a characteristic or signature signal measured by an accelerometer, or being a location determined by a GPS circuit.

In Example 233, the subject matter of any one or more of Examples 190-232 optionally includes the first real-time datum being a change of state.

In Example 234, the subject matter of Example 233 optionally includes the change of state being detected by a clock, an accelerometer, or a GPS circuit.

In Example 235, the subject matter of any one or more of Examples 190-234 optionally includes the first real-time datum being a user request for a decision support prompt.

In Example 236, the subject matter of any one or more of Examples 190-235 optionally includes the first real-time datum being received from a continuous glucose concentration monitoring system.

In Example 237, the subject matter of any one or more of Examples 190-236 optionally includes measuring, determining, or receiving a second real-time datum, wherein the second real-time datum is used in determining the state the patient is in.

In Example 238, the subject matter of any one or more of Examples 190-237 optionally includes providing the determined personalized guidance message at a time calculated to be useful in management of a patient glucose concentration level.

In Example 239, the subject matter of any one or more of Examples 190-238 optionally includes the state being a disease state describing a patient disease stage.

In Example 240, the subject matter of Example 239 optionally includes measuring, determining, or receiving a second real-time datum indicative of a second glucose concentration level; determining a second disease state describing a second patient disease stage at least in part by applying the second datum to the model; and determining a second guidance message based at least in part on the second disease state.

In Example 241, the subject matter of any one or more of Examples 190-240 optionally includes the state being an engagement state, further comprising: determining a messaging frequency based at least in part on the engagement state; and determining the time for providing the personalized guidance message based at least in part on the messaging frequency.

In Example 242, the subject matter of any one or more of Examples 190-241 optionally includes during a learning period, receiving a learning datum, determining the state of the patient being based at least in part on the learning datum.

Example 243 is a method of determining and delivering a calculated guidance message personalized and useful to a patient in therapeutic management of the diabetes of the patient, comprising: learning a personalized behavior model of the patient; receiving a real-time datum; determining a personalized guidance message to be rendered to the patient, the determining based at least in part on the time of determination of the personalized guidance message and the personalized behavior model of the patient; and determining a delivery time to provide the personalized guidance message using the learned personalized behavior model, wherein the delivery time is calculated to be useful to the patient in the therapeutic management of his or her diabetes.

In Example 244, for the subject matter of Example 243, optionally, learning a personalized behavior model of a patient includes machine learning a first characteristic of the patient.

In Example 245, the subject matter of Example 244 optionally includes the first characteristic being a pattern selected from the group consisting of: a physiological pattern, a contextual pattern, or a behavioral pattern, or a combination of these patterns.

In Example 246, the subject matter of Example 245 optionally includes delivering the personalized guidance message at the delivery time.

Example 247 is a method of determining and rendering a calculated guidance message personalized and useful to a patient in the therapeutic management of the diabetes of the patient, comprising: measuring, determining, or receiving a first real-time datum associated with the patient; using a model, determining a state the patient is in, the determining based on a patient physiology model, a behavioral model, and a measurement model, the state determined by the patient physiology model and the behavioral model and the real-time datum; determining a guidance message, wherein the guidance message is personalized to the patient based on at least the determined state, whereby the determined state and use of plural models enables a personalization of the guidance message; and providing the determined personalized guidance message via a user interface, such that the rendering occurs at a time calculated to be useful to the patient in the therapeutic management of their diabetes.

In Example 248, the subject matter of Example 247 optionally includes receiving a first real-time datum being a glucose concentration value.

In Example 249, the subject matter of Example 248 optionally includes receiving a first real-time datum being a time of day.

In Example 250, the subject matter of any one or more of Examples 248-249 optionally includes the patient physiology model being a state model that includes one or more of a glucose concentration state, an insulin-on-board state, and insulin sensitivity state, an energy absorption state, or an energy exertion state.

In Example 251, the subject matter of any one or more of Examples 248-250 optionally includes learning the model from a set of input data.

In Example 252, for the subject matter of Example 251, optionally, the set of input data includes one or more of clock time, time of day, glucose concentration level, insulin on board, patient activity, patient wellness, day of week, day of month, day of year, location, food consumed, or beverage consumed.

In Example 253, the subject matter of any one or more of Examples 251-252 optionally includes determining a deviation from an expected state after delivering the personalized guidance message, and adapting the model based on additional input information.

In Example 254, for the subject matter of Example 253, optionally, the set of input data includes information received through a user interface.

In Example 255, for the subject matter of any one or more of Examples 247-254, optionally, providing the determined personalized guidance message includes rendering the personalized guidance message on a user interface.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2B is an illustration that provides a more detailed illustration of example model inputs and example states that may be determined by applying inputs to a model.

FIG. 3A is an illustration of an example timeline associated with a patient.

FIG. 3B is an illustration of an example schedule of a caregiver and a child patient.

FIG. 3C is an illustration of a wake/sleep state of a patient.

FIG. 3D is an illustration of determination of availability (or convenience) of a patient to participate in an intervention, based on other states.

FIG. 16 illustrates various inputs that may be employed in decision-support application/functionality.

DETAILED DESCRIPTION

Figure 1:
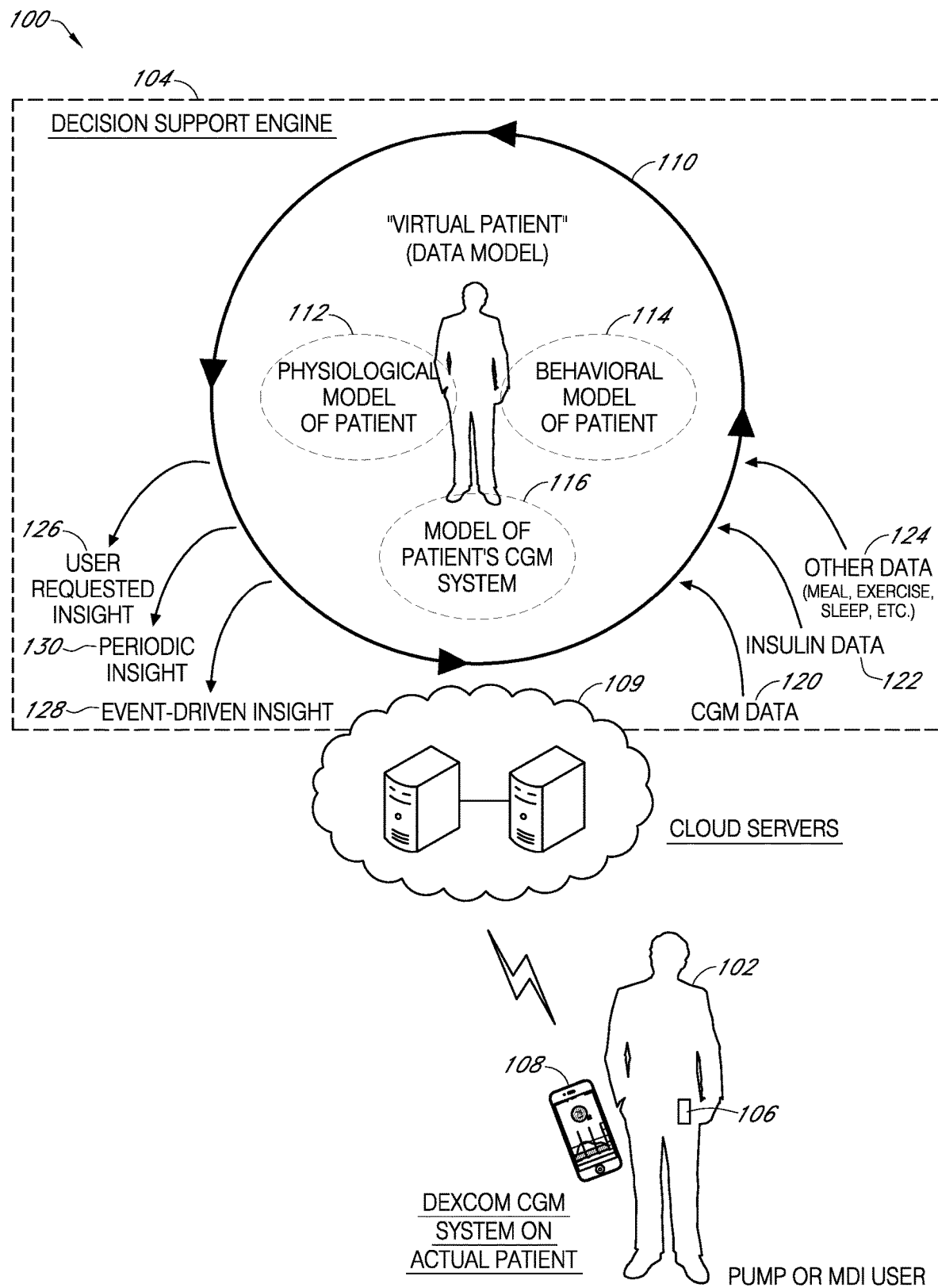
FIG. 1 illustrates an example system for delivering guidance to a patient.

Management of diabetes can present complex challenges for patients, clinicians, and caregivers, as a confluence of many factors can impact a patient's glucose level and glucose trends. The present inventors have recognized, among other things, that intensive insulin users can benefit from real-time guidance that is determined or delivered at a time that is calculated to be useful for a patient or caregiver. The determination of timing of such guidance may be supported by technological systems that process data and patterns to determine timing. For example, by employing technical tools such as sensors, data models, and patient interface devices, a system may determine a time that is calculated to be within a time window when the patient or caregiver is likely to be available to receive and act on the guidance, or otherwise find the guidance useful. In some examples, a system may learn user preferences or behavioral traits or patterns and use the preferences, traits or patterns to determine the timing of guidance. By delivering guidance at a time calculated to be useful to the user, management of physiologic glucose levels may be improved.

Overview

A system that determines guidance and a time to deliver guidance that is calculated to be useful to a user (e.g., patient, caregiver, or clinician) may help a user sleep better, for example to get uninterrupted sleep because glucose levels are controlled, or to go to bed with peace of mind and avoid highs and lows while sleeping, or to know what to do to improve sleep by acting on pre-sleep guidance, or to know when there are potential problems that need to be addressed. The system may alternatively or additionally help a user eat better, for example by having confidence that a patient can, with guidance from a decision support system, eat and stay in range after eating, or stay in range through and after a meal regardless of what the patient has done leading up to a meal, or feel secure knowing that treatment is safe and effective. The system may alternatively or additionally help a user live better (e.g., increase quality of life), for example by knowing when the user needs to pay attention to diabetes issues (e.g., glucose levels), or to adapt to unexpected events during the day and maintain glucose levels under control, or to be aware of a potential or likely excursion ahead of time to enable time to react, or to respond to an excursion without overcorrecting or overeating (e.g., over-consuming carbohydrates.)

In some examples, delivered guidance may assist patients, caregivers, or healthcare providers improve lifestyle or clinical/patient outcomes by meeting a variety of challenges, such as overnight glucose control (e.g., reduce incidence of hypoglycemic events or hyperglycemic excursions), glucose control during and after meals (e.g. use historical information and trends to increase glycemic control), hyperglycemia corrections (e.g., increase time in target zone while avoiding hypoglycemic events from over-correctio), hypoglycemia treatments (e.g., address hypoglycemia while avoiding "rebound" hyperglycemia), exercise, and other health factors. A system may provide therapy optimization tools that learn a patient's physiology and behavior and calculate guidance to help the patient identify optimal or desirable therapy parameters, such as basal insulin requirements, insulin to carb ratios, correction factors, or changes to insulin sensitivity due to exercise. Decision support tools may, for example, help a patient respond to a problem in real time by predicting hypoglycemia or hyperglycemia events or trends, providing treatment recommendations to address occurring or potential hypoglycemia or hyperglycemia events or trends, and monitor how the glycemic, physiologic, or behavioral response in real time. This type of calculated guidance and support may relieve the cognitive burden on the patient, caregiver, or health care professional.

Physiologic sensors such as continuous glucose monitors can provide useful data that may be used by a patient, caregiver or health care professional to manage glucose levels, but the data may require significant processing to develop effective strategies for glucose management. The sheer volume of data, and recognition of correlations between types of data, trends, events, and outcomes, can far exceed human capabilities for processing. This is particularly impactful when a decision about therapy or response to a physiologic condition is being made in real time. Integration of real-time or recent data with historical data and patterns can provide useful guidance in making real-time decisions about therapy. Technological tools can process this information to provide decision support guidance calculated to be useful for a particular patient in a particular condition or situation at a particular time. Technological tools may also reduce the cognitive burden on human decision-makers by repetitively making calculations throughout the day and determining when guidance is to be delayed or delivered.

A decision-support system may be particularly useful in developing pre-sleep guidance to increase the likelihood that glucose levels are controlled during sleep. For example, a system may use an algorithm or model to determine whether a hyperglycemia or hypoglycemia event is possible or likely and develop guidance, which may for example include a pre-sleep action item such as insulin delivery, eating a food item (e.g., fast carbs, slow carbs, or carbs in combination with protein), or setting an alarm to check a status or check for guidance at a particular time. A system may also use an algorithm or model to provide context sensitive alerts. For example, a system may be aware from human input or sensor input or behavioral patterns that a user is sleeping or about to sleep and take the sleep activity into account in calculating an alert or a time to deliver an alert. In some examples, a system may delay delivery of an alert or guidance (e.g., until a risk condition is satisfied or intervention time window opens) to avoid unnecessarily waking a patient or caregiver. In some examples, a system may calculate a time to deliver guidance (and an alert that may wake a patient or time giver) to increase the likelihood that a less disruptive intervention is available. For example, the system may determine that an inquiry is desired (e.g., check for compression low, or check of fever or blood glucose or other physiologic sensor) or a basal or bolus adjustment is needed, for example to avoid a hyperglycemic event with timely delivery of insulin via injection or pump, or avoid a hypoglycemic event by reducing insulin deliver via a pump to avoid later waking the patient to deliver carbohydrates through food or drink.

A decision support system configured to calculate guidance and timing of guidance may also assist with transitions to new therapies or new environments or progressions of the disease over time (e.g. changes in pancreatic function or fading of a "honeymoon" period of partial functioning of the pancreas, changes in treatment routines for Type II diabetics, etc.), for example by providing guidance about potential outcomes, notifications about when a decision may be required, or guidance about the potential impact of therapeutic interventions or behavioral decisions (e.g., exercise, rest, or eating.)

A decision support system may use a variety of sources of information to determine guidance, such as patterns or other information relating to eating behavior (e.g., number of meals per day, meal size distribution across meals and snacks, size of treatments for hypoglycemic excursions, or the number of repeat treatments for a hypoglycemic event), insulin dose information (e.g., bolus and basal dose patterns, pump settings or injection patterns, number of boluses per day, amount of trend adjustment, pre-meal bolus patterns, behavior around correction boluses, number of correction boluses per day), behavior patterns (presence and accuracy of carb-counting, incidence of action or inaction in response to hyperglycemia or need for a correction bolus, conditions, thresholds or triggers for corrections (e.g., glucose level, combination of trend and level, food or other factors), awareness of insulin on board, timing of insulin, "pre-bolus" patterns before meals and duration thereof, errors in insulin delivery or therapeutic intervention, exercise timing, exercise duration, and exercise intensity, physiological response to activity), physiological factors (patterns in response to insulin or carbohydrates or other foods, tendency to "rebound" to a hyperglycemic state after a low glucose, impact of illness or medication on insulin sensitivity or glucose levels), responsiveness to guidance (time to acknowledge alert or alarm), behavior in response to alert or alarm (e.g., eating or sleeping or exercise), and glycemic outcomes (e.g., percentage of time below one or more glucose concentration thresholds (e.g., below 70 mg/dL, below 50 mg/dL), percentage of time above one or more glucose concentration thresholds (e.g. above 180 mg/DL, above 250 mg/DL), and number of events below or above one or more thresholds), disease stage and/or treatment type (e.g., Type I honeymoon period, Type II prediabetic stage, Type II oral medication stage, Type II basal insulin stage), etc. Additional example inputs are described below.

A decision-support system may communicate or interact with other systems, such as glucose delivery devices (e.g., pumps or smart pens) and other analytical systems.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (HCP, e.g., doctor, physician, nurse, caregiver), who may be using the sensor.

Although much of the description and examples are drawn to a glucose sensor capable of measuring the concentration of glucose in a host, the systems and methods of embodiments can be applied to any measurable analyte. Some exemplary embodiments described below utilize an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. No. 6,001,067 and U.S. Patent Publication No. US-2011-0027127-A1. In some embodiments, the analyte sensor is a transcutaneous glucose sensor, such as described with reference to U.S. Patent Publication No. US-2006-0020187-A1. In yet other embodiments, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1. These patents and publications are incorporated herein by reference in their entirety.

Systems and methods for decision support using lifestyle factors are described in U.S. patent application Ser. No. 15/417,008, entitled "System And Method For Decision Support Using Lifestyle Factors", which claims benefit of U.S. Provisional Patent Application Ser. No. 62/289,825, filed Feb. 1, 2016, both of which are incorporated herein by reference in their entireties.

General Description of an Example System

Delivering of guidance at a time or in circumstances that promote timely action upon such guidance may promote effective diabetes management and reduce the burden of managing blood sugar levels. This may be due at least in part to the relevance of the guidance, or the availability or interest of the patient or caregiver to receive and act upon it. In various examples, real-time data, models or other pattern information, patient input, and other sensors and sources of user-specific information may be used to determine a time to determine and deliver guidance.

An example decision-support system may consider data from a variety of data sources, such as physiologic sensors, historical information, and other information about the patient or caregiver to determine a guidance time calculated to be useful to a user such as a patient or caregiver. The time may be calculated, for example, based on timing factors or patterns, or based upon the occurrence of circumstances, which may be recognized from earlier-observed patterns. The circumstances may, for example, be physiologic, behavioral/contextual, or both. In some examples, referencing known patterns and associated glucose control tendencies, the determining or timing of guidance may be calculated to be useful to a user, in view of the reoccurrence of circumstances similar to the known pattern.

In some examples, an example real-time decision support system and method may provide guidance to a patient in real-time, i.e. at a time that enables the patient to intervene in patient glucose management to avoid an undesirable glucose level or trend, and at a time that is calculated to be useful to the patient. The timing of delivery of such real-time guidance may be determined, for example, using information from a calendar, physiologic sensors, or contextual sensors such as GPS or wireless connections, so that the guidance may be is delivered at a time calculated to make real-time intervention possible or convenient for the user.

An example real-time decision support system may include a source of real-time information about a patient, such as a continuous glucose monitor ("CGM", further described below). A continuous glucose monitor may provide information about a glucose level of a patient ("CGM data") at periodic intervals, such as once a minute or once every five minutes, or upon request. The information may be pushed out by the CGM, or may be pulled by an external device, e.g. by a smart phone or other hand-held device that is held or swept over a sensor.

An example real-time decision support system may also include a processing system that receives CGM data and other information such as insulin delivery, caloric consumption, activity, wellness or sickness status, and other sensed or user-entered information about the status, environment, behavior, or wellness of the patient. CGM data and other data may be combined and processed to develop guidance for delivery to the patient. The guidance may be developed based upon timing factors, such as timing of insulin delivery, calorie consumption, type of calories consumed, information about absorption or digestion times for food or beverage types or quantities or combinations, exercise timing and post-exercise oxygen or calorie consumption, and patient availability or convenience to participate in intervention, such as insulin delivery or delivery change or exercise or a dietary change.

Models

In some examples, a model may be constructed to process CGM data and other information. The model may, for example, be a state model. One or more states may be determined by applying one or more inputs to the model. States may be predefined, or may be learned from analysis of data, or both. In some examples, decision support system may be driven by combining the output of at least two models: (1) a physiological state model, and (2) a behavioral or contextual model. In some examples, decision support may be driven by at least three models, e.g. 1) by a physiological model and separate behavior and context models, or 2) by a physiologic, a behavioral/context model, and a measurement model (further described below). Other variants with larger numbers of models and sub-models are also possible.

Physiologic Model

In some examples, a physiologic state of the patient may be determined by applying one or more inputs to a physiologic model. One or more physiologic states may be used to determine patient guidance, the timing of guidance, or both. For example, one or more inputs (which are described in detail below, e.g. see FIGS. 2B, and 14-16 and description thereof), may be applied to a model, or a plurality of models, to determine a physiologic state that a patient is in. The physiologic state may, for example, include as a glucose concentration level (e.g. blood glucose level or glucose concentration in other body fluids such as interstitial fluid), a falling or rising glucose concentration level (i.e., glucose trend), or a rate (e.g. slope or higher-level derivative) of a falling or rising glucose concentration level. A determined physiologic state may also be or include activity level (e.g. exercise detected from an accelerometer, heart rate sensor, or respiration sensor), metabolic drive (e.g. glucose consumption rate), and insulin resistance (e.g. in response to stress hormone secretion, sickness, or high blood sugar levels), insulin sensitivity (discussed in greater detail below), insulin on board, insulin time to action, insulin action time, and carb to insulin ratio. Other physiologic states are possible.

Behavioral or Contextual Models

Behavioral or contextual models may be related and may in some examples be combined into a single model. A behavioral model may relate to decisions of a user, whereas a contextual model may relate to a user's environment (e.g., a location). In some examples a behavioral model may include contextual aspects (e.g., location may be considered a subset of behavior, as a user's location is typically a result of a user's choice). In other examples, two separate models may be provided to account for behavioral and contextual factors.

In some examples, a behavioral or contextual state may be determined by applying inputs to a behavioral model. The behavior or contextual state may be used to determine guidance, the timing of guidance, or both. A behavioral or contextual state (e.g. unavailable, or worried about hypoglycemia) may be determined by applying inputs to the behavioral or contextual model. The inputs to the behavior model may include a determined physiologic state. Other inputs to a behavioral or contextual model may include user-provided input, real-time parameters (e.g., clock values), measurement data or sensed data, calendar information, stored pattern information (e.g. inputs or states correlated to time), or outputs from other models. User-provided input to a behavioral or contextual can include, in some examples, an indication of the host's course of treatment and/or disease stage. Additional inputs are described below and illustrated in FIGS. 2B and 14-16. In some examples, a behavioral model may include contextual aspects. In another example, the contextual aspects may form another model.

Measurement Model

A measurement model may at least in part assess or confirm the reliability of one or more measurement inputs, such as CGM data or information from a CGM model, blood glucose meter data (e.g. from a finger-prick sensor) received via a user interface or from a smart meter (e.g., configured with communication capability to send or transmit values), measured blood glucose dosing information (e.g. dosage information received from an insulin "smart" pen configured to track and communicate dosing information), insulin dosing information received from a pump, or insulin data entered by a user via a user interface (e.g. volume of insulin injected via needle or pump). A measurement state obtained from the measurement mode may be provided as input to another model.

Determination of Guidance and Timing

A decision support engine may determine guidance for a user (patient or caregiver such as parent or clinician) and a timing for determination or delivery of the guidance, based at least in part on one or more model states, and may provide guidance to a user via a user interface, such as through a mobile device. The decision support engine may provide "real-time" guidance based on recent information (e.g., recent CGM data) that the user may use to affect a blood glucose level trend (e.g. avert a high or low glucose concentration trend or level.)

Use of Machine Learning to Determine States and Guidance

In some examples, a machine learning method may be used a-priori to identify possible states. In other words, a universe of possible states may be deduced from a set of data. For example, a "post-activity state" may be identified as a state of increased insulin sensitivity up to a certain period of time (e.g., 8 hours) after exercising. Then in real time, the system may use real-time exercise data (e.g., activity data, heart rate, or respiration) to see that the user is entering such a state, and thus provide guidance that the user take less insulin than usual, due to the increased insulin sensitivity. Machine learning may also be used to identify sets of input variables that lead to a consistent insulin sensitivity model that can be applied when in that state. In another example, machine learning techniques may be used to determine that a patient always ignores alerts during certain times of day (e.g. the hours of 3-5 PM), and thus the system may turn off non-essential alerts during those times, and trigger a risk report as guidance right before the period of time (e.g. shortly before 3 PM), or deliver advance alerts to the user to prepare the user for the period of time in which alerts tend to be ignored.

Example System

FIG. 1 shows an example system 100 for determining guidance and timing of guidance using sensor input and a model. The system may process physiologic inputs, e.g., inputs relating to management of glucose concentration levels, to determine a time that is calculated to be useful to the patient or other user for determination or delivery of guidance.

The system 100 may include a decision support engine 104 that may process information about a patient (e.g., received real-time sensor data) and combine the sensor information with patterns, e.g. temporal, physiological, or behavioral patterns, or combinations thereof, to produce outputs that may be provided as guidance, or processed to develop guidance. The decision support engine 104 may produce a variety of outputs, which may be provided to the patient 102 as guidance via a user interface 108, or may be used to determine guidance, or may be used to determine the timing of guidance. The guidance may, for example, include diabetes therapy guidance.

Example Inputs

Example Implementations of the Decision Support Engine

One or more sensors 106 may be associated with the patient to provide information about the patient to the decision support engine 104. The sensor 106 may, for example, include an analyte sensor such as a glucose sensor as described above. The sensor 106 may be a transdermal sensor, a body fluid sensor such as a contact lens sensor or dermal sensor, or an implantable sensor configured to measure qualities of interstitial fluid or blood. For example, the sensor 106 may be a subcutaneous, transdermal, transcutaneous, non-invasive, intraocular and/or intravascular glucose sensor, as described above. In some examples, the sensor may be a wearable or implantable sensor that is connected to the patient 102, such as a continuous glucose monitor sensor available from Dexcom™, Abbot™ (e.g., the Libre™ sensor), or Medtronic™ (e.g. the Enlite™ sensor). Other types of sensors may also be associated with the patient, such as a heart rate sensor, respiration sensor, other types of analyte sensors, motion sensor (e.g. accelerometer), posture sensor (e.g. 3-axis accelerometer), or acoustic sensor (e.g. to capture ambient sound or sounds inside the body). Sensor 106 may be wearable, e.g. on a watch, glasses, contact lens, patch wristband, ankleband, or other wearable item, or may be incorporated into a handheld device (e.g., a smartphone), or may be incorporated into another sensor, such as a continuous glucose monitor sensor. In some examples, the sensor 106 may include a multi-sensor patch that may, for example, detect glucose levels, heart rate, respiration (e.g., using impedance), activity (e.g. using an accelerometer), posture (e.g. using an accelerometer), galvanic skin response, tissue fluid levels (e.g. using impedance or pressure). In some examples, an array or network of sensors may be associated with the patient. The one or more sensors 106 may communicate via wired or wireless (e.g., Bluetooth® wireless communications technology, Zigbee® wireless communications technology, Z-Wave® wireless communications technology, NFC) communication with a local device 108, which may, for example, be a mobile device such as a smartphone. A system may learn the joint distribution of signals from varied sensors (e.g. from sensors on a multi-sensor patch, or from networked sensors or a group of sensors. The system may use the historical data or knowledge of the joint distribution of signal (e.g., how sensor signals relate to one another or move together) to A) determine or impute (e.g. using a model, algorithm or calculation, as further described below) missing sensor data points, or B) to predict future blood glucose concentration levels, or C) to detect sensor failures or problems with performance of a CGM sensor based on joint signals recorded in real time and historical information, or D) to estimate the number of carbohydrates, fat, protein or other substance ingested based on sensor information, or any combination thereof.

The decision support engine 104 may receive sensed information 120. The sensed information 120 may, for example, include physiologic data such as CGM data from a CGM sensor, activity data (e.g. from an accelerometer), heart rate, or any of the other physiologic described herein. The sensed information may be sensed by the one or more sensors 106, the local device 108, or other sensor device. The sensed information may also non-physiologic data, such as location information (e.g. GPS) or connectivity information (e.g. Wi-Fi®).

Input to the decision support engine 104 may also include insulin data 122. Insulin data may, for example, be captured from an insulin delivery device such as a pump or may be received from a smart pen that is configured to track insulin delivery and communicate insulin delivery information to the system, e.g. via wireless communication to a smart device that may relay the information to the decision support engine. Insulin data may also be received from a user, e.g. from a patient or caregiver through a user interface on a smartphone or other computer device.

The decision support engine 104 may also receive other information 124, such as meal information, sleep information, or calendar information, which may include sensed information (e.g. sleep detected using an accelerometer or physiologic sensor), learned information (e.g. temporal patterns), or information supplied from a user via a user interface (e.g. meal or schedule information). Additional inputs that may be received by the decision support engine 104 are described in reference to FIGS. 2A, 2B, and 14-16. Additional details on example system components are described in reference to FIGS. 23-24. Meal or carbohydrate information may be received via a user interface on a device (e.g. smart mobile device) that is paired with a CGM or may be received from a different application or different device (e.g., carbohydrate information may be pulled from a health app or an app or device associated with a pump.)

Example Implementations of the Decision Support Engine

The decision support engine may include one or more models 110. The one or more models 110 may, for example, include a state model. In an example, a "virtual patient" model may include known information about the patient, which may be based on a template model formed from known factors or derived from population data, or may be learned from information about the patient, or a combination thereof. The model may, for example, reflect physiological information and behavioral information. Physiological information may include, for example, factors such as glucose or insulin sensitivity, response to physical activity or stress, illness, fatigue or rest, growth rate (e.g. in children), or basal metabolism. Behavioral information may include, for example, factors such as ingestion of food or drink, exercise, administration of insulin, schedule, e.g. as described by calendar appointments, interest in guidance. In a state model, factors such as these may be represented as states, which may be discrete (e.g., high, medium, low) or continuous (e.g., determined by a function). The one or more models 110 may include a pattern, which may, for example, include a physiological pattern, a contextual pattern, or a behavioral pattern, or a combination of these patterns. A physiological pattern may, for example, be based on a physiology model.

In some examples, two or more models may work together to determine guidance. For example, a physiological model 112 and a behavioral model 114 may interact to determine glucose management guidance that accounts for both the patient's physiology and the patient's behavior. In some examples, the output of one model may be an input to the other model. In various configurations, the models 112, 114 may be independent, or the models may be sub-models of the model virtual patient model 110. In some examples, the models may also interact with a measurement model 116, which may for example be a continuation glucose monitoring model. The measurement model may include factors such as sensor accuracy, calibration factors, time since insertion, time since calibration (for systems that use calibration), sensor status (e.g. failed sensor or sensor presence), or communication status (e.g. signal loss).

In various examples, the decision support engine 104 may reside on a remote resource 109, a local device 108, or a combination thereof (e.g. a "hybrid configuration"). The decision support engine 104 may reside on or be connected to one or more remote resources 109 (e.g. cloud servers) by a network, such as a cellular network, Wi-Fi® network, the internet, or combinations thereof. The cloud servers 109 may collect and store information received from sensor 106. The cloud servers may also collect other information, such as user calendar information, e.g. information received from a calendar of a patient or patient caregiver. In some examples, the decision support engine 104 may reside on a device near the patient, e.g. the local device 118. In some examples, the decision support engine 104 may reside on a local device but receive assistance or periodic updates from a remote system. In a hybrid configuration example, the decision support engine 104 may be distributed between the local device 108 and a remote system, e.g. initial processing may be conducted on a local device (e.g., smartphone), with more complex processing requests routed to a remote resource that may have higher processing power. A hybrid configuration may maintain or improve the performance of the local device 108, by avoiding overloading the local device with excessively complex processing tasks. A hybrid configuration may also improve the performance of the system, as some tasks may be performed quickly and without network access by the local device 108, yet more complex tasks may still be possible by leveraging the larger processing power of a remote resource 109.

As a practical matter, it may also be desirable to avoid overloading remote resource 109 with requests from a multiplicity of patients. In an example, the local device may send data to the remote resource 109 periodically (e.g., in real time or on a schedule or when a connection is available, or any combination thereof), and the remote resource may periodically assess the data for a particular user, such as once per hour or once per day. The remote resource 109 may, for example, examine the received data, or a data set augmented with or containing the received data, to look for problems or potential insights. The remote resource 109 may, for example, update a model to reflect or account for the new data. In various examples, the remote resource may send an update (e.g., pushed by the remote resource 109 or as requested by the local device 108) to the local device to address a problem, insight, or model update learned from the new data or augmented data set.

Example Determination of Timing of Guidance by the Decision Support Engine

The decision support engine may process the various inputs, e.g. apply the inputs to one or more models, and determine a time for guidance that is calculated to be useful to the user. In various examples, the timing of guidance may be calculated to enable a user to improve a user's sleep experience, eating experience, or quality of life. For example, the system may identify a potentially problematic pattern, and determine a time to deliver guidance, where the guidance delivery time is calculated to avoid interrupting sleep, or to maintain blood glucose control while providing the user with flexibility in meal selection or timing, or to provide sufficient advance-notice of a potential problem (e.g., high-glucose excursion or low-glucose level) so that a user can adapt the behavior of the user or react to the problem in a timely manner.

In an example, the system may promote healthy or uninterrupted sleep by determining that a problem is likely to occur at a time when a user is likely to be sleeping (e.g., 2 AM) and calculating a time to deliver guidance when the user is likely to be available (e.g., 9 PM). The system may recommend an action, such as eating a pre-sleep snack to avoid a night-time low, to avoid the need to wake the user during the night. In an example, the system may receive a glucose value and determine, based on a learned model of the patient, that the patient will likely have a hypoglycemic event when the user (caregiver or patient) is likely to be sleeping, and determine guidance and a time to deliver the guidance to avoid interrupting sleep of a patient or caregiver.

In another example, the system may determine a pattern in nighttime blood glucose concentrations levels or trends and delivery guidance to change a behavior or therapy. For example, the system may recommend a basal dose increase if the system detects a pattern of glucose levels rising through the night so that the glucose concentration level or trend satisfies a condition (e.g., over a specified value (e.g. 130 mg/DL or a change over a specified amount (e.g. more than 30 or more than 40 mg/dL increase during sleep or during a specified period associated with sleep (e.g. 12-5 AM))). In another example the system may recommend a basal dose decrease when the system detects a pattern of glucose concentration level decreasing a specified amount or rate otherwise satisfied a condition.

In another example, the system may support meal-time decisions by delivering guidance calculated to be useful in maintaining blood glucose control while providing a user with flexibility in decisions about what and when to eat. In an example, the system may determine that a glucose level is likely to trend high before a meal time and determine a time to deliver guidance about a correction bolus before the meal to avoid a need to delay eating when the meal time arrives. For example, the system determine that a user should "pre-bolus" a specified amount of time before a meal (e.g., deliver insulin 20 minutes before commencing eating), and the system may determine a time to deliver the guidance to deliver the bolus so that a meal can begin at a planned time, or a time that aligns with a learned pattern. In some examples, the length of the pre-bolus window (amount of time between delivering an insulin bolus and commencing eating) may be determined by the system, and the timing of guidance may be calculated to afford the user time to accommodate the calculated pre-bolus window. For example, the system may determine that a 30-minute pre-bolus is needed to affect a high glucose level before a patient eats the next meal. In an example, the system may deliver guidance 30 minutes before a scheduled meal to prompt a user to deliver the pre-bolus. In another example, the system may provide additional time for the user accommodate the pre-bolus, e.g. the system may determine that pre-bolus guidance be delivered 60 minutes before a meal to allow the user 30 minutes advance notice of the need to deliver a pre-bolus 30 minutes prior to eating.

In another meal-time example, the system may calculate a time to deliver guidance during or after a meal. For example, the system may determine that insulin is rising faster than normal and may determine that guidance should be given to deliver an additional dose of insulin. In an example, the system may calculate a time to deliver guidance to optimize glucose control. For example, the system may determine that guidance should be given during a meal to deliver additional insulin. In another example, the system may calculate a time to deliver guidance so as to avoid interrupting a meal. This may be accomplished, for example, by reference to a user calendar, or based upon a pattern of behavior (e.g., average meal time), by use of a physiologic sensor (e.g., an activity sensor), or through use of location information (e.g., detecting that a user has left a restaurant.)

In some examples, the system may be designed to improve a patient or caregiver's quality of life by calculating a time to deliver guidance to provide sufficient advance-notice of a potential problem (e.g., high-glucose excursion or low-glucose level) so that a user can adapt the behavior of the user or react to the problem in a timely manner. For example, the system may determine that an excursion (e.g., high-glucose trend) is likely to occur and determine a time to deliver guidance that allows the user to deliver take corrective action (e.g., deliver a correction bolus, or exercise) to counter-act the likely excursion. In some examples, the system may calculate and/or predict times to deliver guidance, to enable a user to focus on other activities and anticipate delivery of guidance. For example, the system may deliver guidance every two hours during the day. In some examples, the system may determine a recurrent schedule to deliver guidance. In some examples, the system may deliver guidance regarding the need for a user's attentiveness to glucose management. For example, the system may calculate a probability of the need for user intervention (e.g., determine the risk of a blood glucose concentration level moving out of a specified range), and notify the user when a condition is satisfied (e.g., when the probability exceeds a threshold). In some examples, the system may periodically notify the user that no intervention is required (e.g., "Looking good: Glucose levels are well controlled".)

In some examples, the system may deliver guidance about when to check the system for further guidance. For example, the system may receive meal information, such as meal content and an anticipated or actual (present or past) meal time and advise the user to check back for further guidance in a specified amount of time, e.g. "Check back for further guidance in 30 minutes." In another example, the system may deliver pre-sleep guidance, and ask the user to check back after a pre-sleep activity has been completed, e.g. "Eat a small snack and check back 10 minutes after eating."

In some examples, the timing of guidance may be calculated based in part on user-defined preferences, such as a preference about whether the user wants to be interrupted during a meal, or the conditions under which the user want to be interrupted, or time periods during which the user prefers to be interrupted or prefers not to be interrupted.

In some examples, the timing of guidance may be provided related to a current user activity based upon real-time data and patterns learned from past activity. For example, to determine a useful time to deliver guidance, the system may integrate real time physiologic data (e.g. CGM datum) with known physiologic and behavioral patterns (e.g., a model) to determine both the nature of the guidance, and the timing of the guidance. The system may, for example, learn a glucose response after a particular meal. When real-time data suggest that the user is going to eat the same meal, or a similar one (e.g., as determined from GPS information or Wi-Fi® connection to a restaurant), an insight may be delivered based on the pattern learned from past activity. In other example, real-time data may suggest that a user is going to bed, or has a meeting coming up, and such data may be used to determine a time to deliver guidance, e.g. the real-time information may indicate that decision-support should be given soon, or sooner than it would otherwise be given, to avoid interrupting an upcoming activity (e.g., sleep or a meeting).

In some examples, the timing of determination of guidance may balance the need for data to determine a state with the need for timely action and a need to avoid unnecessary or excessive interruptions to the patient. Generally, as more time passes, more data are available to use to obtain a curve fit against a pattern or to apply against a model, which may drive more accurate conclusions about states, probabilities, or the appropriate guidance. For example, four hours after eating, most of the data regarding the body's response to a meal are known. But after one hour, while the full response is not yet known, it is generally discernable approximately how much the user ate, or whether the insulin delivered is appropriate for the consumed meal. After two and a half hours, these determinations can be made with even more accuracy. In some cases, the user may administer a correction bolus, or the user may be told to eat more, e.g., because the patient did not consume as much as the patient thought the patient did, and the patient may now be in danger of trending to low glucose levels. This additional information about food intake or insulin administration may also be processed by the system. In this example, a timing for delivering of guidance may be determined based on information that becomes available after eating. This may include one or more of the food consumption information, insulin information, glucose level information, other physiology information (e.g. activity), and known physiologic patterns (e.g., from a physiology model). Timing may also be based upon user preferences (e.g., preferences about the frequency or timing of alerts, e.g. alert often/less often or alert early/late or alert according to a prescribed or learned schedule), which may be learned from data (e.g., as states) or entered as user input.

Returning to the post-meal example described above, somewhere between the time that the user eats the meal and the time an alert is triggered, it may be determined when to trigger an alert. This determination may take into the fact that if the alert is delayed, e.g. the system waits to determine guidance or delivery of guidance, the guidance, or underlying states from which guidance may be determined, will likely increase in accuracy as time passes. But if the system waits too long, an optimal or desired window of opportunity for delivering guidance and administering therapy may have passed, e.g., an undesirable glucose trend or insulin sensitivity level may develop while the system waits for data to accumulate. When glucose levels rise beyond a normal range, a patient's body tends to become insulin resistant, which may make it more difficult to return the glucose levels to a normal range using insulin, and thus may require a larger dose of insulin. The larger dose of insulin may increase the risk of the patient trending to low glucose levels when the insulin resistance (and high glucose level) is eventually overcome. On the other hand, when glucose levels trend too low, the administering of glucose may come too late, or may lead to an over-reaction by the patient (e.g., administering too many fast carbs) or the patient's body (e.g. glycogen release by the body), which may then lead to high glucose levels (sometimes referred to as the Somogyi effect). In more extreme cases, an acute risk may develop, and alternative options such as administering glucagon may be required. In the severe case, the patient's ability to administer or participate in following guidance may diminish, as the patient may lose cognitive capacity or consciousness with very low glucose levels.

User convenience may also be accounted for in determining the timing of guidance. For example, when it is known that a user is going to go in a meeting in 2 hours, the system may provide an alert prior to the meeting, even if the determined states or guidance are less accurate than would ordinarily be accepted (e.g. an optimal balance of data accumulation and risk avoidance has not been achieved), to avoid interrupting the user during the meeting or to assure that the guidance is delivered at a time that an intervention can be administered. In some examples, when the user is going into a situation where the user does not want to have to respond to an alert, the system may provide an option to receive an alert early even if the alert or guidance may be somewhat less accurate, e.g. via a one-time user input or adjustment of a user-controlled setting, which may correlate or interact with a calendar. For example, or when the system knows or has access to the calendar of the user, the system may on its own provide such prompts and options ("Would you like an early alert before your weekly Tuesday afternoon meeting"). In another example, the system may receive a request from the user (e.g. in the form of a user-requested insight, as further described below).

In some examples, a state model may be used to balance urgency and inconvenience factors. For example, states may include risk levels, or probabilities of transitioning to an undesirable state (e.g. risk or probability of trending to a blood glucose level below 40 mg/DL or above 180 mg/DL), and the system may control determining or delivery of guidance to maintain risks levels or probabilities within specified parameters, while avoiding inconvenient notification times when possible.

The system may also account for user sleep schedules. For example, when it is known that the user is going to bed within four hours of having a meal, but the glycemic response to the meal is not yet known, the system may provide guidance to do something before going to bed to improve the situation or avoid a risk of trending to an undesirable state or glucose level. For example, the system may deliver pre-sleep guidance to administer a correction bolus, or make a basal adjustment, to avoid a sustained high glucose level or a trend to a high glucose level, or to avoid waking the user for a night-time intervention. In another example, the system may deliver guidance to have a snack before going to sleep to mitigate a risk of a low glucose level.

Example Outputs—Forms of Guidance

Example Outputs—Forms of Guidance

Guidance output from the decision support engine 104 may include, for example, text (e.g., "Watch for an unexpected low glucose level"), sounds (e.g. tones or spoken), or graphics or animations, such as a predicted or actual insulin graph, or a probability cone, which may show the range of possible outcomes from a contemplated or consummated action, such as exercise, food consumption, or insulin delivery, or a combination thereof. A probability cone may show a range of potential outcomes over time; the range of outcomes broadens over time, i.e., a wider range of options becomes possible (or may satisfy a statistical condition). The guidance may include alerts, recommendations, or other useful information.

In some examples, a guidance recommendation screen may show factors included in determining guidance and may allow a user to adjust assumptions or weighing applied to each factor. For example, an interactive recommendation may include an action to deliver four (4) units of insulin in the next 15 minutes and the set of factors used in the decision (pasta has 40 g carbs, patient activity level after lunch is normally moderate, current glucose level is normal but falling). These factors can then be adjusted by the user if the assumptions need modifying. In some examples, CGM insulin and meal/carb data may be post-processed to determine best possible insulin control. In some examples, the system may intentionally introduce a time-limited bias to reflect pending changes that are or were occurring or could occur. For example, the system may intentionally skew blood glucose levels low, for a limited time, right after dosing insulin to reduce the likelihood of overcorrection.

In various examples or guidance decision-support requests may use text, email, app notifications, phone calls, or other forms of communication. In some examples, the best mode may be selected by the user or by the system based on the context. For example, the system may use voice while the patient is driving but watch messages when the patient is in a meeting. In some examples, guidance and decision-support requests may be voice enabled using automatic speech recognition and natural language understanding, Various types of guidance insights are possible. For example, the guidance output may include, for example, an event-driven insight 128, a user-requested insight 126, or a periodic insight 130. An event-driven insight 128 may include, for example, a time, context, or physiologic event-driven insight that is driven by an underlying algorithm identifying a decision point, such as a useful time to deliver actionable guidance. A user-requested insight 126 may include, for example, a user request for guidance about a particular therapy decision at a particular time, e.g. insulin delivery before a meal or in anticipation of an event such as a meeting, physical activity, or sleep, and the decision support engine 104 may provide guidance in response to the request. Such guidance may include, for example, a recommended basal or bolus insulin dosage or scheme, or an amount of physical exertion, or a plan to monitor or intervene at a particular time or time range. A periodic (non real-time) insight 130 may summarize a pattern over multiple days, meals, or treatment decisions. For example, a periodic insight may include a retrospective summary at the end of a period of time such as a day, week, month, or quarter, a post-workout summary, a summary after a period of time (e.g. number of hours, or morning or afternoon or night), or variants thereof.

Example event-driven insights 128, user-requested insights 126, and periodic insights 130 are described in further detail below.

Event-Driven Insights

A time, context, or event-driven insight may be driven by determined states or state transitions, physical events, location, a timing pattern (e.g. a calendar), or any combination thereof. For example, an insight may be triggered at least in part by a physiologic event such as a pattern of glycemic events, which may for example include a rapidly falling glucose level after a meal or during exercise, or a rapidly rising glucose level (e.g. after a meal or snack or stressful event).

An insight may take the form of a personalized guidance message that has particular relevance to a presently-occurring event or pattern. The personalized guidance message may be based on information that is learned about the patient, which may be embodied or reflected by one or more models of the patient. In an example, a system may detect patterns that precede hypoglycemic and hyperglycemic events and alert the user with enough time to take action. In another example, a therapy adjustment may set a context-driven alarm: for example, when a therapy adjustment is made, such as an increase in basal rate, which may be determined to increase the risk of a night-time low glucose level, a low-glucose alert may be made more sensitive at night for a specified period of time, such as the next two weeks, or a personal guidance message reminding a user of the potential for a low night-time glucose level may be delivered each night, or more frequently or under a broader set of conditions than prior to the adjustment. In another example, it may be determined that a treatment decision or therapy event (e.g. forgetting to dose insulin before a meal, e.g. missed "pre-bolus") may justify increased vigilance (e.g. checking of CGM data or awareness of a potential need to deliver therapy) during a time window following the decision or event, which may be communicated via a guidance message, or during the window a guidance message may be delivered under a broader set of conditions (e.g. lower threshold for providing event-driven guidance). In some examples, event-drive alerts may be set based on cumulative glycemic risk or glycemic exposure, e.g. food or caloric or carbohydrate consumption may be tracked and an insulin/glycemic imbalance may be detected, which may be communicated via personal guidance ("Your food or beverage consumption may have exceeded expectations") or may form the basis for a personal guidance message ("You may need more insulin based on eating or drinking patterns.") In some examples, a personal guidance message may provide a range of choices that are stratified by risk and rewards.

In some examples, the decision support engine may determine a bolus recommendation (meal bolus or correction) and determine a time to determine the recommendation. The timing of the determining of the bolus and delivery of the guidance may be calculated to balance the need for guidance with an interest in avoiding interruptions to the patient/user and a need for sufficient data to accurately determine bolus information. In an example, manual inputs and learned or planned inputs (e.g. meal information) may be fed into a bolus calculator. The bolus calculator may be a general one, or may be personalized, e.g. specified to the user's current diabetic state. The bolus calculator may output a dose recommendation, and the system may then observe glucose levels after the user administers the recommended dose. Based on historical data, a typical glycemic response may be known for a particular situation, which allows for a comparison of real-time data with historical data or a pattern derived from historical data. For example, if the user eats 60 g of carbs and takes a specific amount of insulin, the resulting glucose levels and trends that occur after time may be known from the historical data or pattern (e.g. 120 mg/dL glucose level 30 minutes after eating, and rising slowly (e.g., 2 mg/DL every 5 minutes)). When in a particular case, the user indicates that the user ate a specific meal or amount of carbs (e.g., 60 carbs), but glucose values produce a level or a trend that is different from previous profiles (e.g. 160 mg/dL glucose level and rising steadily (e.g., 10 mg/dL every 5 minutes)), the system may then inquire with the user to obtain corrected meal information, or determine how many carbs the user actually ate based on the glucose signal and present guidance or an inquiry ("Did you eat something else?" or "Did you not eat the chicken?"). The system may also account for absorption rates (e.g. fast carbs such as foods with large amounts or refined sugar vs. slow carbs such as pasta) and the presence of other foods, such as protein or fat, that may affect the glucose trend, such as slowing the absorption rate of carbohydrates consumed with the protein or fat.

In an example using state models, a patient state may initially be in a first state (e.g., eating 60 carbs), and the system may afterward determine that the patient is in fact in a different state (e.g. eating 90 carbs). In another example, a patient state may initially be in a first state (eating 60 carbs), and so the patient receives a dose accordingly, but the patient state is later determined to be in state with a carb counting error of X (e.g., 30 grams carbohydrate), and in this case the system may provide decision support guidance, e.g. a correction bolus, to avoid a low or high.

In some examples, a time to deliver guidance regarding the correction bolus may be determined using a physiology model, behavior model, or both. For example, a range of acceptable times for delivery of a correction bolus may be determined using a physiology model, and a range of convenient times for delivery guidance or a correction bolus may be determined using a behavior model, e.g., using learned pattern information, or using a calendar that shows meeting schedules or a class schedule, so that guidance may be timed for delivery between classes or meetings, or near the end of a meeting or class.

User-Requested Insights
User-Requested Insights

A user-requested insight may include, for example, receiving input from a user (e.g. through a smartphone app) for decision support for an impending diabetes decision, such as "how much insulin should I bolus before this meal?" or "should I have a snack before I go for a bike ride?" In an example, a personal guidance response may include an interactive recommendation (e.g., "Deliver 4 units of insulin") and may also optionally include the set of factors used in the decision (e.g., "The portion of pasta has 40 g carbs, your activity level after lunch is normally moderate, and your current glucose level is normal but falling"). In some examples, the factors can may then be adjusted by the user (e.g. to arrive at a different dose) if the assumptions need modifying.

In some examples, a prior user-requested insight may be used as an input to a model, and the model may learn or adapt to the circumstances when a user is likely to request insight. This information may be integrated into the model and decision-support engine, so that the system may provide personalized guidance in the circumstances and time that a user is likely to need the guidance, e.g. anticipate a request and proactively provide guidance to the user. For example, if a user frequently requests guidance before embarking on a weekly bike ride (e.g., as determined from learned behavior patterns) or dining at a particular restaurant (e.g., as determined from a patient calendar) or after completing a physical workout (as determined from an activity sensor, associated smartwatch, or calendar), the system may determine that personalized guidance is likely desired at a particular time, and deliver guidance relevant to the present situation or typical pattern. User-requested insights may also be used to educate a model, based upon information implicit in the user request. For example, when a user asks for decision support prior to exercising, the system can glean that the user tends to exercise at a particular time, especially when a series of related user requests are obtained over a time period, which may reveal an exercise timing pattern (e.g. running on Monday, Wednesday, and Friday mornings).

In some examples, the system may receive a user request for decision support for a future activity (e.g., exercise, driving, meal, or sleep), and the system may provide suggested therapy adjustments or preparatory steps as guidance. For example, the guidance may include changes in basal insulin, bolus insulin calculations, and suggested snack amounts (e.g., change your basal rate by x amount before you begin exercising, or eat 15 grams of carbs before you go to sleep). In some examples, the system (e.g. model) may learn from the result of the guidance, and make adjustments specific to the individual, e.g., the system may learn how much exercise changes their glucose. In some examples, patient-specific information, such as basal rates, or insulin-to-carb ratios for specified meals or times of day, may entered by a clinician into an electronic medical record (EMR) system and retrieved by the system and used to inform or educate the model or assist with developing responses to patient requests for guidance.

In an example, the system may receive a user request for pre-sleep guidance. The request may, for example, be received through a decision-support smartphone app. The system may provide guidance regarding one or more actions the user should perform or consider before going to sleep, such as eating a snack, delivering a dose of insulin, setting an alarm clock, or setting an alert setting for a continuous glucose monitor. The system may also provide an explanation of a risk or a reason for guidance. For example, the system may notify the user of a risk of a "late low" glucose level due to an exercise session, or a risk of a low glucose level due to a reported insulin dose that the system estimates was too large for a given meal or set of circumstances, or a risk of a low or high glucose level based upon a trend analysis. In some examples, the system may notify the user of a time or time range that a problem may occur, such as "A low glucose level may occur around midnight." In some examples, the system may suggest that the user re-check guidance (e.g., check a smartphone decision support app for updated guidance) at a later time, which may occur for example when the system determines that additional information (e.g., additional CGM trend data) may be particularly useful in determining guidance, increasing confidence in guidance, or determining an expected event.

In an example, a user may supply a photo of an upcoming meal, or scan a restaurant menu, and the system may provide guidance about an estimated effect on blood glucose or an insulin dosing recommendation. For example, a mobile device (e.g., smartphone) application may be configured to scan a menu and convert the meal items into estimated glycemic impact. In an example, a user may be prompted to position a smart device camera over a menu, and the glucose information for the menu item may be presented on a user interface, e.g. next to a menu item as viewed by a user on a screen. This may be accomplished, for example, using text recognition and a lookup table of glucose values for a particular type of meal or establishment. In some examples, meals that would be considered "healthy" or "unhealthy" may be highlighted, indicated with text or symbols, or otherwise identified on the user interface or, e.g., using augmented reality (AR) where a menu is the subject of augmentation. In some examples, a predicted glycemic impact or excursion (e.g., "72 g. carbs" or "BG>200") or necessary insulin bolus (e.g. 6 units) may be presented. In some examples, a predicted trend graph, or summary metrics such as glycemic load, may be presented. In some examples, a predicted excursion may be personalized by learning from historic data or profiling the patient, and optionally incorporating such information into a physiologic model, so that the impact on glucose is personalized to the patient. In another example, when a proposed workout (e.g. 30 minutes of moderate running, or five sets of dead lifts, or 1 hour of swimming) is provided as input (e.g. entered into a smartphone app), the expected result, such as a glucose profile, may be predicted (e.g. by applying the workout as input to a model) and displayed on the user interface. The result may, for example, be provided as a probability cone to provide the user with information about the potential range glycemic responses.

In some examples, guidance may include a bolus recommendation that may include two numbers to reflect a decision tree, e.g. one bolus number that assumes the user exercises as planned, and a second bolus number that assumes that the exercise is not completed. In some examples, the guidance may include an amount of insulin on board, which may be the amount of insulin determined to be active in the body as determined by predefined algorithm (e.g. based on population-based or theoretical data), or as determined by a model (in which case the insulin on board may be patient-specific). Insulin on board guidance may be provided in response to a user request, or in response to an event, such as a determination that the insulin on board is likely to cause a low glucose level, or a determination that the amount of insulin on board is likely to be insufficient to control glucose levels (i.e., a high glucose level may occur). In some examples, guidance may reflect a preset or user-defined goal, such as a predefined blood glucose range (e.g., 70-150 mg/dL range) or a percent of time that the glucose level is in a defined range (e.g. 80% in the 70-150 mg/dL range). For example, the guidance may include a suggested modification (e.g. afternoon exercise or an insulin dosage change) to move the user toward the goal.

In another example, input from a user may initiate a glucose tolerance test or other type of self-evaluation, e.g. where a well-characterized meal is eaten and the glucose response is tracked. A result of the test or evaluation may be communicated via a guidance message (e.g. "Your blood glucose stayed in range" or "Your blood glucose spiked quickly—consider a longer pre-bolus time".

Periodic Insights

Periodic insights may also be provided as guidance. For example, guidance may be provided as on a periodic schedule, such as a weekly update, or when it is determined that sufficient data are available to provide a reliable summary, such as 10 low-carb breakfasts versus 10 high carb breakfasts to provide comparative analysis, averages, graphs, probability zones, or other information about diabetes management. In an example, meals or foods may be grouped by types with a similar glycemic response in terms of magnitude and time course ('spikes versus slow'). In another example, meals or foods may be grouped by similar insulin dosing strategies, such as which meals needed correction boluses. In another example, the decision support engine may summarize the type of decisions that have unreliable outcomes in a manner that encourages education ('ideas for low-carb breakfasts') or medical review (e.g., inquiry to a doctor about strategies for management). The decision support engine may compile a summary of such information (e.g. problem meals) in anticipation of a doctor visit including successes and concerns.

In some examples, the decision support engine may provide schedule-based trend information. For example, a person's schedule may differ on weekends vs weekdays. This schedule difference may be reflected in the patient's glucose levels, or the patient's interest or availability in managing glucose levels, or the patient's goals or thresholds for notification. In some examples, periodic insights may be presented in a manner that differentiates based on schedule, e.g. weekend trends and weekday trends may be presented separately. Guidance may also include distinct therapy or behavior suggestions for different portions of a person's schedule, e.g. different basal patterns may be suggested based on knowledge of schedules. In various examples, the schedules are learned by a model, informed by a patient or caregiver calendar, based on user input via a user interface (e.g. answering questions on a smartphone), or combinations thereof.

The various insight examples described above may be translated to a different type of insight, e.g. an example described as an event-driven insight may be provided as a user-requested insight, and a user-requested insight may be provided as an event-driven insight through application of an algorithm or model to determine conditions and timing of delivery of the insight as guidance.

"Real time" does not necessarily mean immediate, but allows for intervention based on recent data or trends to affect near-term outcomes, as opposed to retrospective information presented to evaluate overall behavior or opportunities for therapy improvement.

Interaction of Inputs and Model(s)

Figure 2A:
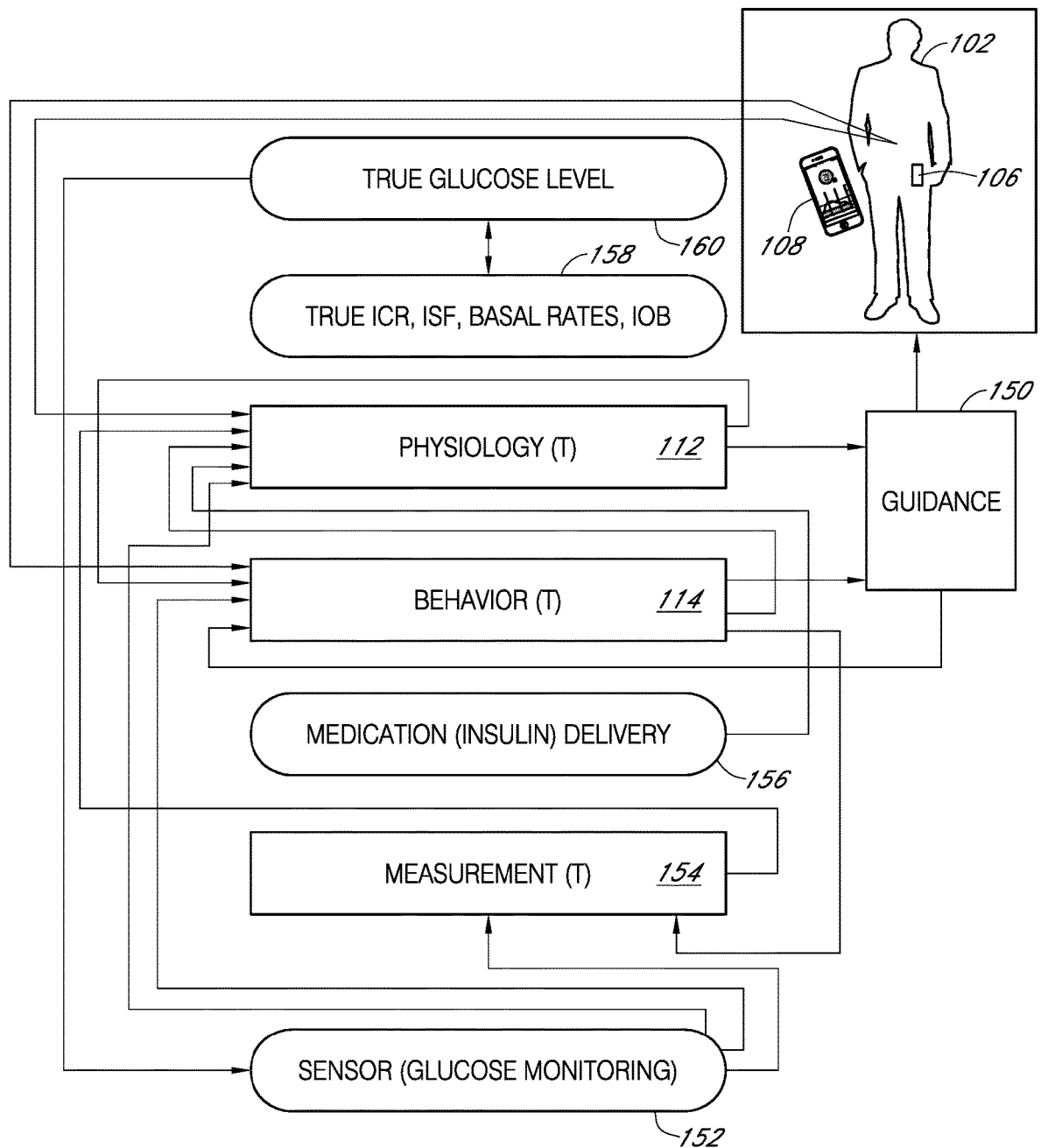
FIG. 2A is an illustration of the model shown in FIG. 1.
Figure 38:
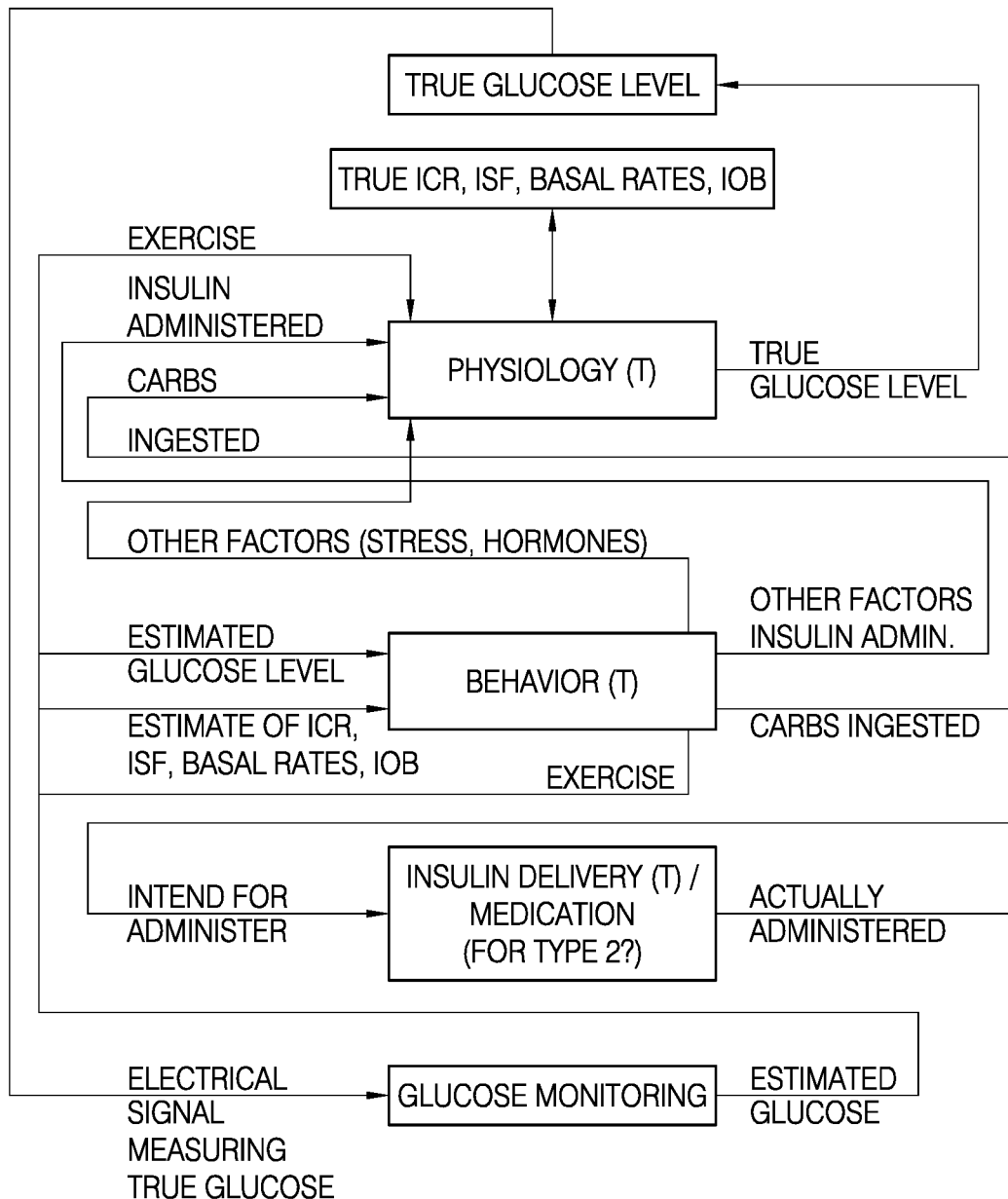
FIG. 38 is another illustration of the model shown in FIG. 1.

FIG. 2A is an illustration of an example configuration of the model 110 shown in FIG. 1. FIG. 38 is a diagram showing another example of the arrangement showing FIG. 2A. The patient 102 has an interest in controlling the true glucose level 160, which may be measured by a sensor 152. The physiology model 112, behavior model 114, and measurement model 116 process inputs and generate outputs (e.g., states), which may be provided to the patient as guidance, or may be used to determine guidance for the patient 102, as well as a time to determine or deliver the guidance. Guidance may be delivered via a guidance module 150.

A sensor system 152 may measure physiologic parameters such as a glucose level, activity, heart rate, respiration, or body temperature or contextual parameters such as ambient temperature, pressure, or location. The sensor system 150 may include a plurality of sensors integrated into a single device (e.g. a watch), or a group of multi-sensor devices (e.g. a watch and a wearable sensor), or the sensors may reside in individual discrete devices, which may or may not communicate with each other. For simplicity, the sensors that provide data inputs are simply referenced as a "sensor system." The sensor system 152 may include a continuous glucose monitor (more detail provided below) that may be configured to measure a glucose level that is calculated to be indicative of the true glucose level 160.

Data from the sensor system 152 may be provided as input to the physiology model 112 or the behavior model 114, or both. The physiology model 112 may also receive input from the patient 102, input from a measurement model 154 (described below), input from the behavior model 112 (such as activity state or stress state), or information about medication delivery 156 (e.g., insulin delivery), which may be received via user input from a patient or from a delivery device such as an insulin pump or insulin pen. The physiology model may also use other inputs. A detailed description of the physiology model inputs and outputs is provided below in relation to FIG. 2B, and numerous inputs are shown and described in FIGS. 14-16. The physiology model may provide physiology state information 158 as output, such as a current or projected glucose level or trend, insulin to carb ratio (ICR), insulin sensitivity factor (ISF), basal rate(s), or insulin on board (JOB), all of which may impact the true glucose level 160 and insulin delivery decisions or recommendations made by the guidance module 150 or the patient 102 or a caregiver or clinician.

The physiology model 112 or behavior model 114 may also receive information received from the patient, such as calendar information from a computer system such as a smart phone, or user input about specific activity or exercise, or user input about food consumed. The behavior model may also receive as input the guidance information delivered to the patient, as well as sensor data. The behavior model may also receive output from the physiology model. The behavior model may process the various inputs to determine a current patient state, or anticipate a future patient state, which may include, for example, exercise, sleep, availability for intervention, interest in receiving guidance, and other information about patient activity, interests or behavior. The behavior model may also receive contextual information or determine present or projected contextual information as a state (e.g. in a meeting or driving home), which may be used to determine guidance, or the timing of delivery of guidance. A detailed description of the behavior model inputs and outputs is provided below in relation to FIG. 2B, and numerous inputs are shown and described in FIGS. 14-16. A measurement model 154 may optionally be included in the system. Data from the sensor system 152 may be provided to the measurement model 154, which may process the sensor data to assess the accuracy or precision of the data, e.g. to determine a likelihood that a measured glucose level matches a true glucose level. The sensor system may use statistical methods such as variability or variance of sensor data points, trend information, historical information, as well as information provided by the behavior model, physiology model, and other sensors, to assess whether one or more sensor data points are likely accurate or inaccurate. For example, when successive blood glucose data vary widely or reveal patterns that do not reflect normal physiological patterns (e.g. 90 mg/dl, 112 mg/dl, 96 mg/dl, 121 mg/dl in successive five-minute increments), the measurement model may determine that sensor data are relatively inaccurate. Other sensor data may also be assessed. Sensor data may be evaluated based on the data being outside a range of probable values. For example, if an ambient temperature is detected as −5 Celsius in July, the model may conclude that the sensor reading is inaccurate, especially if location information is available. In another example, activity information may be processed, including correlating measurement model aspects with behavioral model aspects, to determine correlation to likely actual activity. For example, accelerometer information may be processed to assess whether motion is overly rhythmic (which may indicate mechanical motion, e.g. a bumpy ride, as opposed to exercise) or outside a probable range (e.g. a relatively sedentary person being active for three hours.) Output from the measurement model (e.g. accuracy state information) may be provided to the behavior model 114 or physiology model 112 for integration with other information to determine physiology or behavior states.

The guidance module 150 may deliver guidance information to the patient 102, for example via a user interface on a mobile device such as a smart phone. In some examples, the guidance module 150 may determine the guidance based on information (e.g. states) provided by the physiology model 112 and behavior model 114, and may determine a time to provide the guidance that is calculated to be useful to the patient. In other examples, the guidance and delivery time may be determined by a model, e.g. the behavior model 114, and the guidance module 150 may provide the determined guidance at the determined time. In various examples, the guidance module 150 may, for example reside on the mobile device 108, or may reside on a computer system, which may be remote from the patient or local and deliver guidance to the patient through a user interface on the mobile device 108 or another device.

Example Models

Figure 14:
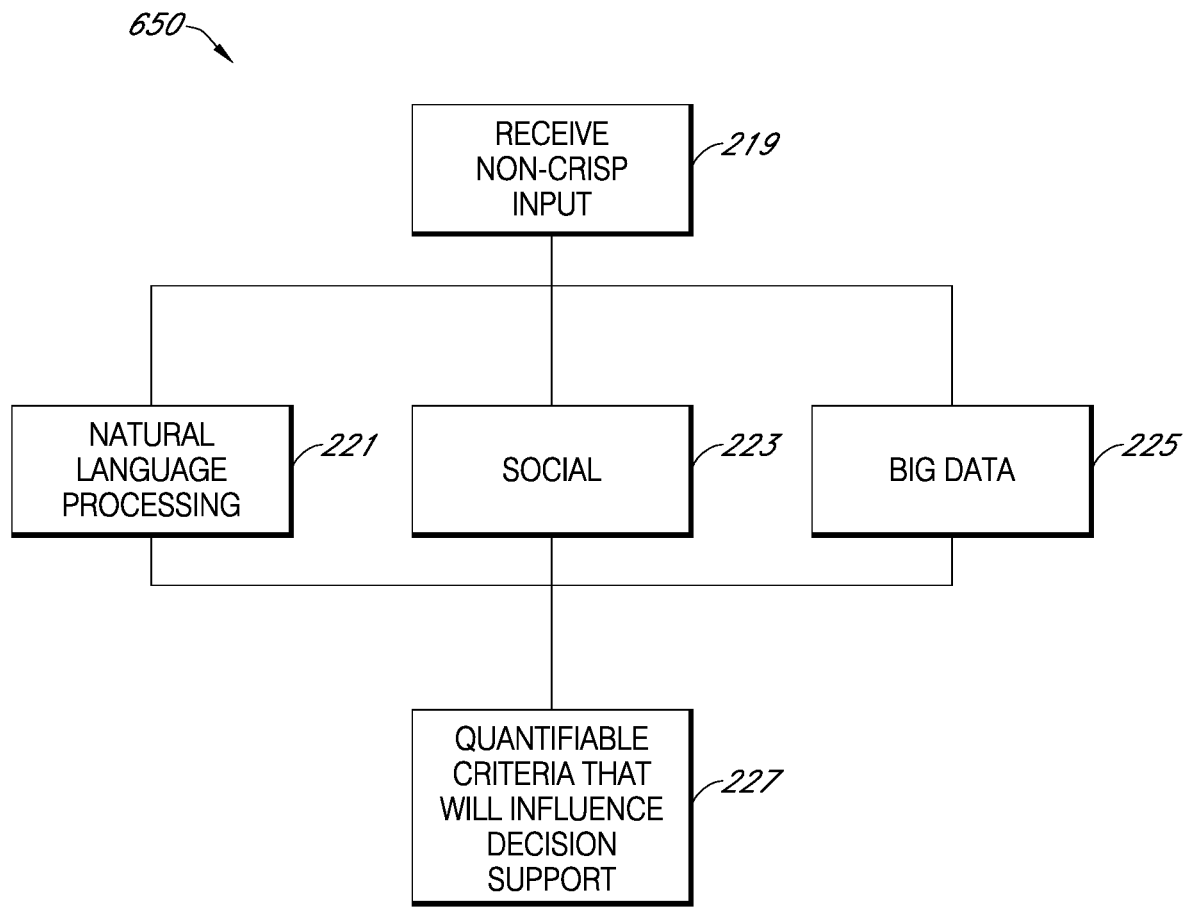
FIG. 14 is a flowchart illustrating ways of converting non-crisp inputs into quantifiable criteria.
Figure 15:
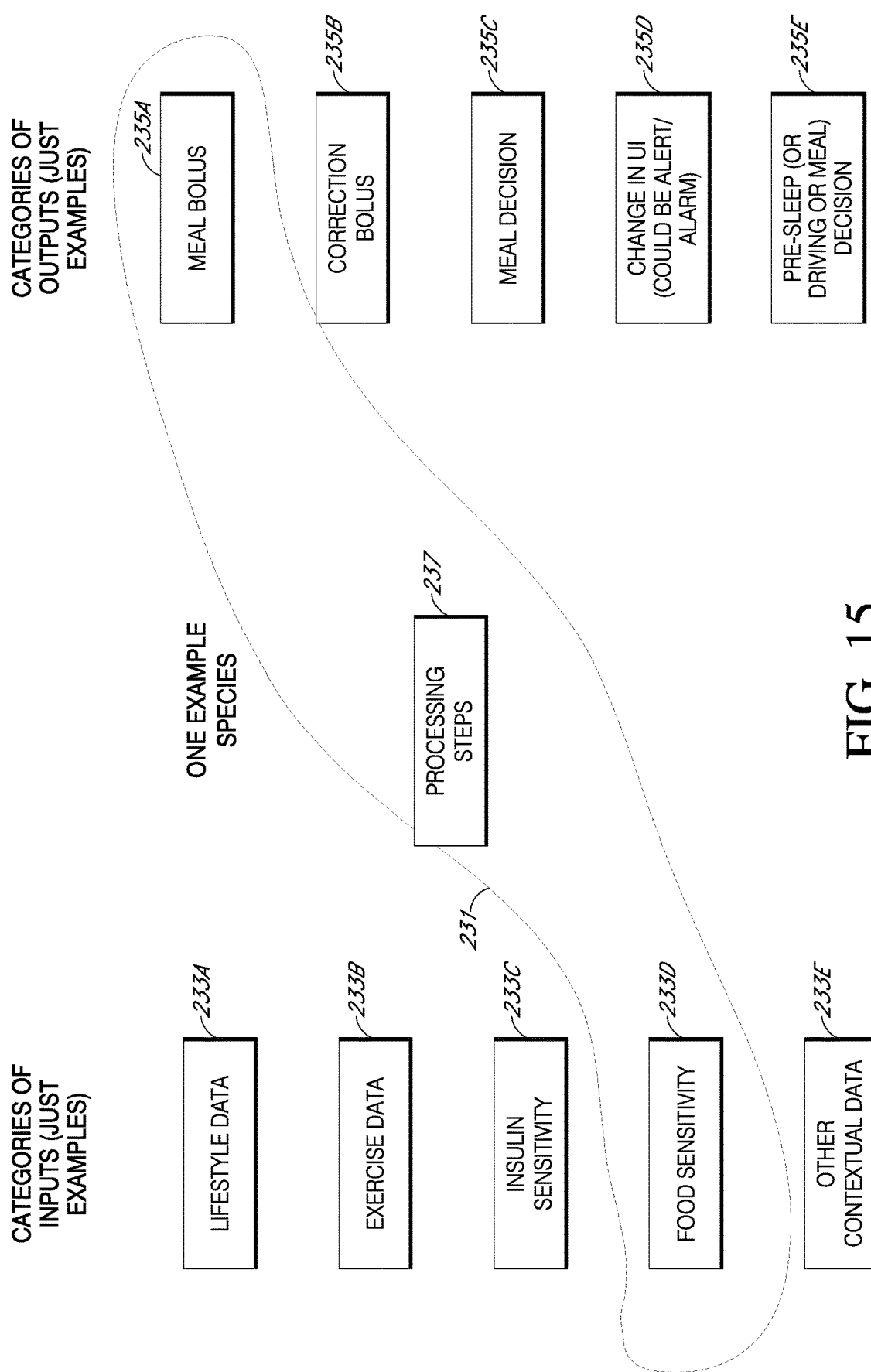
FIG. 15 illustrates use of one type of correlative parameter within a system model, e.g., a food sensitivity, in the determination of decision-support for a meal bolus.

FIG. 2B provides a more detailed illustration of example model inputs and example states that may be determined by applying inputs to a model. The physiology model 112, behavior model 114, and measurement model 116 of FIG. 2B are shown, along with example inputs and states for each model. Example inputs are shown in the left, and example determined states are shown in the right. FIGS. 14-16 below provide a more comprehensive recitation of inputs, any of which may be applied to one or more of the models. States may be identified by a physician or expert or learned by the model via machine learning. Each state may have two or more (and possibly a multiplicity) of state values, e.g. discrete numerical values, ranges, or qualitative values (high/medium/low or stable/unstable), The states may be determined by applying one or more of the sources of input data to a model. While three models are shown, one skilled in the art would understand that the models may be integrated into one or two models, or broken into a larger number of models or sub-models.

Physiologic Model

Figure 25A:
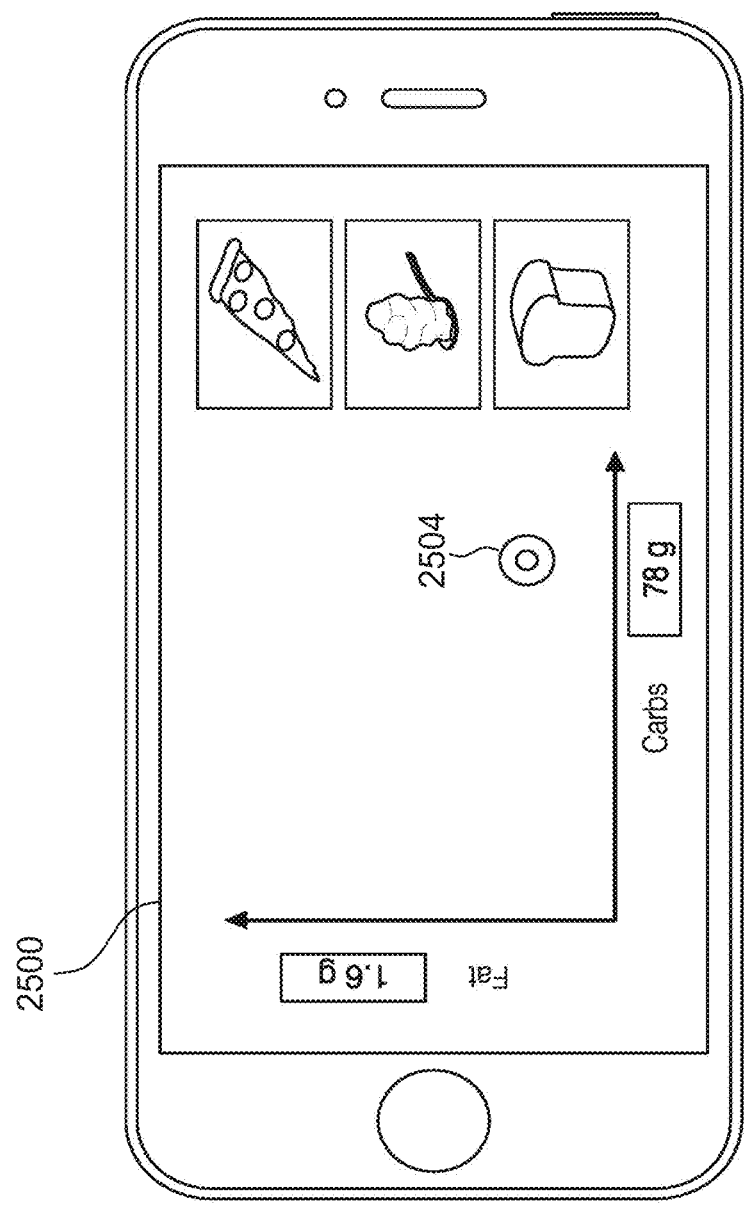
FIGS. 25A and 25B are illustrations of an example user interface through which a user may select carbohydrate content and fat content on a graph.
Figure 25B:
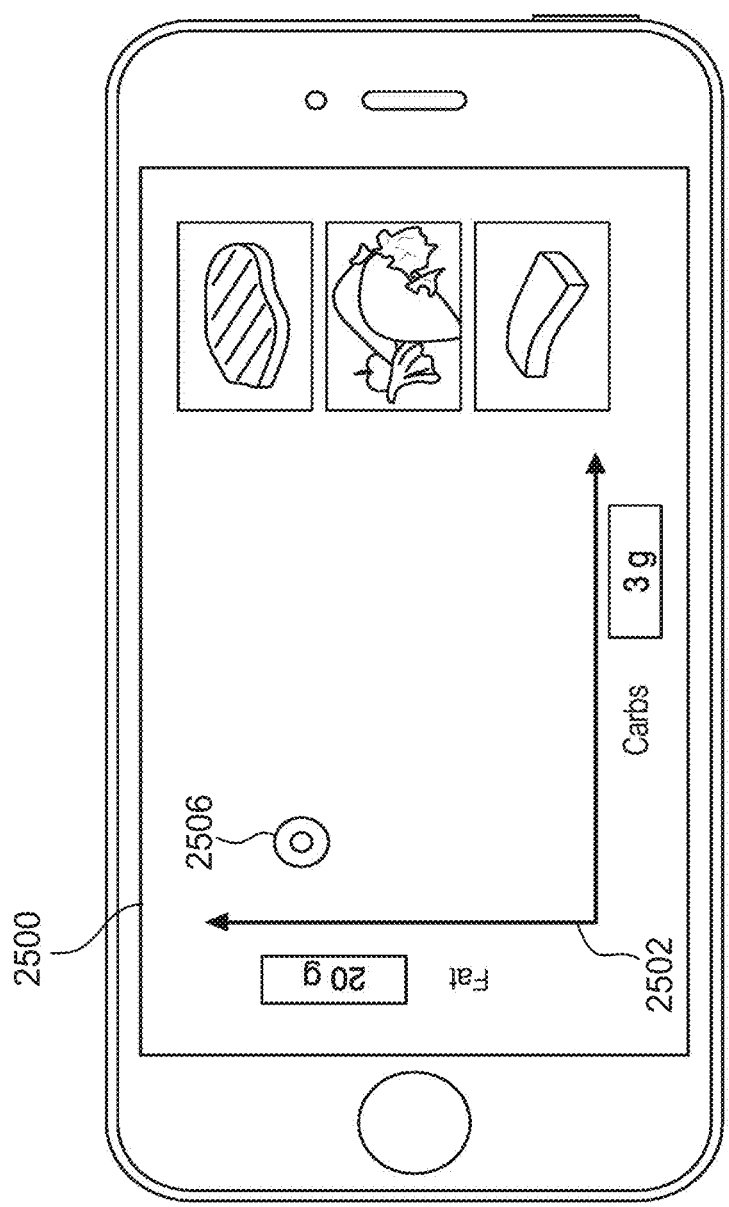

Food consumption may be provided as an input to the physiology model 112. The food consumption information may include information about meals, snacks, and beverages, such as the size, content (carbohydrate, fat, protein), sequence of consumption, and time of consumption. Food consumption may be provided by a user through a via manual entry, or by providing a photograph through an application that is configured to recognize food types and quantities, or by scanning a bar code or menu. In various examples, meal size may be manually entered as calories, quantity ('three cookies'), menu items ('Royale with Cheese'), or food exchanges (1 fruit, 1 dairy). In some examples, meals may also be entered with the user's typical items or combinations for this time or context (e.g. workday breakfast at home, weekend brunch at restaurant). In some examples, meal information may be received via a convenient user interface. For example, as shown in FIGS. 25A and 25B, a user interface 2500 may enable a user to indicate by touching a graph 2502 (or other graphical user interface element) an amount of fat and carbohydrate (and optionally additionally protein) in each meal. FIG. 25A shows a selected point 2504 on the graph 2502 with high carbohydrate (78 grams) and low fat (1.6 gram) content. FIG. 25B shows a selected point 2506 on the graph 2502 with high carbohydrate (78 grams) and low fat (1.6 gram) content. FIG. 25B shows a selected point 2506 on the graph 2502 with low carbohydrate (3 grams) and relatively high fat (20 gram) content. Example meals with similar nutritional content (e.g. carb to fat ratio) may be shown on the user interface.

Activity may also be provided as an input to the physiology model. Activity information may be provided, for example, by an accelerometer sensor on a wearable device such as a watch, fitness tracker, or patch.

Patient statistics, such as age, height, weight, body mass index, body composition (e.g. % body fat), stature, build, or other information may also be provided as input, through a user interface, or by interfacing with an electronic source such as an electronic medical record, or from measurement device such as a wireless, e.g., Bluetooth® wireless communications technology enabled, weight scale or camera, which may, for example, communicate with the mobile device 108 to provide patient data.

Insulin delivery may be received by the model, via a wireless connection on a smart pen, or via user input or from an insulin pump. Insulin delivery information may include insulin volume, and time of delivery. Other parameters, such as insulin action time or duration of insulin action, may also be received as inputs.

The physiology model 112 may also receive user input through a user interface, such as on a smart device 108. Such user input may include mental state or stressor information, the delivery of therapy, such as the use of glucagon to stimulate liver release of glycogen in response to a low blood sugar, recommended basal rates or insulin-to-carb ratios (e.g. received from a clinician), or recorded activity (e.g. intensity, duration and time completed or started).

Input may also be received from sensors, such as physiologic sensors, which may detect heart rate, respiration, oxygen saturation, or body temperature (e.g. to detect illness). Electromagnetic sensors may also detect low-power RF fields emitted from objects or tools touching or near the object, which may provide information about the patient activity or location. Glucose level information may also be provided as input, for example through a continuous glucose monitoring (CGM) system that provides CGM data. Input may also be received from smart pill dispensers that track when customers take medicine, a blood ketone meter, a laboratory-measured or estimated A1C, other measures of long-term control, or sensors to measure peripheral neuropathy using tactile response, such as using haptic features of a smartphone, or a specialty device.

States from the measurement or behavior model may also be provided as input.

Time may also be provided as an input, such as time of day, or time from a real-time clock.

In some examples, model inputs may be inferred, e.g. from one or more of historical user inputs (e.g. a meal diary), geolocation, insulin dosing, CGM features (rising blood sugar), or time of day. In some examples, the model may operate in a learning mode, where a database of information (historical or real-time) is collected. Causes or effects or both may be deduced from the database. Patterns may also be deduced from the database, such as patterns associated with certain meals or meal types or activities, or insulin action time or duration of insulin action, or combinations thereof.

Physiologic States

One or more physiologic states may be determined by applying inputs to the physiology model. Metabolic rate may include a basal metabolic rate (e.g., energy consumed at rest) as well as active metabolism, e.g. energy consumed by activity, e.g. exercise, activity, or exertion. In some examples, basal metabolic rate and active metabolism may be tracked as separate states. Activity level may also be determined, for example based on an activity sensor or other physiologic sensors. The activity level state may, for example, include four states: sleeping, resting, active, exercising. Insulin sensitivity may be determined using historical data, real-time data, or a combination thereof, and may, for example, be based upon food consumption, insulin delivery, and resulting glucose levels. Insulin on board may be determined using insulin delivery information, as well as known or learned (e.g. from patient data) insulin time action profiles, which may account for both basal metabolic rate (update of insulin to maintain operation of the body) and insulin usage driven by activity or food consumption. Meal state may include, e.g. fasting, premeal, eating, post-meal response, or stable. Meal state may also include nourishment on board, e.g. meals, snacks, or beverages consumed, and may be determined, for example from food consumption information, time of meal information, and digestive rate information, which may be correlated to food type, quantity, and sequence (e.g., which food/beverage was eaten first). Health and sickness may be determined, for example, based on user input (e.g. pregnancy information or known sickness information), from physiologic sensors (e.g. temperature), activity sensors, or a combination thereof. Example health states may include, for example, health, illness, rested, and exhausted. Glucose level may be determined from sensor information (e.g., CGM data), optionally in combination with the measurement model state. In some examples, a glucose level state may also be determined from the model when CGM data are not available or is of uncertain reliability, for example based upon historical information about glucose levels in particular situations, e.g. given a combination of food consumption, insulin, and activity. Degree of glycemic control (not shown) may also be determined as a state, and may be based, for example, on glucose levels, variation in glucose level, or insulin dosing patterns. Confidence levels may be applied for one or more of the states (e.g., high, medium, low, or numerical confidence).

In some examples, transitions between states may be important decision points for determining guidance or a time to determine or deliver guidance. For example, a user may especially need guidance at transitions between states. For example, guidance may be needed while waiting for the glucose response after a meal, or deciding what to do before exercising. These state transitions, or projected state transitions, may be identified by a system (e.g., using a model) and used to determine a time to determine or deliver guidance. Examples of these states transitions may include Active→resting→exercising→sleeping, or Health→illness→rested→exhausted, or variations in degree of glycemic control (e.g., glucose level variation, variation in insulin sensitivity, insulin dosing changes), or a transition to pregnancy. In some examples, the physiology model 112 also includes a disease stage state, such as for Type II diabetics. Example disease stage states for Type II diabetics can include a prediabetic stage, an oral treatment stage, and a basal insulin treatment stage. Insights provided by the decision support engine may vary for hosts in different disease stages, for example, as described herein.

Modeling Kinetic and Potential Energy Flows

In an example, the physiology model 112 may characterize the flow of energy in the human body, which may include the effect of meals, exercise, glucose and insulin, as well as other hormones such as cortisol and adrenaline. Energy inputs may include meals and snacks (characterized by time, size, and type), and glucose production by the liver (e.g., the "dawn effect" where the body releases energy in early morning, or the release of energy by the liver to counter a low blood glucose level). Energy outputs may include energy consumption from activity, such as exercise, and glycogen replacement by muscles or the liver, and glucose uptake driven by insulin. Insulin time action-profiles may be taken into account as well as the separate impacts of the basal (e.g. resting) metabolism and active metabolism (e.g. from activity/exercise). The model 112 may be tuned to a subject's physiology using user-inputs, measurements (e.g., CGM patterns and fitness tracker or accelerometer) and inference, e.g. the learning of patterns and associations from data.

At a high level, the physiologic model may track energy inputs, track energy outputs, and determine one or more physiologic states. This energy-characterizing aspect of the physiology model may be used to predict future glycemic states (e.g. high glucose level, low glucose level, rising glucose trend, falling glucose trend). The physiologic model may also interact with the behavior model and a guidance module (e.g., decisions-support app) to determine when the user is likely to need context-specific guidance (e.g., advice, alerts, or warnings), such as during a transition from resting to exercising, or from healthy to sick.

Behavioral Model

A behavior model may reflect the behavior, preferences, schedule, and other information about the user. Referring again to FIG. 2B, the input to the behavior model may include user input, such as input through a user interface regarding activity, level of interest in guidance, or location. Input to the behavior model may also include calendar information, such as availability or activity information received from a computer or smartphone calendar application. The input may also include activity, such as information from an activity sensor such as an accelerometer on a watch or fitness band. Inputs to the behavior model may also include location (e.g. GPS), time (e.g. from a real-time clock), prior guidance to a user, and the physiology state. Additional inputs are also possible.

Behavior model states may include availability or convenience of intervention (e.g. available/not available or convenient/not convenient) which may be deduced from a calendar or inferred schedule or from a learned pattern of a patient or caregiver schedule. Availability or convenience states may also include the proximity of caregiver to a patient, which may be inferred from location information or calendar information.

Behavior model states may also include risk tolerance (e.g. comfort with trends toward low blood glucose levels, which may depend on experience with intervention or the availability of caregivers for intervention), interest in guidance, activity state, (e.g. exercising or not, which may be inferred from a calendar or activity sensor), sleep state (e.g. sleep or resting or awake, which may be inferred from an activity sensor, calendar, or other information), and appetite (which may be inferred for example from meal patterns).

Engagement (or level of engagement) may also be determined as a behavior model state. For example, engagement factors may include user response to decision support, in terms of time, activity, and type of support (user-requested, context generated, periodic). Engagement states may include, for example, the type of guidance that tends to prompt action, the actions that a user participates in, which may be correlated to time, (e.g., can't take a walk 9 to 5) or activity (e.g. no finger-prick blood glucose tests while running). A level-of-engagement state may also reflect the time a user is engaged in receiving or following guidance (e.g. where shorter times suggest guidance is disregarded). The engagement state may also include the type of communication, which may be correlated to activity or schedule, such as learning an appropriate mode to interact with a user depending on the time of day and location. For example, a user may get watch or phone display messages in a meeting, voice messages in the car, and tiered messages based on urgency while sleeping, where urgent messages are accompanied with a sound or vibration and less-urgent messages quietly appear on a display or watch. In some examples, level-of-engagement logic and schemes applied above may also be applied to caregivers (e.g. data followers on smart devices), to inform them of needs for intervention, or to let them know that the patient or another caregiver is aware of or managing the situation.

Figure 26:
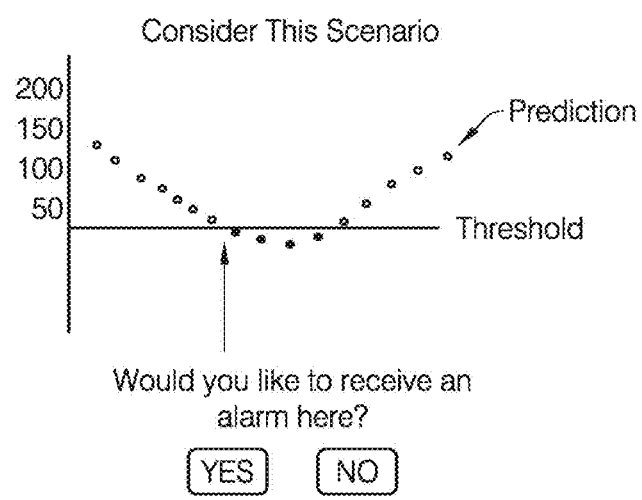
FIG. 26 is an illustration of an example user interface through which alarms may be configured.

A level-of-concern state may also be determined by the behavior model. For example, the system may determine situations that may create concern about the current physiologic state, the consequence of treatment decision, or potential future states, and determine a level of concern based upon the presence or absence or likelihood of such situations. For example, the manner in which a patient views CGM values or guidance, or the device on which the patient views the information, how the patient views the information (e.g. on a watch, or phone, or interactions with a full screen view or only a notification screen that may provide less information) may indicate a level of concern (where seeking of more information or less convenient information indicates more concern). The frequency with which a CGM datum or guidance is checked or requested, or when the user stops checking, may also indicate a level of concern (more frequent indicates more concern). Other factors that may be accounted for in determining a level of concern may include self-monitored blood glucose readings (e.g. finger prick sensor readings), requests for decision support and the circumstances surrounding such requests (e.g., restaurant meal versus home cooked), when insulin adjustments are made (basal, prandial, postprandial), the consumption of a snack or fast-acting carbohydrates to avoid lows, the presence or attention of caregivers (e.g. data followers) who watch glucose levels or respond to data updates, or patterns of alarms. In some examples, level of concern or alarm preferences may be learned through a model or set through user input based on real or hypothetical data, as shown in the example user interface 2602 shown in FIG. 26.

Level of concern state may be based on time periods when a user is concerned (e.g., time of day, or a period of time after a meal, or a period of time after exercise, or certain days of the week or days of the month, or times derived from calendar events, e.g. holidays or school events.) Time periods may also be applied to care givers (e.g. data followers). The level of concern for time periods may, for example, be derived from user input, or learned from user behavior. Level of concern may also reflect the user's goals, e.g. the level of user concern with alarms and lows, or focused on maximizing the time in-range, or both.

The behavior model may also include a guidance state, which may include for example an insulin guidance state (e.g. deliver X units of insulin, or increase/decrease basal rate), and a carb consumption guidance state (e.g. eat X grams of carbs).

In some examples, the generation of guidance messages or other information for the patient may be conducted as part of the behavior model (e.g. as output states from the model). For clarity and simplicity of description, guidance generation is described separately below.

Measurement Model

A measurement model may provide information relating to sensor measurements, such as CGM sensor measurements. The measurement model may, for example, provide an indication of the accuracy of data from a sensor.

A CGM measurement model may add context to the glucose values and patterns generated from sensor data. The model may allow for different data types. For example, confidence bounds may be determined for data values or a data set. The confidence bounds may be presented to the user or provided as input to another model. The model may, for example, provide accuracy bounds that adjust for day of use (e.g., freshly implanted sensor vs. aging sensor, which may become inaccurate), adherence to calibration schedules, the impact of lag at high rates of changes (both due to physiologic lag in the movement of glucose levels in interstitial fluid, and sensor lag because the sensor only takes a reading periodically, e.g. every 5 minutes). The measurement model may also monitor for consistency between the blood glucose and CGM readings, as an indicator of the reliability of a blood glucose reading, CGM reading, or both. Similar principles may be applied to other sources of data to assess accuracy, consistency, or variability.

With reference to FIG. 2B, the measurement model may receive user input, sensor data, and calibration information as input, and may determine measurement states such as sensor accuracy (e.g. high, medium, low), confidence in sensor data, or sensor status (e.g. warmup/active status, time since insertion or time until replacement, or sensor connectivity). Other sources of measurement model input data may include data configured to allow for factory calibration or non-user intervention calibration.

Determination of Timing of Guidance

In various examples, guidance, and the timing of guidance, may be determined based on state models or other inputs. For example, guidance may be determined from one or more physiologic states or behavior states, or a combination thereof. The timing of determining of guidance or delivery of guidance may also be determined from physiologic and behavior states. In some examples, a plurality or multiplicity of states may be used to determine guidance, and the timing of guidance. In various examples, the guidance, and timing of delivery of the guidance, may be made by the behavior model, or by a guidance module that uses state information such as states from the behavior model and physiologic model.

Learning

In some examples, the system may enter a "learning mode" in which the system observes physiologic or behavior data. For example, the system may collect CGM values, blood glucose measurement, insulin doses, food, activity, medication, stress levels, sleep patterns, hormone cycles, location (via GPS, etc.) and other information to build an information set from which patterns may be deduced. The system may, for example, determine basal dose, insulin sensitivity, insulin-to-carb ratio, insulin duration of action, or bolus for commonly used meals. In an example, protocols may be followed, in cooperation with patient involvement, which may include tracking factors such as ingestion of carbohydrates and insulin administration. The resulting glucose levels or trends may be determined for a patient, especially if the patient is newly diagnosed or treated. Some factors, such as insulin sensitivity, vary throughout the day, so in some examples a protocol may be followed several times at different times of day to obtain correlations between the desired parameter (e.g., insulin sensitivity) and time of day. A carb-to-glucose ratio may also be determined, for example by determining how much a patient's glucose level increases per one gram of carbohydrate, and accounting for an underlying basal rate.

In an example, for a basal test, a user may be asked to pick a day when the BG of the user is in a specified range (e.g., between 80-250), plans to skip a meal, controls the diet of the user so a previous meal is not high fat or very high in carbs, and avoids exercising or doing anything else that might affect the blood glucose of the user. A system may receive an input from a user to initiate a basal test. The system may then evaluate blood glucose concentration levels for a period of time (e.g., three hours) after the last meal. If the blood glucose levels are stable through the period of time, the system may declare that the basal rate(s) are correct. If there are periods of time when the BG is increasing or decreasing, then basal rates affecting that period of time may be modified by small, safe increments, until the blood glucose is stable over the whole period. In some examples, this process may be repeated until a full 24-hour period (or longer, e.g. a week) has been covered by a successful basal test.

For an insulin-to-carb ratio test, a user may be asked to pick a time when the blood sugar is in a specified range (e.g., between 80-250), at least a specified amount of time (e.g., four hours) from their previous meal, at a time not affected by exercise, stress, or anything else that might affect blood glucose, and eat a specific meal with known carb content and moderate glycemic index. In some example, the system may request that the user eat specified foods or ask the user to consume food with a nutritional label and take a picture to confirm. Because the carb content is established with confidence and other sources of glucose variability is minimized, the system can determine an ICR for the patient. In some examples, the process may be run multiples to enable the system to hone in to the correct ICR. This may be achieved, for example, by making small, safe, run-to-run changes until the meal content is adequately covered (i.e. until the system identifies an appropriate insulin dose that produces stable glucose levels in a desire range).

In another example, to estimate an insulin sensitivity factor (ISF), a user may be asked to pick a time that is a specified amount of time (e.g., 4 hours) after the last meal, and to avoid exercise and other behaviors that may affect glucose levels. The system may then ask the user to take a correction bolus. The system may then monitor the glucose response and use the response to determine an insulin sensitivity factor. In some examples, the process may be repeated two or more times until a correct ISF value is determined.

In some examples, basal rates are determined first, to enable accurate estimate of ISF and ICR and ISF. In some examples, a decision-support system may determine appropriate periods to determine basal rates, ISF, or ICR, instead of or in addition to requesting patient involvement or cooperation.

The system may integrate various states and learn the inter-relation of states. For example, the system may track exercise intensity and duration, glucose levels, and insulin dosages, and learn how exercise impacts glucose sensitivity. A determined glucose sensitivity may be provided as guidance or may be used to determine other states or as an input to an algorithm to determine guidance. The system may also reference or build nutritional databases and link the database to a patient (e.g. track how a patient responds to specific meals or types of foods). The system may also track insulin sensitivity, and pattern of insulin usage, for example, to predict insulin sensitivity changes or insulin usage patterns. The system may also track a recent history of glycemic control, which may be used to predict future control, or stress response of a user, which may impact insulin sensitivity (e.g., the body releases cortisol in response to stress, which makes the body insulin resistant.)

In an example, the system may learn when a patient makes a treatment decision, and how the patient and caregivers (e.g. data followers on a smartphone) track the outcome of the decision. The system may then anticipate when a patient is likely to make a similar decision, and what information would be useful in making the decision and provide such information as guidance. The system may also anticipate a desired outcome, and then either provide a confirmatory notification (e.g. "Good job! Your post breakfast peak was 140 mg/dL and now you are stable and in range") or recognize that the desired outcome has not been achieved ("After your 3-unit bolus at 7:00 am you are still at 220 mg/dL and rising").

In some examples, the system may identify a situation or pattern of interest (e.g., a common situation, such as a meal, exercise regimen, or holiday), or receive identification of such a situation or pattern from a user and develop a more effective or more accurate guidance or timing of guidance for the identified situation. For example, the system may obtain information about the identified situation by requesting user input, or by supervising an "experiment" to enable collection of a larger volume of data or more accurate data. The additional data may be used improve guidance or timing of guidance for the identified situations.

States

In some examples, the content and timing of guidance may be determined by states. For example, it may be determined to deliver guidance to consume carbs when in response to the occurrence of a specified glucose state, such as a glucose level or trend satisfying a specified condition. In some examples, a state may be based on a combination of parameters, such as exercise and glucose. For example, a "low glucose exercise" state may correspond to a glucose level satisfying a condition (e.g., glucose level below a threshold) and exercise being anticipated (e.g., from a pattern or calendar) or exercise being detected (e.g., from a physiologic sensor or accelerometer). In some examples, a model may be based upon a plurality or multiplicity of states. For examples, a model may include one or more of a glucose state, an exercise state, a health/sickness state, and a sleep/wake state. In some examples, a system may combine or use a plurality of models to determine guidance, and when to deliver guidance.

In some examples, state transitions may be detected using the model, and used to generate guidance or notifications to the patient. Some physiologic state transitions (e.g. sickness/health) may occur over the time period of days or weeks, whereas others may occur in hours or minutes (e.g. glucose level or trend). In some examples, guidance may be delivered when a state transition condition is satisfied. For example, when a patient is trending to a low glucose level and transitions to an exercise state or is determined as likely to exercise soon (e.g., using a pattern or based on location at a park or gym), guidance may be given to consume some carbohydrates. In some examples, a combination of state transitions may trigger guidance (e.g. transition from normal glucose to low glucose and a transition from sedentary to active/exercising state.)

The probability of state transitions may be used to determine guidance, or whether and when to deliver guidance. For example, when a probability of a transition to an undesirable state is detected, guidance may be determined and delivered. In some examples, the guidance may be determined and delivered only if one or more additional conditions are satisfied, e.g. when an availability state or a level of concern state meet specified conditions.

In some examples, the system may deliver guidance when a specified combination of state conditions is satisfied, or a specified combination of state transitions has occurred, or is calculated to be likely to occur. For example, guidance may be delivered when both a glucose state and an exercise state satisfy specified conditions, e.g. guidance may be delivered when a low glucose state is present or likely, and a patient is about to exercise, or just completed exercising. In some examples, the system determines a messaging frequency for providing insight or guidance based on a state condition or conditions, such as the host's engagement state.

In some examples, the system may adjust the guidance based on the severity of the situation, level of concern and level of engagement. For example, a determination of whether to withhold guidance or deliver guidance may be determined in part based on the level of concern state or level of engagement state of the behavioral model at a particular point in time. Where level of concern or level of engagement are relatively low, delivery of guidance may be deferred until a time when the user is more available, or a time that is more convenient for the user. In a situation where a level of concern or level of engagement state is high, guidance may be delivered even though it may be at a time that is inconvenient. For example, guidance regarding an emergent situation may be delivered even though a user is in a meeting, but guidance about a relatively routine (e.g., low concern/engagement) problem may be deferred until after the meeting. In this way, the messaging frequency of insight and/or guidance delivered to hosts with engagement states indicating low levels of engagement may be reduced. This may prevent low-engagement state hosts from being overwhelmed with guidance. As the host's level of engagement changes, the frequency of guidance may also change. For example, the host may respond to initial low-frequency guidance by becoming more engaged—e.g., reaching an engagement state indicating a higher level of engagement. If this occurs, the frequency of may be increased. For example, the delivery of guidance may not be deferred and/or may be deferred for a smaller amount of time than when the host is in engagement states indicating lower levels of engagement. If the host's engagement state changes to indicate a lower level of engagement, the frequency of guidance delivery may be decreased.

Guidance Examples

In various examples, guidance is determined based at least in part on time. For example, the determining of guidance may be based on clock time, or time of day (e.g. zones, such as morning, afternoon, evening, night). Insulin sensitivity tends to vary based on several overlapping functions of time. For example, diabetes patients tend to be more insulin resistant in the morning due to factors such as other hormones secreted by the body in the morning. The determining of guidance may be based at least in part on time of day to account for time-varying insulin sensitivity. The determining of guidance may also vary with time based upon patient behavior, such as exercise routine and daily eating habits and eating schedule. Other physiological parameters (e.g., stress, alcohol consumption, heat exposure, adrenaline-inducing events such as sporting competitions) may also have a dependence on time.

In various examples, determined guidance may include guidance on how to respond to a specific situation (e.g., a detected or predicted hypoglycemic event or hyperglycemic excursion) or more general guidance regarding therapy or behavior (e.g., a change to insulin to carb ratio for a particular meal (e.g., lunch) or to get exercise in a particular timeframe (e.g., "consider a quick walk after breakfast to increase your insulin sensitivity")).

Figure 27A:
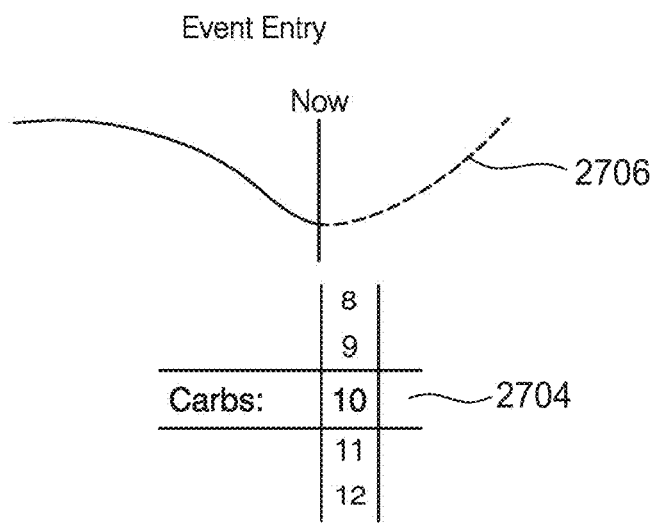
FIGS. 27A and 27B are illustrations of a user interface that shows predictive data for selected amounts of carbohydrate ingestion.
Figure 27B:
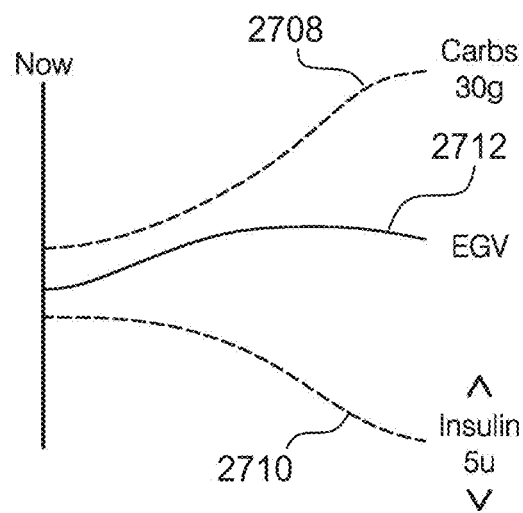

In some examples, information determined from the physiology model or the behavior model may be used to propose alternate approaches to common patterns. For example, the system may determine that user has a tendency to over-correct or under-correct in a particular situation, e.g. at a particular time or after a particular meal, and guidance may be provided when the system detects the pattern associated with the correction error. In some cases, the system may simulate what would happen with alternate therapy approaches or compare historic approaches. For example, an alternative approach may be provided as guidance after an over-correction or under-correction has occurred. In another example, predictive trends may be presented for a proposed behavior. For example, a user may enter via a user interface a proposed insulin dose or snack or meal, and the system may display a predictive trend. In an example illustrated in FIG. 27A, a user may be presented with a user interface that includes a scrolling dial 2704 that may allow for selection of a carb amount, and the system may present a predictive trend 2706 that shows the likely outcome from a snack containing the selected amount of carbs. In another example, illustrated in FIG. 27B, a user may enter a proposed carb value, the user may enter a proposed insulin dose, and the system may present a user interface that shows three curves, one curve 2708 for a scenario where carbs are ingested but no insulin is administered, one 2710 for a scenario where insulin is administered but no carbs are ingested, and an estimated glucose value curve 2712 for a scenario where both glucose and insulin are administered. In some examples, the dial shown in FIG. 27A may be provided on the user interface 2720 shown in FIG. 27B. While the predictive insulin trends are shown as lines, in another example, probability cones may be shown in place of lines.

In some examples, the system may provide nighttime readiness guidance to provide a user comfort at night that the user will not trend to low glucose levels at night, to reduce nighttime alerts, and to reduce nighttime hypo events. To develop long range (e.g., 6-10 hours) or high confidence predictions about states or state transitions, the system retrieves more information from the patient or sensors, or may conduct additional processing, to increase the likelihood that guidance enables a full night sleep without interruptions to eat or deliver insulin. The nighttime readiness feature may provide guidance to take action before going to sleep, e.g. to eat carbs or administer insulin before going to bed.

In some examples, the system may exchange data with a clinical supervision platform. The system may provide, receive, or exchange sensor data, patient data, or prescription information or dosing information with the clinical supervision platform. In some examples, guidance may be checked against the clinical supervision platform (e.g., by a human clinician or algorithm) before the guidance is delivered to the patient. In some examples, guidance, and optionally also resulting data such as blood sugar curves, may be provided to a clinical supervision platform after delivery to the patient, to enable coordination or feedback from a clinician or otherwise allow for shaping or optimization of future guidance, such as a change of insulin type, dose, or timing.

In some examples, a decision support system may include a diabetes control supervisor that may be configured to provide overall guidance or feedback. The diabetes control supervisor may, for example, quantify diabetes control. This may include a metric of effectiveness of control of estimated blood glucose levels as measured against a specified condition, criterion, or criteria, such as measure (e.g., percent) of time within a specified blood glucose range.

Treatment Parameters

A decision support system may also provide guidance regarding treatment parameters. For example, the system may identify when changes in basal rates, ICR, ISF, or IOB are needed. The system may also prompt for a test, for example if the type or amount of change needed cannot be identified within a specified metric (e.g., confidence level). Real-world data can present challenges in determining treatment parameters. Theoretically, if the basal rates are correct and the ISF is known (or assumed to have a known relationship to other treatment parameters), a bolus can be determined with acceptable accuracy. Similarly, if the ICR and ISF are assumed to be correct, and carb estimates are assumed to be accurate (at least on average), then the basal rates may be fine-tuned within acceptable limits. However, real-world conditions may be filled with uncertainty, complexity, and overlapping factors, and errors can exist in all parameters, which can make the idealized scenarios described above rare or difficult to recognize. To deal with this systemic complexity, a decision support system may include a model or algorithm may learn or detect inappropriate specific basal rates, ICRs, ISFs, or insulin-on-board duration from collected data. In some examples, the parameters may be determined retrospectively from days or weeks of data and determined parameters may be evaluated for accuracy as additional data are collected. A decision support system may also use a model or algorithm and learned parameters or past data in combination with real-time or recent data to generate guidance, and to calculate a time to deliver guidance.

In an example, in noisy data with multiple overlapping effects, an inappropriate basal rate may be identified by identifying one or more patterns of recurring lows or highs more than a specified amount of time (e.g., 4 hours) after meals (i.e. after the effects of food and basal doses have faded). Similarly, an inappropriate ICR may be identified by identifying recurring low or high glucose levels a specified amount of time (e.g., 2-4 hours) after meals (while food and basal insulin is still active) in incidents where recurring lows/highs are did not occur more than a specified second amount of time (e.g., 4 hours) after the same meals (which suggests that the basal rate was correct).

The decision support system may account for whether the low or high glucose levels happen with different amounts of carbs, correction factors, or initial glucose levels. In an example, if the glucose level is in range pre-meal (e.g. no correction bolus on board) but out of range after a meal, then error is likely attributable to an inappropriate ICR. In some examples, glucose trends for meals with different characteristics can be compared to verify or refine detected inaccuracies in ICR. For example, when a collection of patterns of glucose levels that trend low reveal that, with a higher carb count, the glucose level trends low faster, or the glucose level gets lower, then it may be inferred that an ICR is likely too high (i.e. because of the high ICR too much insulin is delivered, and the impact of the high ICR is amplified with larger amounts of carbohydrates, which produces faster low glucose trends or lower glucose levels.) Similarly, when a collection of patterns of glucose levels that trend high reveals that, with a higher carb count, the glucose level gets high faster or gets higher, it may be inferred that the high glucose trend is likely attributable to an ICR that is too low (i.e. not enough insulin is delivered, so glucose levels run high and the impact is amplified with higher carb counts), Insulin Sensitivity Factor In another example, the decision support system may provide guidance regarding insulin sensitivity. For example, the system may track and report insulin sensitivity or changes or trends in insulin sensitivity. The decision support system may also provide fault detection (further described below) and may assist a user with determining whether a problem is caused by a treatment parameter or a system fault (e.g., to differentiate insulin sensitivity problems from hardware fault problems). Guidance with respect to insulin sensitivity may be particularly useful when the patient undergoes a change in insulin sensitivity. For example, during "normal" conditions, a patient's diabetes may be well controlled, for example by estimating and using "treatment" parameters such as basal rates, ICR, ISF, and insulin time action. However, things such as stress, illness, changes in exercise activity, and hormone cycles can cause changes in insulin sensitivity, which can change the effects of insulin in the body and may also affect many or all of the "treatment" parameters (ICR, ISF, etc.), which can drastically affect a patient's glucose levels. In an example, in noisy data with multiple overlapping effects, a decision support system may identify an inappropriate ISF based on occurrence of instances of lows or highs a specified amount of time (e.g., 2-4 hours) after a correction bolus, in the absence of detected basal errors or detected ICR errors. For example, the system may identify an incorrect ISF from a pattern where the glucose level is low (or high) after a correction bolus that is not in response to a meal error. In another example, if a glucose level is low (or high) after meals with a correction bolus, and the glucose excursion is not present after meals without a correction bolus, the system may determine that the error is likely attributable to an incorrect ISF.

To detect a change in insulin sensitivity, a decision support system may use a model or algorithm capable of identifying changes in glucose patterns in real time (by using retrospective data). In some examples, a decision support system may use a model or algorithm to distinguish between different types of changes in glucose patterns (e.g. insulin sensitivity, insulin delivery problems, sensor problems, etc.).

For changes in insulin sensitivity, a decision support system may propose appropriate percentage changes to all "treatment" parameters. The system may identify when insulin sensitivity goes back to baseline and propose changing parameters back to baseline. The system may, for example, distinguish between normal and abnormal states, such as normal ISF and altered ISF caused by stress, or normal insulin infusion state and abnormal infusion state. In some example, the system may use different sources of data to detect changes (e.g. sensor glucose readings, sensor raw data, finger-stick data, insulin, carbs, parameter for occlusion alarms in pumps, date of last change of infusion set) and provide guidance based on recognized patterns in the data.

Fault Detection

In addition, system "faults" such as insulin delivery problems (e.g., infusion site problems) or sensor problems can cause unexpected changes in glucose patterns. A decision support system may identify a fault using a model or algorithm based on patterns in glucose or other data. Identifying when such fault states begin and end may help a patient and the doctor of the patient take the appropriate actions to keep glucose levels within acceptable bounds, and avoid changing other factors (e.g., ISF) in an attempt to address blood glucose excursions when an unrecognized system fault is driving a glucose control problem.

In some examples, the decision support system may identify instances of recurring lows, highs, or out-of-range values that cannot be attributed to ICRs, basal rates, or ISFs with certainty and prompt for basal, ICR, or ISF "tests" to provide additional data with fewer overlapping effects to enable more accurate deduction of parameter setting problems.

Setting Basal Rates for Insulin Pumps

In some examples, the decision support system may assist with setting and fine-tuning basal rates for insulin pumps. Basal rates may differ drastically throughout the day. For example, a relatively high basal rate may be needed in early morning hours, and a lower basal rate may be needed in the afternoon. Some insulin pumps allow for setting different basal rates every 30 minutes, resulting in 48 possible basal rate parameters per day. The initial setting of these parameters can be very time consuming, and there may be a lot of uncertainty in the initial dosing. Without appropriate basal rates, it is very difficult to estimate ICR and ISF parameters and retrospectively learn these parameters. CGM data can be particularly helpful in fine tuning basal rate parameters, because the continuous readings can help identify the exact times when different basal rates are needed. In some examples, a system may determine basal rate adjustments using patterns in CGM data or blood glucose levels.

In various examples, a decision support system may combine CGM data with other data to determine or refine bolus rates. For example, a decision support system may assess estimated glucose levels received from a CGM sensor during nighttime, or during periods where other factors are not affecting glucose levels as determined from sensor or behavioral data, to determine guidance about adjustment of one or more basal rates. Night time determinations may be more accurate or more easily determined, because the problem of basal rate adjustment is not complicated by meals or physical activity. In some examples, a decision support system may guide a patient through a test protocol to limit the number of variables that may affect glucose levels (e.g., limit or regulate exercise, stress, and carbohydrate consumption) to enable accurate determination of basal rates.

Multiple Daily Injections

In some examples, a decision support system may determine guidance for multiple daily injections of insulin. The body's insulin requirements can vary significantly during the day. For example, the secretion of hormones that influence the liver's secretion of glucose (e.g., glucagon secretions by the pancreas) and the secretion of hormones that increase insulin resistance (decrease insulin sensitivity) can generate variations in insulin requirements. A pattern called the dawn phenomenon, for example, tends to raise insulin levels in the morning. This may be caused, for example, by the secretion of growth hormones or other hormones that cause blood sugar to rise, or by dietary considerations, or by the body's response to a low blood sugar in the night (Somogyi effect). These effects may be present in any patient, but may present particularly difficult problems in patients who use multiple daily injections (MDI) of insulin, because the limited number of times a day that insulin can be injected and practical lower-end limits on the size of a dose that can be delivered.

A decision support system may provide guidance (to a patient or clinician) regarding the size, type, and timing of insulin injections. Patients who use multiple daily injections (MDI) of insulin may use one or more long or intermediate-acting insulin injections to provide background insulin around the clock. The timing and dosing of intermediate or long-acting insulin depends on the onset (how quickly the insulin begins to act), peak, and duration of action of insulin, which can vary based on the type of insulin and the size of the dose. Long-acting insulins (such as insulin glargine and insulin determir) can provide a relatively unwavering flow of insulin and consistent absorption pattern. Intermediate-acting insulins can provide a peak and intermediate duration of action, which can be useful in dealing with patterns of insulin demand. NPH insulin, for example, is an intermediate-acting insulin that can provide background insulin for up to 24 hours but is much more effective (i.e. more insulin is present in the blood stream) four to eight hours after injection, and less effective 16 to 24 hours after injection.

An intermediate acting insulin such a NPH can be useful in countering the dawn phenomenon. Timing the delivery of NPH so that its peak action matches the peak basal need is important. In addition, when using an intermediate-acting insulin, it may be important to eat at certain times or conform to a meal schedule to avoid lows at certain times (e.g., when insulin action peaks). The management of glucose levels can be further complicated by the fact that some insulins can have a varied rate of absorption from day to day or can produce an unpredictable peak.

Various forms of long-acting insulin or intermediate-acting insulin can be combined to simulate the body's basal insulin secretion patterns (i.e. if diabetes was not present). For example, it may be useful to combine NPH at nighttime and glargine or detemir once daily at a lower dose to better match the body's basal requirements. However, the amount of insulin coverage provided by medium or long acting insulin or combinations thereof frequently does not properly match the body's basal insulin needs, so fine-tuning and careful timing of insulin delivery and meals can be important. Responding to day-to-day variations can also be important.

A decision support system may provide guidance in determining insulin dosing and timing to address recognized patterns (e.g., dawn phenomenon). A system may also provide guidance in responding to day-to-day variations. For example, a decision support system may detect from retrospective data one or more patterns that suggest that a multiple daily injection regimen does not adequately meet a person's basal insulin needs. This information may be provided to a patient, or may be provided to a clinician who may recommend a dosage or regimen change, or prescribe a different type or brand of insulin. In some examples, the decision support system may operate as a communication tool between a patient and clinician to enable the clinician to better understand insulin and glucose patterns (e.g., the system may provide guidance that a patient experiences a low on weekend mornings when breakfast tends to be delayed).

In some examples, a decision support system may provide tools to identify the mismatch between intermediate and long acting insulin absorption rates and basal insulin needs. For example, a mismatch may be determined from a pattern of high or low glucose levels. In some examples, the decision support system may account for other factors such as exercise and food consumption, so that patterns can be identified from noisy data. In some examples, a decision support system may identify recurring events such as hypoglycemia or hyperglycemia caused by inappropriate coverage of basal needs, and provide guidance as to possible solutions (e.g., to eat during a particular time window or consider changing a dose or injection timing).

In some examples, a decision support system may identify specific phenomena of interest, such as Dawn phenomenon and Somogyi phenomenon. In some examples, the decision support system may suggest a correction or suggest inquiry with a physician. For example, the Somogyi phenomenon may be addressed with lowering basal insulin dose, and a dawn phenomenon may be addressed by using NPH insulin that peaks in the morning or using a fast-acting dose of insulin in the morning.

In some examples, a decision support system may identify when basal needs are not being met appropriately by any combination of MDI therapy. In some examples, the decision support system may provide metrics for basal therapy success. The decision support system may, for example, evaluate whether steady blood sugar levels are being achieved while sleeping (e.g., a change of no more than 30 mg/dl assuming complicating factors are not present, e.g., when the patient did not eat, take rapid acting insulin, or exercise a short time before sleep).

A decision support system may also determine when one basal injection is not sufficient based on glucose levels and time of injection, and may determine guidance to consider (e.g., ask a clinician) an additional injection (e.g., inject basal insulin twice a day to achieve a "two-wave" pattern of insulin action) or introduction of another type of insulin (e.g., add an intermediate-acting insulin). The decision support system may include a basal test feature (e.g., an application operable on a smart device), and may identify times when a basal test is necessary or should be recommended. A basal test may, for example, include a period of relative inactivity and fasting or highly predictable or controlled eating to reveal underlying basal needs. In some examples, the system may also determine guidance as to how the basal requirements can be matched by behaviors, e.g., by combinations of basal injections, or injections in combination with meals, or exercise.

Predicting Future Glucose Levels

In some examples, a decision support system may predict blood glucose levels in advance for a specified time period (e.g., 30 minutes, several hours, or six hours). The prediction of blood glucose levels may, for example, be based upon dietary information (e.g., amount consumed, time of consumption, carbohydrate and fat or protein content, absorption rate (fast, medium, slow carbs), confidence in food estimate), bolus information (time, insulin action, and bolus type (regular or dual-wave)), basal rates, exercise, CGM data, blood glucose (e.g., finger stick data), alcohol consumption, stress factors (e.g., based on behavior or a calendar), or time of day.

The decision support system may predict glucose levels in real-time to provide advance notice of potential hypoglycemic or hyperglycemic events before they happen. The predicted glucose levels may, for example, be used to generate an alert or alarm to the user. The predicted glucose level may also be used to deliver early guidance to deliver a correction bolus before a hyperglycemic event occurs or before the patient becomes insulin resistant due to high glucose levels.

The decision support system may also determine predicted glucose levels retrospectively or hypothetically to assess treatment parameters or model parameters (to assure model parameters are stable). In some examples, the system may compare predicted values to actual values to assess model parameters.

In some examples, a system may, when confidence in the model is high (e.g., model parameters have been verified or evaluated for accuracy), use a model to test scenarios and predicted outcomes to assess whether a patient or clinician should consider adjusting treatment parameters, such as insulin-to-carb ratio or insulin sensitivity factor. For example, the system may run a variety of "tests" on the model, which would be burdensome or time consuming for the patient to actually carry out (because of the need to strictly control food, activity, or insulin delivery), and use the results of the tests to determine guidance or a timing of guidance, or to select one or more tests for the patient to actually carry out (e.g., deliver guidance "Your insulin-to-carbohydrate ratio may be incorrect: Please conduct a test at your next meal" or "Your basal rate may be incorrect: Please conduct a fasting basal test at your earliest convenience.") In an example, the system may determine what would happen (according to the model) if no meals were ingested: If the predicted blood glucose goes up, a higher basal rate may be needed, and if the predicted blood glucose goes down, a lower basal rate may be needed. In another example, if the basal rate is assumed to be correct, the system may determine what would happen if a meal is ingested: If the predicted blood glucose moves back to a target glucose level a specified amount of time (e.g. 4 hours) after a meal, the ICR may be deemed to be correct. If not, the ICR may need adjustment (e.g., a high glucose level more than four hours after a meal suggests that the ICR is too low, if the underlying basal rate is assumed to be correct). In another example, the system may determine, assuming the basal rate is correct, what would happen if a specified amount (e.g., 1 unit) of insulin were given, and the system may use this information to suggest an update to an insulin sensitivity factor. In another example, the system may assume a normal absorption meal and a correct basal rate, and the system may determine when the predicted glucose level would reach a steady value, which may be used to determine a duration of insulin on board. In some examples, the decision support system may use a model to predict recurring low or high glucose levels (e.g., using time, based on a pattern observed over time). In some examples, the decision support system may use a model to identify the Somogyi phenomenon or the dawn phenomenon.

Bolus Determinations

A decision support system may develop guidance for delivery of insulin boluses. For example, the system may also include a model or curve-based correction bolus calculator. The system may estimate an individual-specific post-meals curve, which may for example include curve estimate parameters such as peak time, peak height dependent on carbs, and curve "width" based on factors such as the content of the meal and insulin dose and duration. In some examples, the decision support system may first go through a learning period to gather data for estimating curves. The decision support system may use curve estimates in real time to predict a deviation from a meal curve estimate. A deviation from a predicted curve may be used to predict and avoid hypoglycemic events, or to predict and treat potential hyperglycemic excursions. In some examples, two or more estimated curves may be combined to account for overlapping meals. Corrections may also be made to account for deviations caused by exercise or other factors. In some examples, similar approaches may be applied to a blood glucose prediction model, where guidance is based on deviation from a model instead of deviation from a curve. For example, a deviation from an output expected by the model may indicate that an input parameter (e.g., meal size) was incorrect, and that an appropriate correction (e.g., re-estimation of meal size or a delivery of a correction bolus) is needed. The detected deviation may be provided as guidance, or additionally or alternatively the remedial step (e.g., re-estimation of meal size or delivery of a correction bolus) may be suggested as guidance.

Exercise

Exercise can affect blood sugar level quickly (e.g., almost immediately), and for up to 48 hours after exercise is completed. A decision support system may provide recommendations on what to do prior to exercising, during exercise, or after exercise. For example, a decision support system may provide guidance with respect to treatment parameters to account for the effect of exercise. A decision support system may also retrospectively learn and improve exercise recommendations. In an example, the system may receive from a user (e.g., patient) an exercise plan that may include the type of exercise that will be performed, the intensity of exercise, and the duration of exercise, and the system may develop and deliver guidance based on the received exercise plan. In an example, the system may provide guidance that the patient will need a snack of a certain size. When the exercise is pre-planned (e.g., communicated to the decision support system) at least an hour in advance, the system may suggest a temporary basal rate to account for the effect of exercise. The system may also suggest a possible temporary basal change if exercise will (or does) last for longer than one hour. Because exercise can either increase blood glucose (e.g., due to adrenaline secretion which triggers release of glycogen) or decrease blood glucose (due to activity), the system may account for the type of exercise (e.g., competitive vs. training). In some examples, the effects of exercise may be monitored using CGM or other sensors, and a change in treatment strategy may be learned for each "case" (e.g. intense morning run vs. leisurely afternoon bike ride) to improve guidance and outcomes over time.

In some examples, the system may identify optimal temporary basal percentage for different types of exercise, intensity, duration, and start time and deliver guidance that reflects this knowledge. The system may also identify optimal meal content (e.g. amount and type of carbs, or fat content) for different types of exercise, intensity, duration, and start time. In some examples, the system may also determine percent activity adjustment for entry into a bolus calculator.

Example Timelines

FIG. 3A is an illustration of an example timeline 310 associated with a patient. The patient may be engaged in an activity for a period of time, followed by a meal, for which insulin is assumed to have been delivered. After the meal, the patient is available for a period of time, followed by a meeting, and then another period of availability, and then another meeting. The decision support engine may take the patient schedule into account in determining when to deliver guidance and what guidance to deliver. For example, through access to the patient's calendar, or through learning of the patient's temporal pattern from data, the decision support engine may be aware of the period of availability after the meal and before the meeting, and accordingly deliver guidance during this availability period. The guidance may also take into account the upcoming meeting and the length of the meeting and determine guidance that is calculated to avoid an interruption during the meeting. For example, the decision support engine may suggest a large enough correction bolus to control insulin, while managing the risk of a low glucose level occurring during meeting. In another example, the decision support engine may suggest a pre-meeting snack to sustain glucose levels through the meeting. In some examples, the decision-support engine may err on the side of allowing glucose levels to drift low, if it is known (e.g. through a user-supplied preference) that it is easier to consume a small snack during a meeting than to administer insulin (e.g. if the patient uses needles or a pen to inject insulin). On the other hand, if it known that it is easier to administer insulin than consume a snack (e.g. if the user receives insulin through a pump), the guidance may be determined to err on the side of a high glucose trend.

FIG. 3B is an illustration of an example schedule 320 of a caregiver (e.g. parent) (top chart) and child patient (lower chart). In an example, the decision support engine may be aware from calendar information, user input, sensor information (e.g. GPS), or learned patterns (e.g., the periods of availability of a caregiver, and periods when the caregiver is not present or not available). The decision support engine may determine guidance to increase the likelihood of stable glucose levels when the caregiver is not available. The decision support engine may also determine a time to deliver guidance based on the availability of the caregiver, e.g. provide guidance early during a period of availability during an early part of a basketball game or defer guidance (when possible) to a period of availability at the end of the game.

FIG. 3C is an illustration of a wake/sleep state 330 of a patient. The decision support engine may determine a time to deliver guidance when the patient is awake, e.g. prior to going to sleep, or during an awakened time during the night, as may be determined, for example, using activity or other sensors in a watch, fitness tracker, or other wearable or patient-aware device.

FIG. 3D is an illustration of determination 340 of availability (or convenience) of a patient to participate in an intervention, based on other states. Initially, the patient is sleeping and not available. When sleeping ends, the patient is available until a commute begins (as determined by schedule information or GPS or connection via to a wireless connection in a vehicle). When the commute ends, the patient is available until a meeting begins. When the meeting ends, the patient becomes available again.

Determination of Guidance Timing

Figure 4:
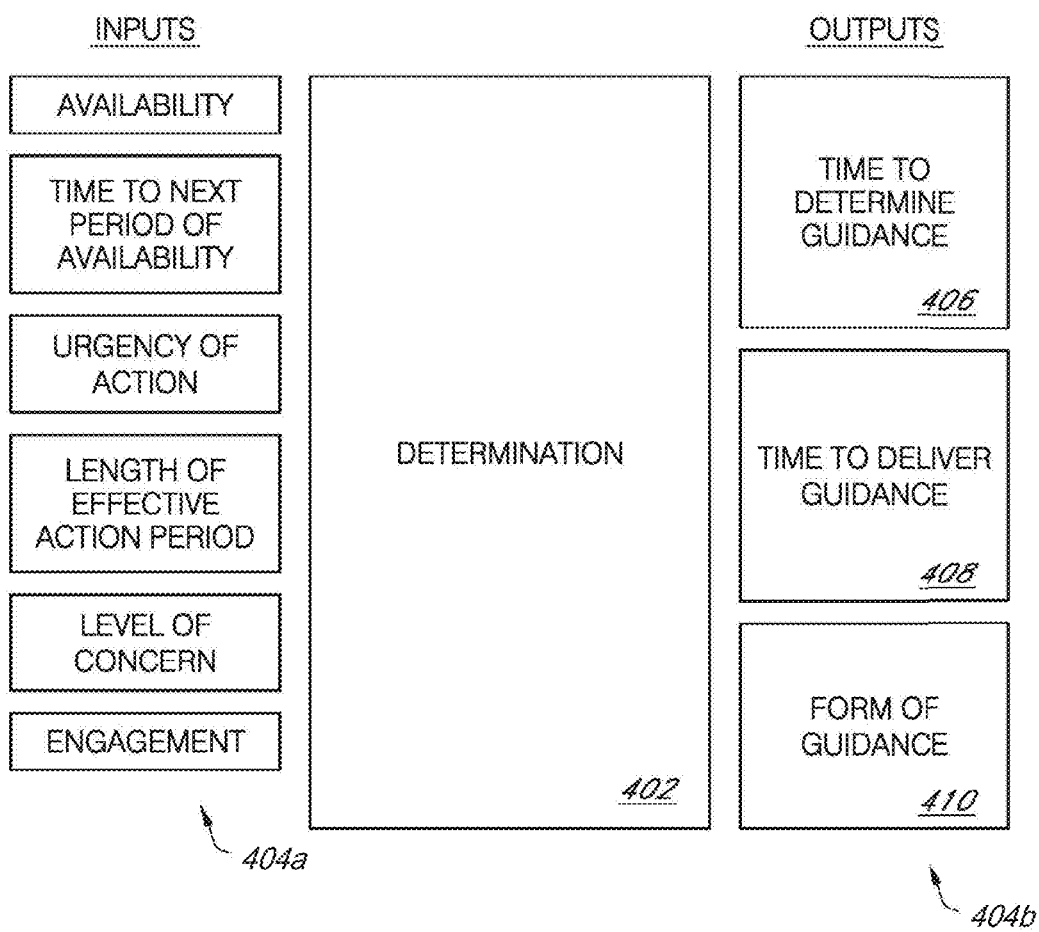
FIG. 4 is an illustration of various categories of inputs coupled to various categories of outputs through a determination step or module

FIG. 4 is a schematic representation of guidance determination. A guidance determination module 402 may receive inputs 404a and determine one or more outputs 404b relating to guidance. The determination module 402 may include a model or pattern against which inputs 404a are applied. In some examples, the determination module may include or be a portion of the behavior model. The inputs may be determined by another application, or state outputs from a model, such as a physiology or behavior model.

Availability of a user may be received as an input. Availability may include, for example, schedule availability as determined by a calendar, learned or known pattern, user input, or inference. Availability may include actual availability or accessibility (e.g., communication connection or type of connection), or user convenience, which may be determined or inferred for example, from user activity. Time to next period of availability may also be received as an input, and may be determined, for example, from a known, inferred, or user-supplied schedule or determined pattern of availability. Relatively scarce or inconsistent availability may weigh in favor of determining and delivering guidance during periods of availability. A short wait until the next period of availability may weigh in favor of not delivering guidance during a present availability window, because another availability window will soon be open. A long wait until the next period of availability may weigh in favor of delivering guidance during a present availability window, because if the guidance is not delivered in the present window, a long wait will be required to deliver guidance, or the system will need to interrupt the user at an inconvenient time.

Urgency of action may also be received as an input. Urgency of action may depend, for example, on the physiological state of the patient or the nature of the guidance, or both. For example, urgency of action may be high when a user is rapidly trending toward a low blood glucose level, particularly in circumstances when the user may not be aware of the trend. Urgency of action may be moderate when a user is slowly trending toward a low blood glucose level, or when a user is trending at a moderate rate toward a high blood glucose level. Urgency of action may be relatively low when action is desired, but physiologic risk to the patient is low. In other examples, urgency of action may be determined to be high when ingestion of carbs is needed to avoid a low blood glucose level and may be determined to be moderate when injection of insulin is needed, and may be low when testing is needed (e.g. finger prick blood glucose testing, or temperature or heart rate) to confirm a physiologic condition or calibrate a sensor (e.g. glucose sensor calibration). High urgency of action may weigh in favor of near-term delivery of guidance, whereas low urgency may weigh in favor of waiting until a future period of availability, e.g., to avoid guidance-fatigue or excessive interruption by the user.

The length of a period of an effective action period may also be received as input. In an example, it may be determined that ingestion of carbohydrates is required within a short period (e.g., a 5-minute period or 10-minute period). In another example, it may be determined that injection of insulin is needed within a moderate period (e.g., a 20-minute period). In some examples, the period may be a fuzzy input, e.g., the length of the period may not be exact. In some examples, the general size of the action window may be understood, as a reflection the variance in action windows for therapeutic or sensor input actions.

Level of concern may also be received as an input. The level of concern of a patient or caregiver may vary amongst patients/caregivers and may vary depending on the particular situation. Level of concern may, for example, be determined using patient-supplied information, or learned from data, or received from a model (e.g., a behavior model). High level of concern by a particular user, or about a particular situation (e.g. combination of physiologic states) may weigh in favor of more near-term determination and delivery of guidance, whereas low level of concern may weigh in favor of deferred determination and delivery of guidance. Engagement may also be received as an input. As described above, level of engagement may be determined from user responsiveness to alerts or guidance, including for example, the frequency or consistency of checking of sensor data (e.g., blood glucose levels), or manner of engagement (e.g. viewing notification only vs. full data view, or watch vs. smartphone vs. computer). In some examples, a high level of engagement by a particular user (suggesting concern, availability, or attentiveness) may weigh in favor of more near-term determination and delivery of guidance, whereas low level of engagement may weigh in favor of deferred determination and delivery of guidance. In other words, to some extent, the level of availability or concern may be inferred from engagement. For example, the low level of engagement may result in a lower frequency of guidance, for example, so as to avoid overwhelming the user. In other examples, a low level of concern by a particular user, or about a particular situation may weigh in favor of more near-term determination and delivery of guidance, for example because it may be determined that the user is likely not aware of a potential problem due to the lack of engagement, whereas a high level of concern may weigh in favor of deferred determination and delivery of guidance, for example because the user may already be aware of a potential problem and highly engaged in monitoring or resolving the problem.

Two or more of the inputs may be used together to determine a time to determine guidance 406, a time to deliver guidance 408, a form of guidance 410, or combinations thereof. A time to determine guidance 406 and time to deliver guidance 408 may be related, e.g., the guidance may be determined a short time before the time to deliver guidance 408 to assure that the determined guidance reflects up-to-date real-time data. In an example, the time to determine guidance 406 may, for example, be deferred when the length of effective action period or the time to the next period of availability is relatively long, to allow for collection of additional data to refine the guidance or the accuracy of states from which the guidance is determined. In some examples, when a relatively short window of availability is open or approaching, guidance may be determined early, even though additional data would normally be desired to get an accurate interpretation of the physiologic state, to enable delivery of guidance (and time to act upon the guidance) before the window closes. In another example, guidance may be deferred where a time period to a next window of availability is relatively short. In some examples, the determination module applies weights to the factors to determine whether or when to determine guidance. In some examples, the determine module determines projected future states, or interacts with other modules or models (e.g., the physiologic model) to determine a projected future state and balance the various inputs against physiologic risks. In some examples, the determination module receives inputs for a number of future times, or determines projected future states, and determines an acceptable or optimal time or range of time to determine or deliver guidance. For example, the module may determine that guidance is not necessary at a present time (e.g. 4 PM), but that guidance should be delivered at a future time (e.g. 6-6:30 PM). In some examples, the module may reassess the determination as new information becomes available, e.g. as the urgency of action shifts in response to an evolving physiologic state, or as level of engagement changes, or as availability schedule or pattern changes.

Figure 5A:
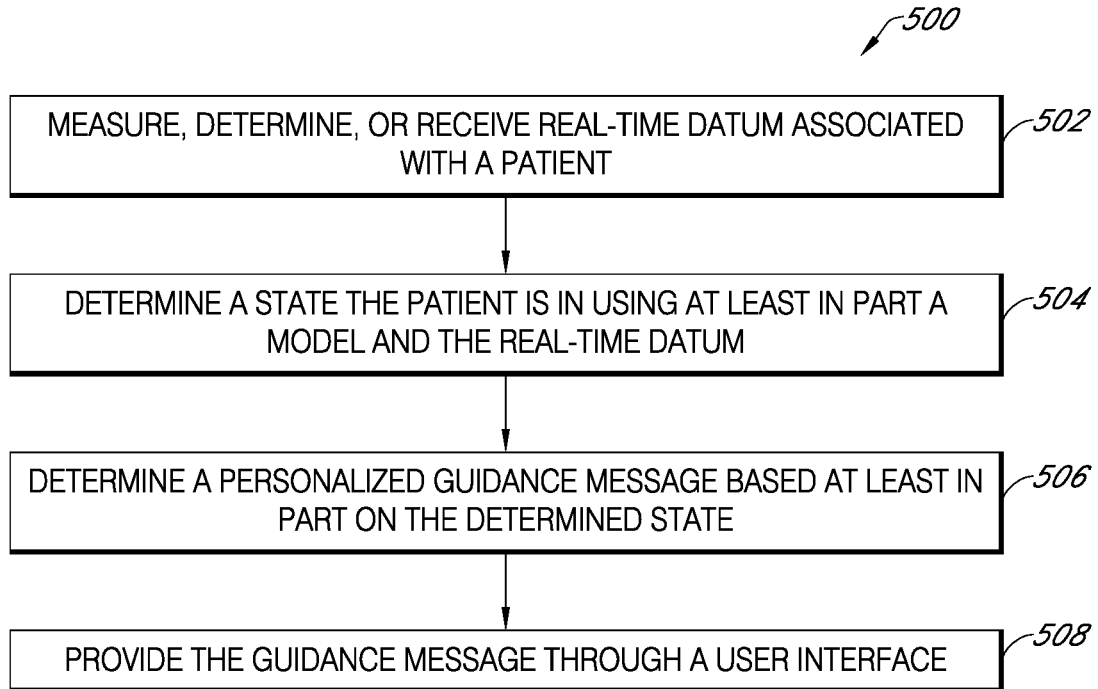
FIGS. 5A, 5B, and FIGS. 6-13 are flowcharts that illustrate example methods of determining user guidance.

FIG. 5A is a flowchart that illustrates an example method 500 of delivering guidance, such as physiologic glucose concentration management guidance. The method may provide guidance to facilitate delivery of therapy such as insulin delivery, carbohydrate ingestion, or physical exertion to manage glucose levels in a diabetic patient.

At step 502, a real-time datum associated with a patient is measured, determined, or received. The real-time datum may, for example, be a reading from a glucose sensor, e.g. a real-time datum received from a continuous glucose monitoring system that intermittently measures a glucose level and provides the glucose level information through a network connection. In an example, it is determined that a user has just eaten a particular meal (e.g. 60 g carbohydrate) for example by meal detection, user entry, or other pattern detection. In another example, it is determined that a user is about to take the weekly run of the user, as determined by pattern recognition of calendar entries. In other examples, the real-time datum may also be a time, a deviation from an expected behavioral pattern, a change of state (e.g. a change of physiologic state determined using a model), an indication that a mealtime is imminent, a time of day, a characteristic or signature signal measured by an accelerometer, a location determined by a GPS circuit, or a request for decision support received through a user interface. In various examples, the first real-time datum may be measured, received, or determined by a smart phone, determined by a wearable device such as a watch, or determined by a wearable device in combination with a smart phone. In some examples, the first real-time datum may be measured, received, or determined by an external device, such as a computer.

At 504, a state the patient is in is determined. The state may be determined using a model and the real-time datum, e.g. by applying the real-time datum to the model.

The model may, for example, include a state indicative of a convenience or availability of the patient to participate in an intervention. For example, information (e.g. availability) from a calendar associated with the patient, or associated with a caregiver, may be applied to a model. In some examples, sensor information (e.g. accelerometer information indicating activity level) or pattern information (e.g. indicating wake/sleep cycles or periods of exercise or periods of transit, e.g. driving) may be applied to a model. A state indicating the availability or convenience of performing an intervention such as administering insulin or consuming carbohydrates or partaking in physical activity may be determined by applying the real-time datum to the model. In some examples, the model may include a patient physiology model, and determining a state the patient is in may be based at least on applying the first real-time datum to the patient physiology model. In some examples, the state is an insulin sensitivity. In an example, exercise is detected, and an insulin sensitivity is determined based upon a known pattern of user glycemic response to exercise.

The model may additionally or alternatively include a behavior model. The behavior model may, for example, be based on one or more machine-learned characteristics of the patient. The one or more machine-learned characteristics may be based on a behavioral or contextual pattern. In some examples, the behavior model may be based on a set of one or more steps determined to be likely to be performed by the patient, or one or more objectives determined to be likely attainable by the patient, or both.

In some examples, the behavior model may include a pattern. In an example configuration, a patient physiology model is based on a physiological pattern, and a behavior model is based on a behavioral pattern. In some examples, the first real-time datum may indicate a deviation from an expected behavioral pattern. For example, the first real-time datum may indicate a deviation in meal-time, a missed, early, or late insulin dose, a variation in physical activity (e.g. missed workout or atypical workout), or an early or late awakening. In some examples, the behavior model may indicate a tendency to over-correct at a meal associated with a meal time, the first real-time datum indicates that a mealtime is imminent, and the guidance message may correspond to a lessened overcorrection (e.g. smaller insulin dose or different combination of basal and bolus doses) at the mealtime.

In some examples, the behavioral pattern may include a long-term behavioral pattern based on long-term patterns of behavior and a short-term behavioral pattern associated with current behavior. The behavior model may be based on both long-term behavioral patterns and short-term behavioral patterns. In some examples, the short-term behavioral pattern may be based on one or more selected from the group consisting of: engagement with mobile device, accelerometer data, frequency of checking glucose concentration, calendar data, and combinations of these.

In some examples, a determining a state may also be based on a measurement model. For example, the measurement model may be based on a continuous glucose concentration monitoring system associated with the patient. The measurement model may, for example, include an accuracy or other state relating to the glucose measurement. In some examples, the method 500 may also include measuring glucose concentration data subsequent to the rendering a guidance message and using the measured subsequent data to improve one or more of the models. For example, the glucose concentration data measured subsequent to the rendering may be fed back to a measurement model or the behavior model or the patient physiology model, or to a combination thereof.

At 506, a personalized guidance message may be determined based at least in part on the determined state. The personalized guidance may, for example, be a therapy recommendation, such as an instruction to administer a specified amount (e.g., one unit) of insulin or an instruction to eat food that contains a specified amount of carbohydrates (e.g. five grams of carbohydrates). In some examples, the guidance message may be based at least in part on a projected transition to the undesirable physiologic state, such as a high glucose level or a low glucose level. Determining a guidance message may be further based on a timing of the determining the guidance message or a time associated with the determined state. For example, the personalized guidance message may be based on timing information obtained from a calendar or pattern or model of an upcoming event. The guidance message determined at step 506 may provide information to prepare or inform the user for the upcoming event, such as glucose dosing information or carbohydrate consumption information, or "Consider dosing with insulin prior to your upcoming two-hour meeting" or "Consume carbohydrates prior to your commute home to avoid a potential low glucose level during your commute." In some examples, the guidance message may be based at least in part on a determination that a projected transition from a present state to a projected state is a low-probability transition. For example, state-transition probabilities may be known or learned from data, and real-time and other data may indicate that the conditions are present for a low-probability transition. This determination may form the basis for guidance to the patient, and may be particularly useful, for example in the circumstance where the decision guidance engine may provide an alert about risks for which the patient may not be aware.

In some examples, a system detects a state of having missed an exercise session, or a series of missed exercise sessions, or a trend toward shorter or less intense exercise sessions. Physical exertion by a patient tends to generate increased metabolic drive, which may increase glucose consumption. A missed or reduced exercise session may result in a lower metabolic drive and a reduced need for calories, or an increased need for insulin to compensate for the lower metabolic drive.

The decision guidance engine may also recognize a confluence of factors, e.g. higher-than-normal activity combined with lower than normal food consumption, or other patterns such as stress-inducers or lack thereof, travel, sleep disruption, sickness/health, or atypical meal times, and determine that a low-probability (given normal condition) state transition (e.g. from normal too high or low blood glucose levels) may occur. Such a determination could lead to determining guidance such as "You may experience an atypical low blood glucose level tonight" or "You may experience an atypical high blood glucose level this morning" or "Your insulin needs may be higher than normal today." The guidance may provide details about the reasoning for the guidance (e.g. " . . . because you missed some workouts") or may simply notify the user about the physiologic result.

At 508, the guidance message may be provided to the user, such as a patient or caregiver, through a user interface, such as a screen or speaker of a mobile device, a speaker or display on a vehicle. In some examples, the manner or time of delivery of the guidance message may be determined in part by time (e.g. clock time or time of day), for example to account for the patient's work, sleep, dining, or commuting schedule. In an example, providing the guidance message may include displaying the therapy recommendation at a time calculated to be useful to the user. In an example, the guidance message may be provided in advance of a scheduled event, such as a meeting. For example, when it is known that the user is going into a three-hour meeting, a therapy recommendation may be given before the meeting, as opposed to waiting for a more accurate recommendation to develop or to be determinable. In another example, providing the guidance message may include providing the message at a time calculated to be useful to the user. For example, when a user is about to go for the usual run of the user, a guidance message with a treatment or monitoring recommendation may be provided before the run starts, as opposed to when the user trends toward a low blood glucose level.

FIG. 5B

Figure 5B:
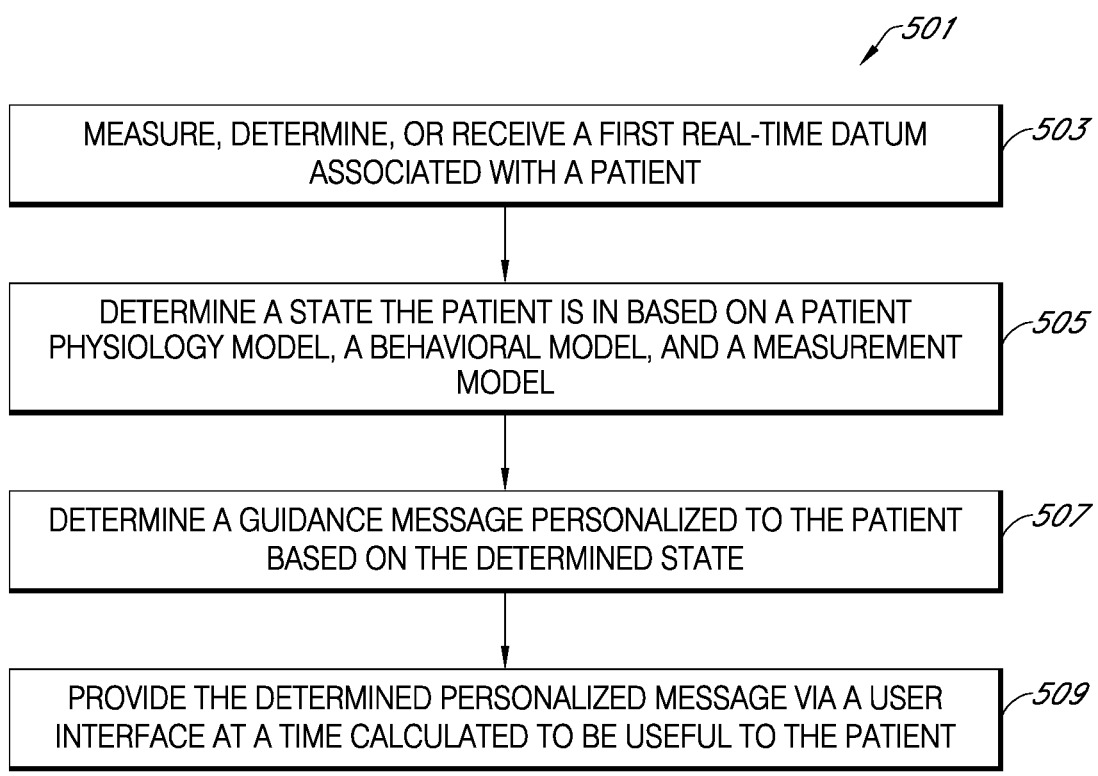

FIG. 5B is a flowchart illustration of an example method 501 of determining and rendering a calculated guidance message personalized and useful to a patient in the therapeutic management of the diabetes of the user, at a time calculated to be useful to the patient. The examples discussed in reference to FIG. 5A may also be applied to the method of FIG. 5B.

At 503, the method may include measuring, determining, or receiving a first real-time datum associated with the patient. The first real-time datum may, for example, be a glucose concentration value, a time of day, meal information, a request for advice received through a user interface (e.g. via a smartphone app), activity information (e.g. from a fitness tracker or watch, or insulin delivery information, which may be received via a user interface or from a smart device such as a pen or pump.

At 505, the method may include, using a model, determining a state the patient is in. For example, the determining may be based on a patient physiology model, a behavioral model, and a measurement model. The state may be determined by applying the real-time datum to the patient physiology model and the behavioral model. The patient physiology model may, for example, be a state model that includes one or more of a glucose concentration state, an insulin-on-board state, an insulin sensitivity state, an energy absorption state, or an energy exertion state. A particular state may be determined by features of available input (e.g. time of day, glucose level, prior activity.)

At 507, the method may include determining a guidance message. The guidance message may be personalized to the patient based on at least the determined state.

At 509, the method may include providing the determined personalized guidance message via a user interface, such that the rendering occurs at a time calculated to be useful to the patient in the therapeutic management of the diabetes of the patient. Providing the determined personalized guidance message may include rendering the personalized guidance message on a user interface.

The method may also include learning the model from a set of input data. The set of input data may include a clock time, a time of day, glucose concentration levels, insulin on board, patient activity, patient wellness, day of week, day of month, day of year, location, food consumed, or beverage consumed, and information received through a user interface. Other input data are also possible, including for example the information described with respect to FIGS. 2B and 14-16.

The learning of the model may occur before, or after, the receiving of the real-time datum. For example, the method may further include determining a deviation from an expected state after delivering the personalized guidance message, and adapting the model based on additional input information.

FIG. 6

Figure 6:
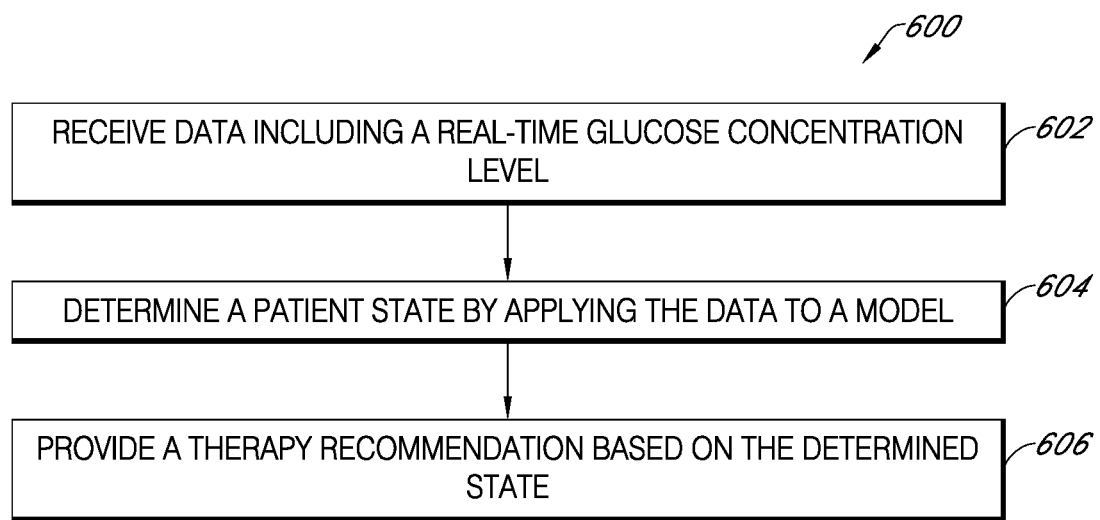

FIG. 6 is a flowchart that illustrates an example method 600 of determining and rendering a calculated guidance message personalized and useful to a patient in the therapeutic management of their diabetes. At step 602, the method 600 may include receiving data relating to a patient, the data including a real-time glucose concentration level. The real-time glucose concentration level may be received, for example, from a glucose sensor, such as a continuous glucose monitoring system.

At 604, a patient state may be determined by applying the data to a state model. The patient state may, for example, be a physiologic state, such as any one of the physiologic states described above. For example, the state may include an insulin state, such as an insulin on board state, an insulin sensitivity state, an insulin action time state, or a combination thereof. The state model may also include a behavioral or contextual state or a measurement state. The state model may, for example be a probabilistic state model. The state model may include state transition probabilities that are learned from retrospective data. In some examples, the model includes a multitude of sources, and is informed using retrospective data, or data captured in real time. The model may also include probabilities, such as the probability of state transitions, or combinations of state transitions. In some examples, a state or number of states may be determined based upon CGM data and other input data to determine a patient state. In other words, the system may work backwards through the model to determine what combination of parameters is most likely to provide a current CGM value of X. This combination of parameters (e.g. states) may be considered "the state the patient is in."

At 606, a therapy recommendation based on the determined state may be provided. The therapy recommendation may include, for example, guidance regarding delivery of insulin, consumption of carbohydrates, protein, fat, or other nourishment or other food or drink. The therapy recommendation may be delivered to the patient or a caregiver, e.g. via an electronic communication delivered through a visual user interface (e.g. screen), speaker, or other communication mechanism. The method may further include refining the state model using data received after delivery of the therapy recommendation. For example, physiologic data or state changes may be entered into the model, and the model may learn from the actual data and refine the model based on input conditions and actual outputs. The system may also refine the determination of particular states, or refine the determination of guidance, in view of the physiologic results of prior guidance.

FIG. 7

Figure 7:
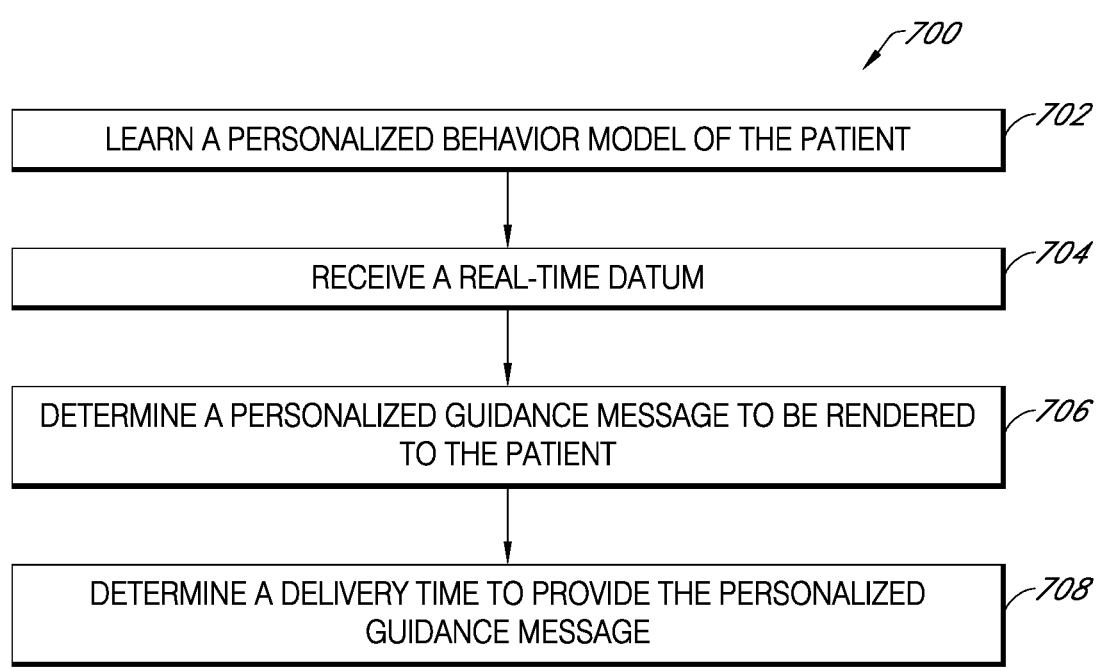

FIG. 7 is a flowchart illustration of a method 700 of determining and delivering a calculated guidance message that may be personalized and useful to a patient in therapeutic management of the diabetes of the patient.

The method may include at 702 learning a personalized behavior model of the patient. The learning may, for example, be based on a preexisting data set, data captured in real-time, or a combination thereof. Learning the model may include learning both the physiology of the patient, and the behavior of the patient, both of which may be characterized as states. Learning the personalized behavior model of a patient may include machine learning one or more characteristics of the patient, such as a physiological pattern, a contextual pattern, or a behavioral pattern, or a combination of these patterns.

The method may also include, at 704, receiving a real-time datum. The real-time datum may include any of the examples describe herein, such as a CGM sensor datum, location, network connection, or physiologic sensor datum.

The method may also include, at 706, determining a personalized guidance message to be rendered to the patient. The determining of the personalized guidance message may be based at least in part on the time of determination of the personalized guidance message and the personalized behavior model of the patient. The method may also include, at 708, determining a delivery time to provide the personalized guidance message using the learned personalized behavior model, wherein the delivery time is calculated to be useful to the patient in the therapeutic management of his or her diabetes. The method may also include delivering the personalized guidance message at the delivery time.

FIG. 8

Figure 8:
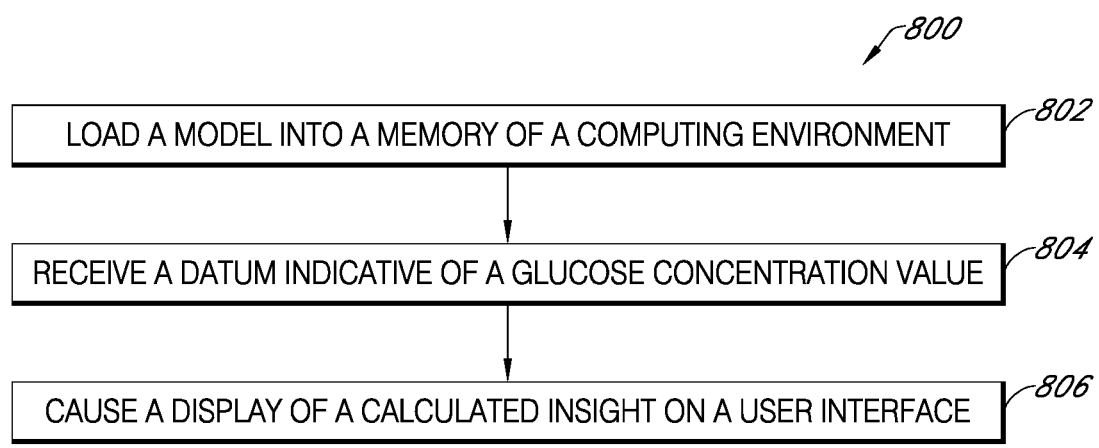

FIG. 8 is a flowchart illustration of an example method 800 of providing decision support functionality for a user. The method may include, at 802, loading a model into a memory of a computing environment. The method may also include, at 804, receiving a datum indicative of a glucose concentration value of the user. The method may also include, at 806, causing a display of a calculated insight on a user interface of the computing environment. The insight may for example be calculated using at least the model and the datum indicative of the glucose concentration value. In some examples, a user request may trigger the causing of display of the calculated insight. The user request may, for example, be associated with data entry of a planned activity.

The calculated insight may indicate a user act calculated by one or more of the models to result in a desired outcome associated with the glucose concentration value, such as maintaining the glucose concentration level (or a rate of change thereof) in a target range, or above or below a certain level. The planned activity may, for example, be a meal, and the calculated insight may be a calculated or predicted effect of the meal on the glucose concentration value, or a strategy (e.g., insulin delivery or activity or both) to manage glucose concentration levels after the meal. In some examples, the calculated insight may include an interactive recommendation and at least one factor used in determining the interactive recommendation.

In some examples, the causing a display of the insight may be initiated by an occurrence of an event that matches a predetermined condition, such as a blood glucose level or trend, or an arrival at a destination as determined by a GPS system, or an event inferred from a pattern or determined using calendar information.

In some examples, the causing a display of the guidance may be initiated by an occurrence of an event that matches a calculated condition. The calculated condition may be calculated based at least in part on the model, or the datum indicative of the glucose concentration value, or a combination thereof. For example, when a therapy adjustment exposes the user to more risk than was present before the therapy adjustment, alerts and/or alarms may be adjusted to have additional sensitivity for a period of time following the therapy adjustment. In another example, detecting when a time period exists following a potential treatment decision that triggers a more frequent instantiation of a CGM app than prior to the potential treatment decision may lead to the messaging frequency of a decision support application being increased.

FIG. 9

Figure 9:
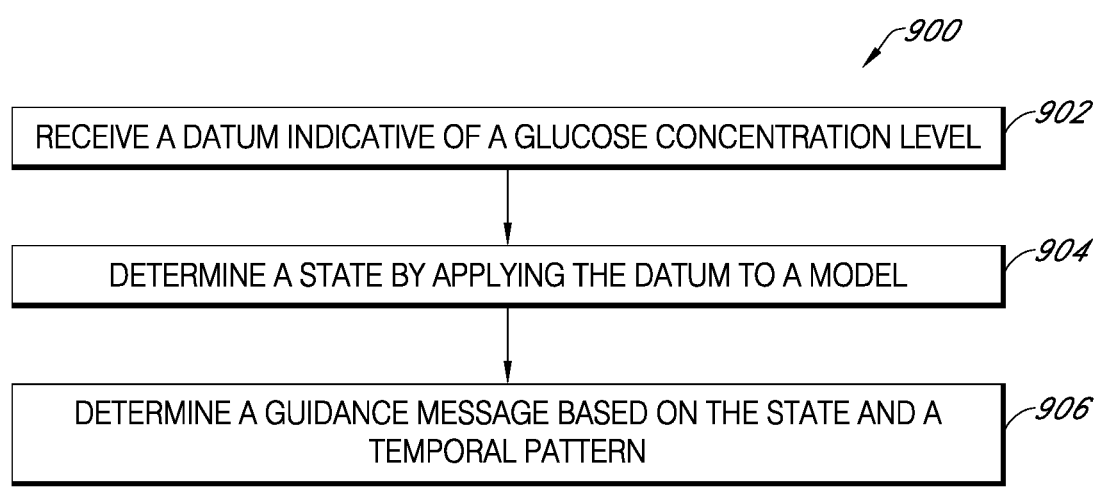

FIG. 9 is a flowchart illustration of a method 900 of delivering physiologic glucose concentration management guidance. At step 902, the method may include receiving a datum indicative of a glucose concentration level. At step 904, the method may include determining a state by applying the datum to a model. At step 906, the method may include determining a guidance message based on the state and a temporal pattern. The temporal pattern may include, for example, a learned temporal pattern or a user-defined schedule (e.g. calendar of the patient or a caregiver). The pattern may include a pattern of one or more states correlated to time, or typical blood glucose concentration levels, ranges, or patterns correlated to time or events.

FIG. 10

Figure 10:
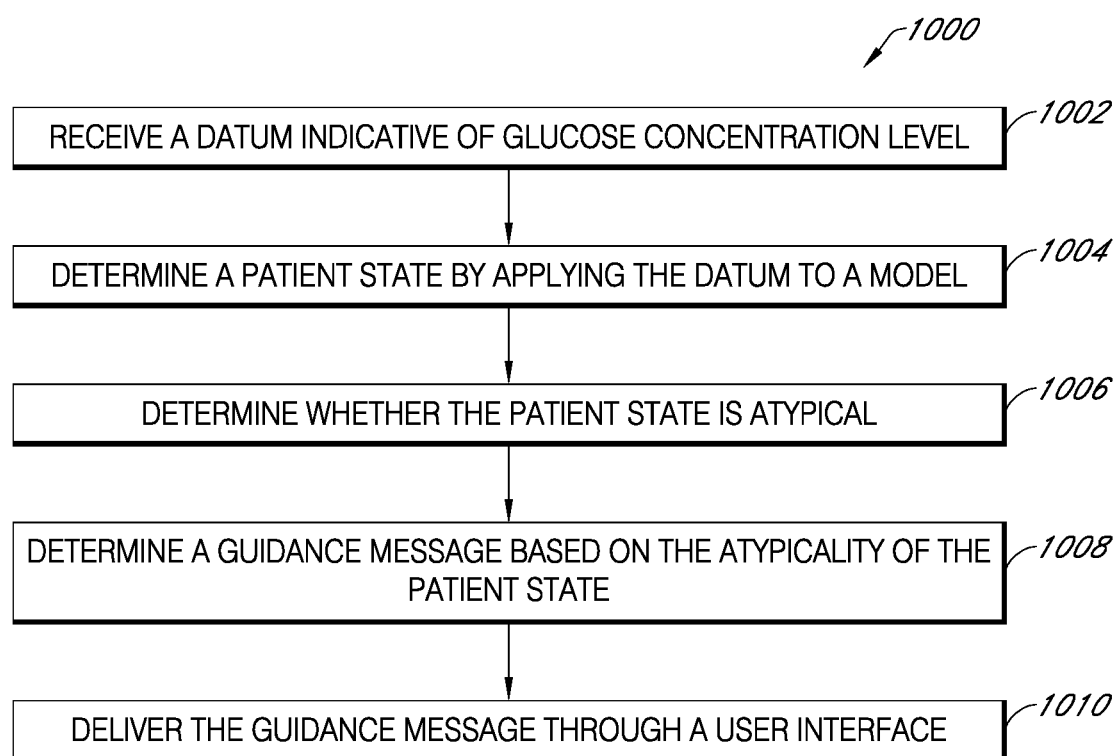

FIG. 10 is a flowchart illustration of a method 1000 of delivering physiologic glucose concentration management guidance. The method 1000 may include, at step 1002, receiving a datum indicative of a glucose concentration. At step 1004, the method may include determining a patient state by applying the datum to a model.

At step 1006, the method may include determining whether the patient state is atypical. Determining whether the patient state is atypical may include determining whether the patient state is atypical for a given set of conditions, determining whether a low-likelihood state transition has occurred, and determining whether a low-likelihood state transition is projected to occur. In an example, determining a patient state includes determining a physiological state and a behavioral state, and determining whether the physiological state is atypical for the determined behavioral state. In further examples, determining whether the patient state is atypical includes identifying a blood glucose concentration level that deviates from a controlled blood glucose concentration range a time or in a circumstance when blood glucose concentration is typically in a controlled range, identifying a blood glucose concentration trend leading to a high or low blood glucose concentration state a time or in a circumstance when blood glucose concentration is typically in a controlled range, or includes anticipating a shift to a low blood glucose concentration state at a time or in a circumstance when blood glucose concentration is typically well controlled.

At step 1008, the method may include determining a guidance message based on the atypicality of the patient state; and at step 1010, delivering the guidance message through a user interface.

FIG. 11

Figure 11:
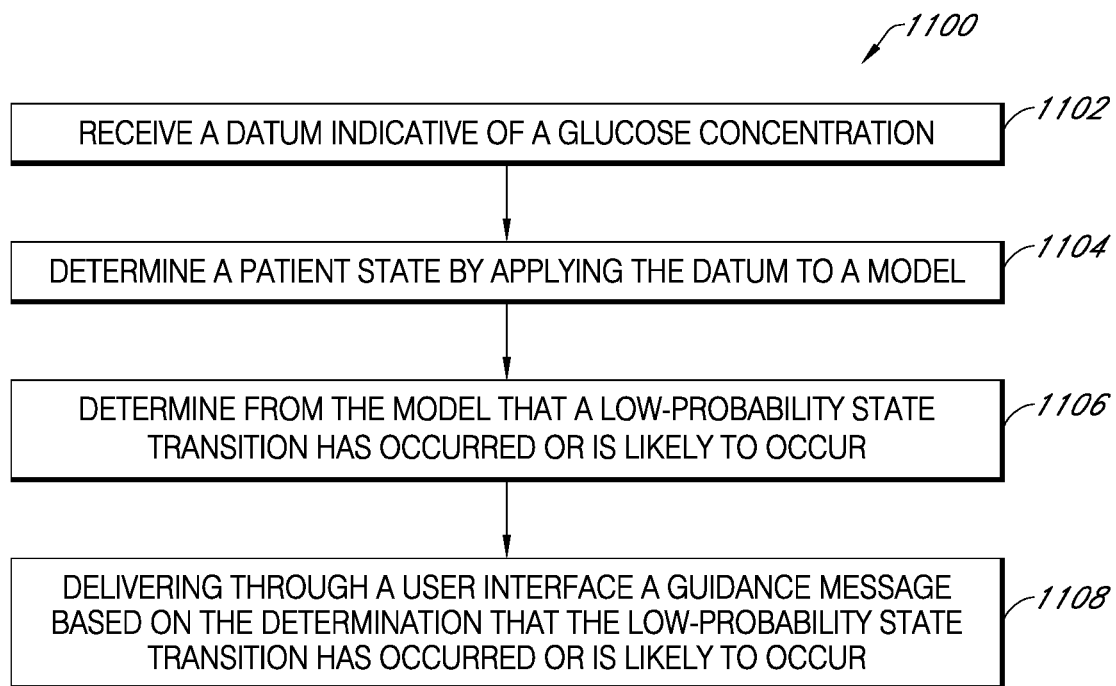

FIG. 11 is a flowchart illustration of a method 1100 of delivering physiologic glucose concentration management guidance through steps 1102, 1104, 1106, and 1108. The method may include receiving a datum indicative of a glucose concentration, determining a patient state by applying the datum to a model, determining from the model that a low-probability state transition has occurred or is likely to occur, and delivering through a user interface a guidance message based on the determination that the low-probability state transition has occurred or is likely to occur. For example, a pattern may be recognized for which, under general conditions, the transition to a particular state is a low probability, but under specific conditions as indicated by real-time data or user input, a pattern is recognized for which the transition is actually likely. For example, the method may include alerting a user that an atypical state is likely, when glucose levels are normally controlled at that time. For example, the user may be alerted of an anticipated low glucose level following exercise. Exercise can lead to a low glucose level several hours after the exercise is completed (e.g., due to increased insulin sensitivity or restoration of glycogen reserves). The user may be alerted of the possibility or likelihood of such a "late low." The alert may be delivered or prioritized if the low is calculated to occur at during sleep or at an inconvenient time. In some examples, the alert may be delivered at a time that is calculated to be useful to the user, such as at time before the patient is expected to go to sleep, to avoid waking the patient or a caregiver.

FIG. 12

Figure 12:
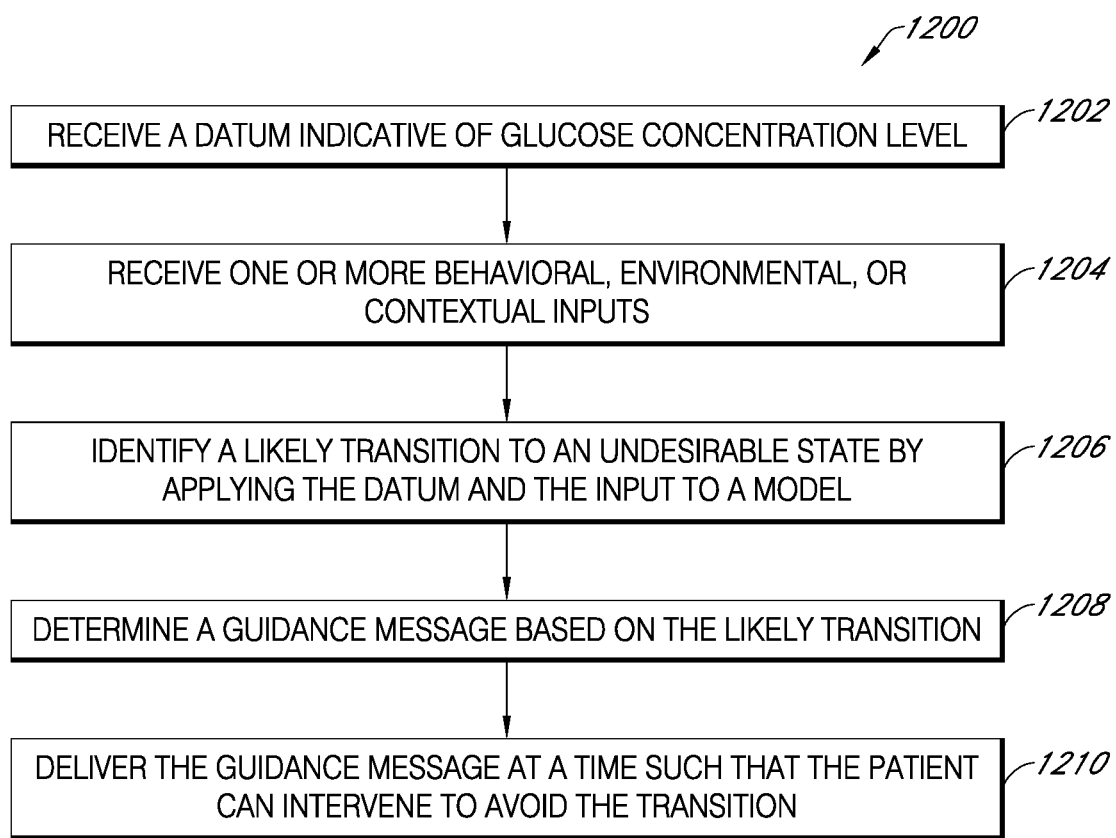

FIG. 12 is a flowchart illustrating a method 1200 of delivering physiologic glucose concentration management guidance. The method may include, at 1202, receiving a datum indicative of a glucose concentration, at 1204, receiving one or more behavioral, environmental or contextual inputs, at 1206, identifying a likely transition to an undesirable patient state by applying the datum and the one or more behavioral, environmental or contextual input to a model, at 1208, determining a guidance message based on the likely transition to an undesirable patient state; and at 1210, delivering the guidance message, wherein the guidance message is determined and delivered at a time such that the patient can intervene to avoid the transition to an undesirable patient state.

FIG. 13

Figure 13:
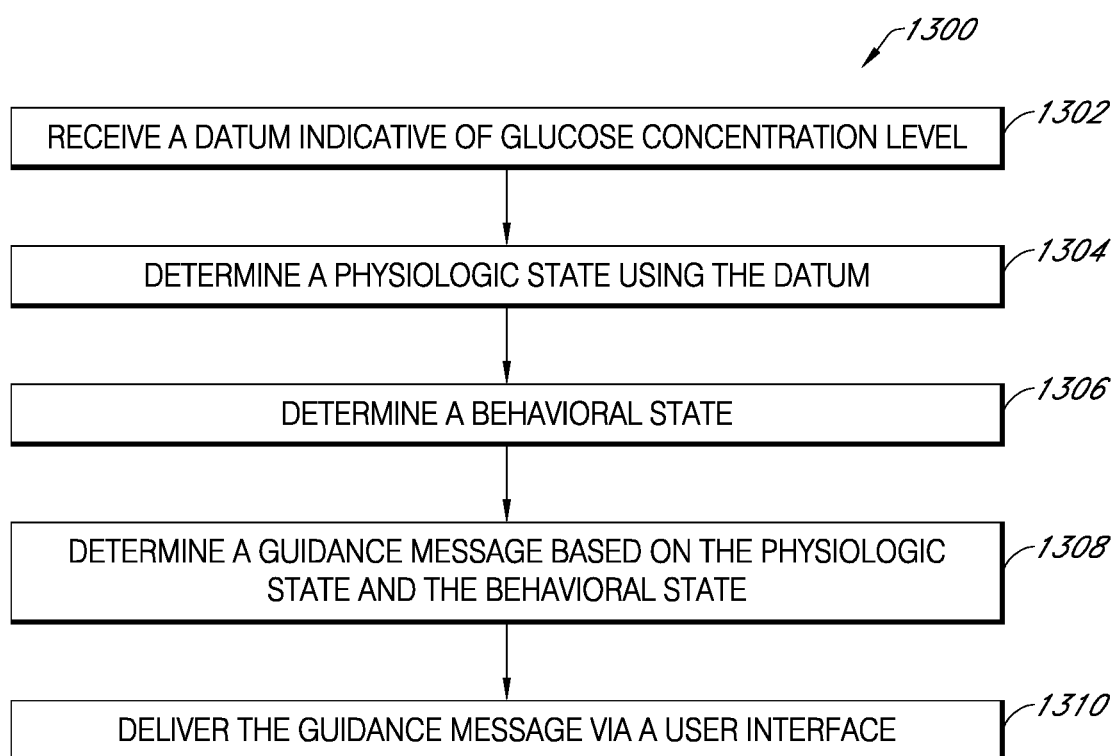

FIG. 13 is a flowchart illustration of a method 1300 of delivering physiologic glucose concentration management. The method may include, at 1302, receiving a datum indicative of a glucose concentration, at 1304, determining a physiologic state using the datum, at 1306, determining a behavioral state, at 1308, determining a guidance message based on the physiologic state and the behavioral state, and, at 1310, delivering the guidance message using a user interface.

Example Inputs and Outputs—FIG. 14-16

The flowchart 650 of FIG. 14 indicates ways of quantifying non-crisp inputs. In particular, upon reception of a non-crisp input (step 219), one way of quantifying the same is performing a step of natural language processing (step 221) on the input to determine a "crisp" equivalent. For example, if the user indicates qualitatively that the user consumed a glass of orange juice, natural language processing may determine how many carbs are involved in a glass of orange juice, thus translating the input from non-crisp to crisp. Historical pattern data may also be employed in this regard. Similar such natural language processing may be employed to determine the crisp nutritional content of an input such as "I had a quarter pounder at McDonald's®". Social networks and social media may also be employed (step 223) to give context to non-crisp inputs or to otherwise tighten down values pertaining to non-crisp inputs. Big data may also be employed (step 225) to give context and crisp values to non-crisp inputs. For example, population data may be employed to determine what a particular user means by a particular phrase or indication of a parameter, e.g., by analysis of cohort data, and the same may be employed along with any of the other techniques to render a crisp version of the input that will result in (step 227) quantifiable criteria that may be employed to influence decision-support.

Particular and other aspects of inputs are described below in the Inputs section.

However, prior to a general discussion of inputs, and referring to FIG. 15, particular types of relationships are shown, and a particular relationship is shown by the relationship 231 between a food sensitivity 233*d* and a meal bolus 235*a*. Other relationships may also be determined using systems and methods according to present principles, between inputs 233*a*-233*e* (only a sampling of such inputs is shown) and various outcomes or in particular outputs 235*a*-235*e* (again, only a sampling of such outputs are shown). Processing steps 237 are indicated to show how the correlative parameter, e.g., food sensitivity 233*d*, is used along with a real-time input (not shown) within the processing steps 237 to result in a therapy recommendation of a meal bolus 235*a*. Particular examples of these inputs and outputs are described below in the Examples section.

The identification of the correlative parameter and the lifestyle/situational parameter, as well as subsequent processing steps, can be performed in a number of ways. For example, the steps can include factors from various locations, including social networks, user-entered data, sensor data, data from user devices, population or big data, and so on. The processing and identification may include Bayesian analysis or the like, e.g., to identify strong connectors which are parameters or variables that bear a strong relationship to each other. Where multiple parameters are employed, the same may include multiple parameters relating to the same event, e.g., both intensity and duration of exercise. The processing and identification may include multiple steps, e.g., a first step of processing "internal data" for that patient, and a subsequent step of performing some processing in the cloud, with "big" data, e.g., using prepackaged subroutines and case-based reasoning. For example, case-based reasoning may be employed to determine what happened to the user in other like situations, or what happened to other like users in other like situations. As smart devices become even more computationally capable, much of the machine learning may happen on such devices. However, much of the current processing can happen in the cloud, and such processing may result in significant amounts of machine learning. In other words, the system learns how one element or "affector" X affects the patient, e.g., how anabolic exercise may impact insulin sensitivity. In this example, if a pump action was initiated with the bolus but did not consider the impact of exercise, and then the user goes for a run, systems and methods according to present principles may detect this sequence of events and notify the user to "expect a drop" or may provide a recommendation such as "you should eat something now".

As noted above, a final step in this method is modifying the input or output interface based on the identified correlative parameter or state as well as on a real-time input. The real-time input may include a lifestyle or behavioral or situational parameter, e.g., a time of day, an event about to be undertaken as determined by a clock or calendar application or user input, glucose value, and so on. In other words, the machine/human interface is modified by the decision-support application/functionality, e.g., on the smart device, smart phone, smart watch, and/or as part of the input user interface or output user interface of any of these devices, based on the results of the above steps. For example, the output user interface, i.e., the type, format, and content of the output, may then depend on the lifestyle/ situational context as well as on the parameterized model and/or the user-defined functionality. It should be noted that a specific user-defined functionality, e.g., a lifestyle goal, need not be employed in every implementation, although such may be advantageously used to guide certain therapy recommendations.

In modifying the machine human interface, just as inputs may be categorized or "fuzzified", outputs may be provided in categories or "fuzzifications" as well, and such is particularly true if the output is simply to be rendered on a user interface of a display. For example, if the therapy recommendation is to suggest that a user have a large glass of orange juice, or eat a medium apple, the user may find such a recommendation more useful than a recommendation to eat a certain amount of carbohydrates. Of course, if the output includes an output to a pump or pen, no such "fuzzification" is necessary and as much accuracy as possible is generally desired.

FIG. 15—Outputs

Exemplary outputs are as illustrated in FIG. 15, e.g., a recommendation of a type, amount, and timing of a meal bolus 235*a*, a recommendation of a type, amount, and timing of a correction bolus 235*b*, a recommendation of a type, amount, and timing of a meal 235*c*, a change in the user interface 235*d*, e.g., providing an alert or an alarm at a time determined to be effective for user, or a pre-event or situational decision 235*e*, e.g., a decision to be made before sleep, a meal, exercise, driving, activity, or the like. Other exemplary outputs include a permanent or temporary change to a basal rate setting, a recommendation for rescue carbs, or the like. Specific outputs, and the way the same may change according to the decision-support application/functionality, are discussed in the Outputs section below.

While various core methods have been described above with regard to providing decision-support application/functionality in a way that is supportive of user-defined functionality, it will be understood that the core methods need not be mutually exclusive. For example, various combinations of the core methods may be employed in a given implementation. In addition, multiple methods may be performed in parallel to determine optimal treatment decisions, and then the safest option chosen. That is, various algorithms may be employed as described above to use defined states, sensor data, user inputs, and other available information to calculate an optimal diabetes treatment decision. Multiple methods may be performed in parallel to calculate the optimal treatment decision, and then the most conservative or safest of the solutions may be provided to the user. For example, in times of sensor noise, either a filtered value or the raw sensor value may be used to calculate a current glucose estimate and subsequently a recommended insulin bolus. Doses could be calculated based on both sensor values in parallel and then the more conservative dose could be recommended. Another example is to use a glucose rate of change estimate based on either a trend calculated in the CGM algorithm or as a two-point difference of the most recent pair of glucose values, and the rate of change that provides the more conservative dose would be used.

A number of exemplary inputs and notations about such inputs are given in the table. It will be understood that other inputs may also be employed, and that the notations given about the inputs are not necessarily limiting. For example, inputs may be noted as having a certain context, but in some cases the context may be thought of as overlapping certain categories. As another example of variations, certain inputs may be identified as user entered, but in some cases the same may be determined by a sensor or the like. For example, meal data may be determined by user input, but also by GPS, from pattern data or from an app such as a camera. As noted the decision-support application/functionality incorporates machine learning to increase the accuracy and appropriateness of therapy prompts over time. Meal data entered by the user, e.g., "small meal", "medium meal", and so on, may be "learned" by the system so that the decision-support application/functionality may better understand over time what the user considers a "small meal", and so on. Temporal patterns may be analyzed by the systems and methods to determine aspects of, e.g., meals and exercise; but users may also identify and quantify events they want to track, including those corresponding to meals and exercise.

In one alternative implementation, the algorithm may have just one "average" meal defined but allow for a degree of automatic adjustment to define what is large or small for a user. In this implementation, the "average" meal may be defined for a population or for an individual user. This implementation may be more convenient to implement as only one meal size need be defined, and the same does not need to be changed for every meal. Rather, a multiplier may be applied, by the patient, by the HCP, or automatically, to assess if the meal is "average", "light", or "heavy/large". The algorithm may then automatically increase or decrease suggested insulin amounts according to the assessment. For example, an exemplary "multiplier" may be that a large meal is 1.5× the effect of the "average" meal, or that a small meal is 0.5 times the effect of the "average" meal. Such implementations may be particularly convenient for a user to implement, particularly where the user is not accustomed to carb counting. Extensions of such an idea to exercise and other applications will be understood.

Where multiple types of data are employed as inputs in a given algorithm, the multiple types may be related, e.g., may be a type, timing, and intensity of a variable, e.g., illness, exercise, meals, sleep, and so on, e.g., a duration and intensity of exercise.

Figure 17:
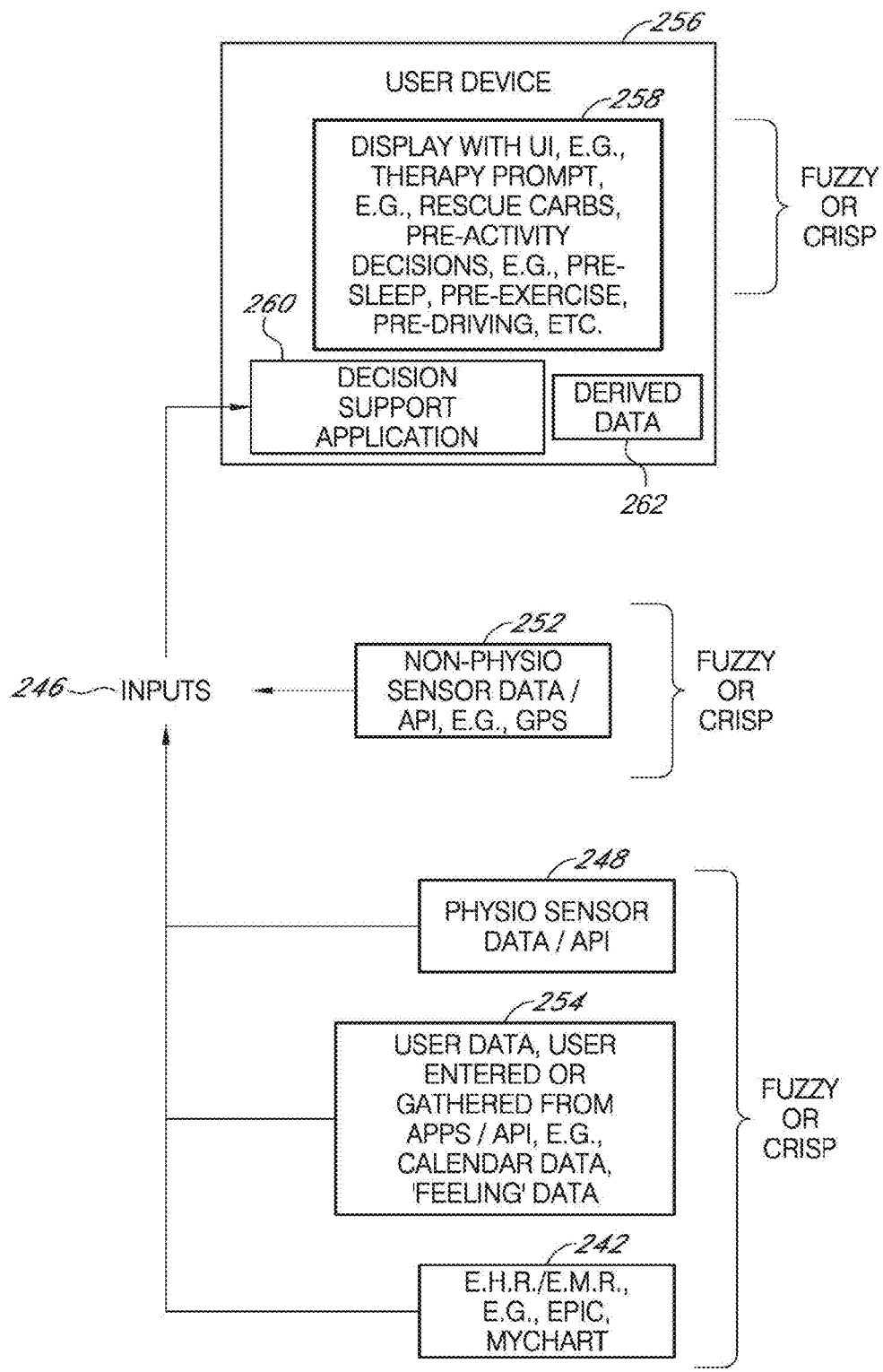
FIG. 17 illustrates various physical sources of input data.

In the table the inputs are divided into two categories: real-time data and non-real-time data. Referring also to FIG. 17, these categories of inputs 246 are then divided into subcategories as: data from sensors (248 and 252), user data 254 which may be user-entered data or data from other apps, e.g., from a suitable API, derived data, and other data. Some subcategories appear in both real-time data and non-real-time data. In any case, the inputs 246 then feed into a user device 256 which may be a dedicated receiver or smart phone, and more particularly into a decision-support application 260 disposed therein. Derived data 262 may be stored in the user device 256, and a display 258 may be provided with a user interface to display prompts to the user as well as for receiving user-entered data. The derived data 262 may be derived by a processor within the user device 256, and the derivation of the data may occur within the decision-support application/functionality or may occur outside of the same.

FIG. 16—Inputs

Referring back to the types of data illustrated in FIG. 16, the sub subcategories then describe specific types of data or are themselves categories. For example, a sub subcategory in real-time data is "physiological sensors" and these may be further broken into different types, e.g., CGM, SMBG sensors, body temperature sensors, skin conductivity sensors, hormone sensors, heart rate sensors, and the like. Besides physiological sensors, other sensor data include non-physiological sensors, such as those dealing with atmospheric pressure, accelerometers, GPS, sensors measuring aspects of the CGM system itself, temperature sensors, and the like. Such inputs may be provided from wearable devices/sensors, e.g., those available from an Apple Watch®, Fitbit®, or other wearable. Other devices providing inputs may include other mobile devices, including smart phones.

Sensors such as accelerometers and GPS may be conveniently used to provide data about exercise or activity performed by the user. In some cases, GPS or other sensors may be employed to determine other types of activity data, e.g., if a user is driving, which may in turn inform how an output to a user may be displayed, e.g., on a smart watch versus on a smart phone.

In the particular case of an accelerometer, the same may be advantageously employed to detect sleep patterns or sleep quality as related to glucose control. Such may generally provide data related to position but also importantly to activity detection as well as duration and intensity. One potential type of accelerometer that may be advantageously employed is a three-axis accelerometer.

In some cases, the decision-support application/functionality may allow data to be entered about the start (or other marker) of a menstrual cycle. In this way, users may be able to track over several months the behavior of blood sugar at different times of the month with regard to the cycle. Of course, such an algorithm and data may also be used to assist pregnancy efforts or using the rhythm method for birth control.

Hormone sensors may provide another source of entered data, and in one example may also be a source of data related to the menstrual cycle. Other hormone sensors may include those that sense cortisone and/or epinephrine. Hormone sensors or the like may also be employed to provide a measure of "energy in" versus "energy out", particularly with regard to a parameterized system model of the patient.

Another subcategory of inputs in real-time data includes user-entered data, including goals, a problem to be solved, a desire for therapy, entered data about stress, emotion, or feelings, pain level data, sleep level data, data from a follower device, pump data, meal data, exercise data, blood glucose data from an external blood glucose meter, and so on. User-entered data may include user estimates of glucose values, so that decision-support may be rendered in a way that helps the user to better correlate a perceived glucose value with a real one. For example, the decision-support application/functionality may be enabled to better assist the user in determining and discerning what different levels of hyperglycemia feel like. User-entered data may also include user demographic data such as age, gender, and so on. Such data may be conveniently obtained by, e.g., a swiping of the user's driver's license.

Where user-entered data include exercise, systems and methods according to present principles may allow users to save specific workouts or events to allow patterns in post workout glycemic fluctuations to be analyzed and potentially found, resulting in appropriate automatic or manual therapy modifications to be made by the decision-support application/functionality. For example, users may save workouts such as "Cardio 1", "Cardio 2", "Get Swoll 1", "Get Swoll 2", and so on. Other gradations of exercise may include those pertaining to intensity, e.g., light, medium, hard, duration, e.g., 5 min., 10 min., 15 min., 20 min., 25 min., 30 min., one hour, and so on.

Goal data may include an indication of priorities in terms of glucose control, e.g., hypoglycemic versus hyperglycemic avoidance. Different control types may be provided as preprogrammed profiles that a user may choose in selecting a goal. For example, a user may choose a goal of hypo-minimizing control, hyper minimizing control, frequent versus infrequent correction boluses, and so on, so as to fit different treatment styles and goals.

In the same way, user feedback may also constitute an important input into decision-support. That is, the decision-support application/functionality may be modified based on user feedback, e.g., periodically querying the user as to what the user would like to be different about the recent glycemic control of the user and providing options such as "I would like to reduce my number of nighttime hypos" or "I would prefer to not have to give correction boluses as often". Feedback may be prompted for in a convenient fashion to minimize annoyance for the user. For example, feedback may be provided by slider bars or other user interface elements convenient for user selection. Slider bars may also be provided for other user inputs, e.g., to indicate how much interaction is desired.

As noted above the decision-support application/functionality may be advantageously employed as part of a bolus calculator. Thus, user input may also include user input into such a bolus calculator. For example, the decision-support application/functionality may be rendered with a user interface that affords the user predetermined dose adjustments, e.g., +/−0%, +/−10%, +/−20%, and so on. The dose adjustments presented may themselves depend on the CGM trend, e.g., negative dose adjustments may be provided in the case of a negative or falling glucose trend. The chosen adjustment would apply to the bolus dose calculated with or without any other trend adjustment. Alternatively, adjustments can be fuzzy. In yet another implementation, users can choose to customize the adjustment, within bounds. Over time, with data, the decision-support application/functionality may determine optimal adjustments based on the user-entered data (and other inputs), and with provider authorization (or alternatively without provider authorization/confirmation), the adjustment options may be presented to the user and re-determined.

In a related implementation, rather than a percentage, rate of change data may be employed to increase/decrease the bolus value calculated by a fixed amount. In this way, the patient adds or subtracts enough insulin to cover that amount of glucose change from the meal bolus using the patient's own insulin sensitivity/correction factor. In this implementation, initially the bolus calculation could be left unmodified, and the decision-support application/functionality may learn how much insulin needs to be added or subtracted based on rate of change as part of a case-based learning process. For example, in cases where glucose is rising or falling, rather than updating insulin sensitivity, the system may learn how far the glucose is from target and consider that to be the amount of glucose that should be accounted for. In this case a new insulin sensitivity is not learned, but rather the best insulin sensitivity estimate is used based on the other descriptors of the case, e.g., lifestyle factors, e.g., specific to an insulin sensitivity for breakfast with no exercise. As it may be desired to learn both how much to adjust insulin boluses based on rate of change and how insulin sensitivity changes for time of day, exercise, etc., systems and methods according to present principles may advantageously separate the two problems and only update insulin sensitivity when rates of change are relatively stable. Once it is learned how much the user should adjust the insulin of the user based on rate of change, then such data may be pushed to the HCP, e.g., showing patterns of, e.g., how the user post-meal glucose is always around 30 mg/dL too high when they take the user takes a meal bolus and the trend arrow is 90 degrees up, and the HCP may be requested to approve the amount of insulin to add or subtract. Machine learning may also be used to determine if it is better to modify insulin boluses based on rate of change using a percent or a fixed amount, just in case such may vary patient-to-patient. Additional details of the use of rates of change data are provided below in an example.

Returning to the discussion of various inputs, inputs may include data about followers of the user, or data about other related users. The entered data may include data about social groupings, e.g., for the achievement of individual or group goals, and may further employ natural language processing to deduce objective and quantifiable desires and goals of the group or its members. Inputs may further include inputs from followers, e.g., in response to a query such as "What do you think is going on with your daughter?".

Another source of real-time data that is user entered includes meal data. Users may enter meal data in a fuzzy or categorized fashion or also as a crisp input. Machine learning may be employed to learn in an objective sense how a user categorizes the meal. For example, if a user terms a meal "small", in terms of what is entered into the decision-support application/functionality, the system may learn in a more quantitative or objective way what the user considers a "small" meal. The same is true for meals entered and termed as other sizes. The same is also true for user-entered data regarding meal composition. In other words, the system can learn what a user means when the user enters a statement of meal composition into the decision-support application/functionality. For example, if the user terms a meal "high carb", the system can learn from the glucose response and data about delivered insulin (if available), in combination with the meal data, what the user considers "high carb".

Another subcategory of inputs in real-time data includes data from other applications or "apps", e.g., generally from a suitable API. Such apps may reside on the computing environment providing the decision-support application/functionality or may be in wired or wireless communication therewith. Such apps include: calendar apps, GPS apps, CGM apps, apps holding historical data or other information, SMBG apps, temperature monitor apps, Healthkit®, data from followers, e.g., from text messaging apps, bolus calculator apps, clock apps to provide time of day, apps indicating the elapsed time, so as to allow user prompts to be provided at optimum times, apps providing access to cloud data or "big" data, camera apps, pump applications, pen applications, bolus calculator applications, and the like. As a particular example, a texting or e-mail app may refer to an event, e.g., a dinner party. Through an appropriate API, the texting or e-mail app may then serve as a source for input of calendar data. In a specific example, there could be an option for "add event to CGM" or the CGM (or equivalently decision-support application/functionality) could automatically pull event data whenever a calendar event is added. Such facility would allow users to create calendar events and CGM events at the same time, providing an easier way to collect event data and see how events affect glucose trends.

Figure 18A:
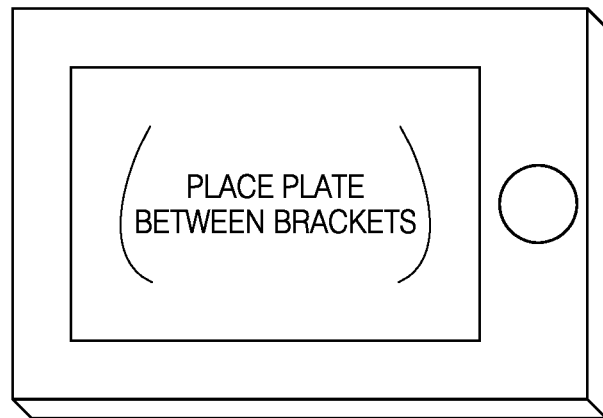
FIGS. 18A and 18B illustrate nontraditional ways of obtaining meal data.
Figure 18B:
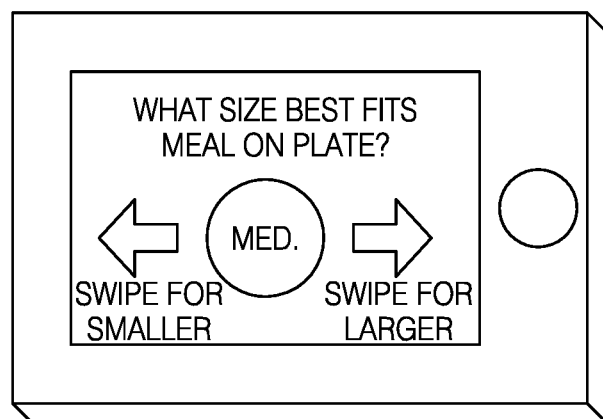

For example, bolus calculator decision-support generally requires entry of meal data. In one implementation, a camera application may prompt the user to take a picture of a meal on a plate (see FIG. 18A). The user may use the phone camera to take the picture, and brackets may be provided as part of a user interface on the screen to guide the user on how to take the picture. The app may then measure the meal size in relation to the plate size and denote the meal as, e.g., small, medium, or large. The app may then give a dose recommendation based on the meal size. In a more enhanced implementation, the app may use photographic recognition techniques to determine, estimate, or guess what is on the plate, and provide an estimate as to the consequent meal composition. Variations will be understood. For example, in an alternative implementation, the user prompt may instruct the user to swipe through different circle (or other shape) sizes over a picture of the meal on the plate (see FIG. 18B). They app may then ask the user to find the circle size that best matches the meal size on the plate.

Other real-time data that may be provided from an app includes pump or related data, including recent boluses, basal rate, and the like. As another example, the prompt may be provided based on estimated insulin-on-board in conjunction with CGM inputs and other contextual information. Insulin-on-board is a term used to describe the amount of insulin that has been given to the patient but that has not been used by the body to transport glucose into the tissue. If after taking a meal bolus, the estimated insulin-on-board is still one half of the original dose, but measured glucose has already dropped to 80, an alert might be provided because continued insulin activity is expected, further lowering the glucose to hypoglycemic levels.

In more detail, patients who administer too much insulin are at risk of hypoglycemia and possible death. There are currently no real-time measurement methods to measure how much insulin is within the patient. Insulin stacking occurs when an insulin using patient administers multiple boluses of insulin within a short timeframe. Insulin from the previous dose may not have taken its full effect and therefore the patient may give the patient too much insulin on subsequent doses, posing a significant danger of hypoglycemia to the patient. A continuous direct insulin sensor may be employed to measure the amount of insulin that is within a patient. This detector can be used as an alert or as a failsafe to shut off a pump or an artificial pancreas. As each patient generally has a different insulin sensitivity (but this sensitivity may be learned using the decision-support application/functionality described here), multiple thresholds are generally needed for alert settings.

A secondary aspect to this implementation includes the use of a direct insulin sensor to monitor how much insulin is in the patient. The amount of insulin can be used to give the patient feedback to recommend a safe dose of insulin. The insulin information can also be transmitted directly to a calculator or pump and used in an insulin dosing calculation to better estimate the proper amount of insulin to dose. This could be used instead of the current insulin-on-board estimation used in bolus calculators.

A third aspect of this implementation describes the use of a direct insulin sensor to measure a patient's insulin sensitivity. Insulin sensitivity can vary between patients and even over time with the same patient. Accordingly, systems and methods according to present principles may use a direct insulin detector to measure the amount of insulin in a patient's body. By combining the information of glucose and insulin concentration within a patient into an algorithm, the insulin sensitivity can be calculated. The information contained in the insulin sensitivity can then be used to determine if an insulin sensitizer, insulin secretagogue, or insulin, should be used to manage the diabetes, e.g., to increase or decrease the amount of insulin that the patient is given to best control their glucose levels.

Returning to the chart of inputs of FIG. 16, and as another example of real-time data, which may also be used in non-real-time, GPS data from an app or other such sensor may be employed for a user away from home, e.g., for a user at college, to determine potential followers or friends.

Calendar apps may be employed to provide data about users. As an example of determining data from multiple different sources, exercise data may be determined from calendar data, if the exercise is located within an appointment notation or if a pattern of exercise implies that a user exercises at the same time every day or week.

As another example of inputs, safety rules may be employed to provide decision-support to various levels of aggressiveness. For example, if a user does not provide detailed meal information, then a decision-support application/functionality which is providing a user prompt to drive the user's glucose level to a target range may aim for the high end of the target range rather than the middle of the target. In the same way, if the user provides meal data indicating a very large amount of carbohydrates, then the high-end of the target range may again be aimed for in the decision-support application/functionality, as errors in carb counting are known to have worse effects as the overall carb amount increases.

As another example of inputs, device diagnostics may serve as an input, including device signal quality and confidence, as well as to determine risk stratifications based on the same. For example, meal or correction boluses or other decision-support prompts may be informed at least in part by confidence intervals, and the confidence intervals may be informed at least in part by device signal quality and/or detected faults.

Cloud or big data may also be used. As an example of the use of cloud or big data, a HCP may desire to determine initial values for insulin resistance or insulin sensitivity. The HCP may enter demographic data such as weight, age, and gender. The app may then search through a database and find users most similar to the subject user, and may take an average of their settings for initial suggestions. Cloud or big data may further be employed for initial risk stratification, again based on aggregate numbers.

As noted above, a CGM app may provide an input to the decision-support application/functionality. For example, in some implementations it may be preferable to handle glucose levels outside of a range of, e.g., 40-400, using fuzzy logic. Yet other data which may serve as an input and which is available from a CGM app may include a target glucose level or range.

Yet another type of input involves derived data. Derived data, which also may also in some cases constitute real-time data, includes an analyte rate of change or acceleration, various types of sensitivities, including sensitivities to insulin, sleep, meal, and/or exercise, a hierarchy within a risk stratification (described in greater detail below), glucose variability, user stress/emotions/feeling data, a user desire for interaction with the device, sensor accuracy/confidence/signal quality, pattern data, and the like. Such sensitivities often constitute lifestyle factors as defined above. The above-noted detection of hormone levels may further aid in the detection and quantification of insulin sensitivity, as hormone levels are known to be an associated factor.

Insulin sensitivity can be based on sleep, energy intake versus energy output, food intake, and the like. Insulin sensitivity can change rapidly and with, e.g., circadian rhythms. Insulin sensitivity is known to be event driven, stress driven, and also driven by factors such as illness, activity, or the like. If a user employs a CGM monitor, events affecting insulin sensitivity can be detected, and a measure of insulin sensitivity may even be determined from knowledge of intake values of carbohydrates into glucose and basal/bolus amounts of insulin. Typical and atypical ranges of insulin sensitivity can also be determined. Insulin sensitivity can be measured by, e.g., measuring a basal rate at the same time each day, and seeing how glucose values change with respect to various events including meals, exercise, stress, or the like, and further by performing the same test with various changes in basal rate. Insulin sensitivity may also be detected by testing levels of various hormones, including cortisol and/or epinephrine.

Derived data corresponding to meal sensitivities may be made even more granular by determination of, e.g., sugar sensitivity, dinner sensitivity, and so on. Other such perturbation or interaction sensitivities will also be understood to be derivable.

"Insulin-to-carb" ratios may also constitute derived data, and the same are generally determined and optimized using retrospective analysis. The same may be used to provide decision-support education for a user by demonstrating graphically the impact of different insulin-to-carb levels. In particular, with knowledge of insulin delivery, the decision-support application/functionality, or a related or connected module, may display to the user the effect of using different insulin-to-carb ratios on the glucose levels of the user, e.g., by modifying a retrospective glucose trend line. Within the decision-support application/functionality, optimal insulin-to-carb ratio settings could be automatically determined, and it may be further determined how insulin-to-carb settings vary with time of day, activity level, or the like.

In some cases, derived data require a time duration over which to analyze or an analysis of a pattern to determine. For example, a determination of insulin sensitivity or an insulin resistance may require analysis of data taken over a time duration. In a specific implementation, insulin resistance can change throughout the menstrual cycle of a female diabetic patient. The decision-support application/functionality can use a resulting cycle of insulin resistance, e.g., including incorporating insulin consumption as well as glucose values, to determine a predictive insulin resistance alert to provide to the user. For example, the patient could receive a reminder at the beginning of the day that historically in the cycle of the user's blood sugar tends to go higher or lower. Such a prompt made help the patient be more conscientious of how the user could expect the user's blood sugar to behave.

For an initial or seed value of insulin sensitivity, population data may be employed from a database of patients, particularly those of similar weight, age, gender, length of diabetes, and so on. Such may be used for default values and then auto adjusted as additional information about the user becomes known over time.

Meal data may also be a form of derived data as the same may be derived from food patterns, food libraries, and so on. In another way of deriving meal data, retrospective analytics may be employed to use other data to estimate carb content for a given meal. Such other data may include, e.g., insulin delivered, glucose levels, exercise, health, meal time, and the like. By collecting such data, the decision-support application/functionality may be enabled to determine a user's typical meal and typical glucose response to that meal while mitigating the effect of other factors on the glucose of the user. Such functionality has several benefits, including improving accuracy of bolus calculators, the ability to optimize alerts if the system notices an atypical glucose response, assistance to users in understanding the eating patterns of the user and the effects of different meals on the glucose of the user, and more accurate calculation of insulin to carb ratios.

Derived data may further include user estimation data, e.g., whether and by how much a user is apt to make an error in carb counting, e.g., to overestimate or underestimate.

Derived data may also include data determined about recognized patterns, where the patterns are recognized by analysis of historical data over time. Exemplary recognized patterns include patterns of nightly hypoglycemia, postprandial highs, post exercise lows, or the like.

One way of determining such patterns, or of detecting occurrences of glucose events not in patterns, is by "binning" certain events defined by particular characteristics. That is, portions of glucose traces may be detected that meet predefined criteria indicative of certain diabetic challenges, e.g., rebound hypoglycemia, and then patterns may be looked for in these events that have been "binned" accordingly.

FIG. 19 Et Seq.

Figure 19:
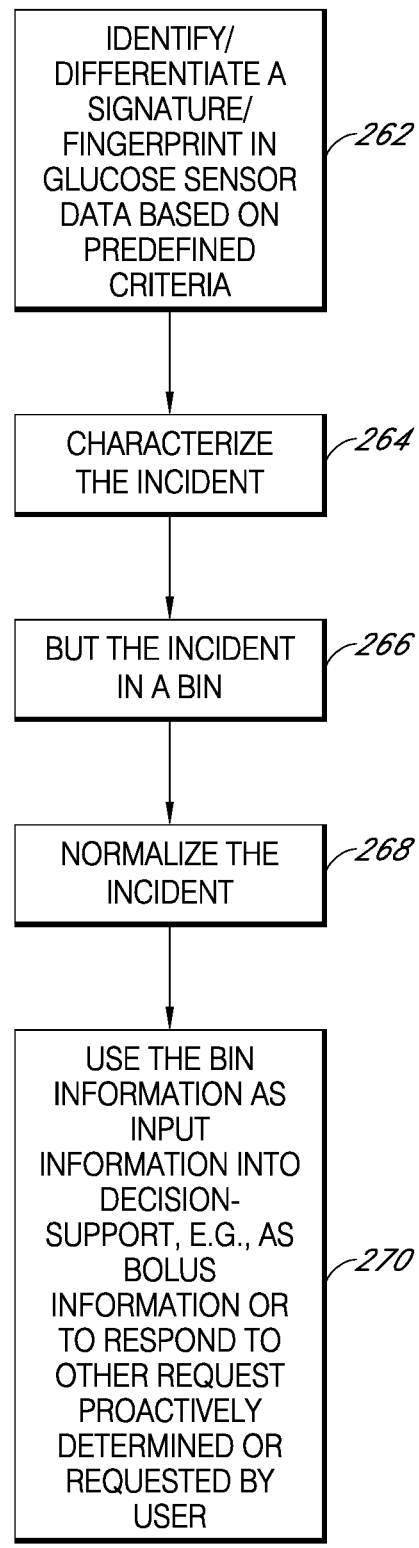
FIG. 19 is a flowchart for obtaining signal signature information which may then be employed as an input for decision-support, e.g., for state definitions and determination.

In more detail, and referring to the flowchart of FIG. 19, a signature or fingerprint in glucose sensor data may be identified or differentiated within an individual patient based on some predefined criteria (step 262). Such criteria may include time-based criteria and/or may include detected specific incidents within specific constraints. In the present system, according to present principles, bins may be differentiated by different criteria. A supervised learning algorithm may be employed that allows for more bins to be learned for individual specific patterns. For example, bins can be based on insulin data, rate of change of glucose data (or acceleration/deceleration thereof), patterns of data identified before and used to characterize data, e.g., events occurring before small meals, responsiveness of an individual to their glucose information, and so on.

A next step is that the incident may be characterized, e.g., based on a decay curve, waveform signature, or the like (step 264). Exemplary incidents may include meal bolus indicators, e.g., based on insulin data, which may be classified into small, medium, and large meal bins. Such may correlate with insulin data. Different meal types may also be characterized, which may then be sub-binned into different meal compositions. These may correlate with rate of change/acceleration/deceleration. Incidents can also be characterized based on their correlation with events before a meal, and such corresponds to the patterns of data noted above. Incidents may further be based on behavioral patterns, e.g., how often a user reviews the glucose data of the user or responds to alarms, and such can be correlated with the responsiveness data noted above. It will be understood that other bins may also be employed.

The characterized incidents may then be placed into a bin (step 266). By then synchronizing by incident, bins may be tuned for specific patient physiology. The bins can then be normalized, i.e., a normal distribution of incidents in the bin may be defined (step 268).

The normalized bin information may then be used proactively as an input into the decision-support application/functionality (step 270), e.g., in the determination or definition of the state according to Step A. As one example, the normalized bin information may be an input to a bolus calculator. The normalized bin information may also be employed to respond to other requests proactively determined or requested by the user, e.g., when a user asks for a bolus calculation before a meal, or when the system prompts for a bolus calculation before a meal based on time or other factors. The binning technique may be employed to determine when a patient is more tuned into their data, based on behavioral input, which may then allow for more aggressive recommendations as opposed to the case when the user is not focused on glucose information, e.g., nighttime, when the bolus recommendation is generally more conservative.

Returning to FIG. 16, in non-real-time data, inputs may include user-entered data such as prior SMBG data, user savviness with technology, goal data, a problem to be solved, a certain desire for the therapy, a target glucose level, demographic data such as age and gender, the cardio health of the user, cholesterol level, a type of mathematical calculation to be employed (typically entered by default or by a HCP), data about illness or pregnancy or menstruation, data about medications taken, smoking history, and the like. Non-real-time data may also include derived data, including historical patterns, gastric emptying duration, or the like. Other non-real-time data may include data about a follower, e.g., the tone of communications of the follower, the language of the follower, and so on. These may be employed in modifying outputs for greater effectiveness to the user.

With regard to gastric emptying duration, it is noted that 25% of the diabetic population (type 1 and type 2) experience some form of gastric emptying delay. 7 to 12% of the same group suffers from an elevated delay for gastric emptying. The population of gastric emptying delay is increasing at a very significant rate within the diabetic population, and is becoming a concern for health care professionals within the general population currently.

Current bolus wizards do not factor in gastric emptying; thus, certain risks exist. For example, if gastric emptying is not factored into a closed loop pancreas system, the individual runs the risk of glucose variability where there are repeated corrections and insulin delivery reductions. This results in chaotic insulin delivery which would resemble a successive approximation wave form over time. If the same is not used within a bolus calculator for an insulin pump, the result is to endanger the person as the person may suffer a hypoglycemic event which would roughly correlate to the size of the meal which they had dosed for. The person may also suffer a hyperglycemic event which would roughly correlate again to the meal size, as its effects would take effect when the reactance of the insulin is reduced and is declining within the system.

Over time such variabilities can manifest themselves into further damage which may degrade gastric function over time. Additionally, the person runs the risk of increased peripheral neuropathy.

Gastric emptying delays push out the process of moving processed and prepared nutrients and food into the small intestines where actual absorption of nutrients occurs and can be triggered by such factors as neuropathy of the vagus nerve, nerve damage within the stomach, and muscle damage within the stomach. Gastric emptying studies are used by GI doctors to quantify the extent of the delay which may result in a prognosis of gastro paresis.

The general direction given to insulin dependent diabetic patients is to dose (bolus) between 0 and 30 minutes prior to a meal. The rationale in this directive is to time the effect of the insulin to correspond to the time at which the consumed food enters the absorption phase. This timing is accurate in the case where gastric emptying is not an issue (75% of the type 1 & type 2 population). However, in the balance of the population, the delivery time of the insulin is inaccurate. Fast acting insulin reaches maximum effectiveness roughly 90 to 120 minutes after a bolus is delivered. This is the delay from bolus delivery, propagation through the body and adherence to the A & B receptors on the surface of the cells. At that time, the cells are able to process sugars and do so. However, for an individual with a gastric emptying delay, the delivery of the processed foods to the system has not occurred yet. For these individuals, roughly 90 to 120 minutes after eating (if they dosed a bolus 30 minutes prior to a meal) they will suffer a hypoglycemic event. This event is generally addressed with a liquid such as orange juice which enters the intestines and system more quickly than solid food.

The insulin reaction is on the decline at the end of the peak for an elevated case of gastric emptying delay at the time where the food is being processed and is entering the system. This results in a hyperglycemic event at which a correction bolus needs to be delivered. Thus, gastric emptying duration may be employed as an input in order to provide a time delay for delivery of a bolus after a meal. This delay may be applied to a bolus calculator or to a closed loop artificial pancreas system. Gastric emptying duration may also be employed as an input in order to provide a time delay for a modified basal rate after a meal. This delay may be applied to an insulin pump or to a closed loop artificial pancreas system.

One way of determining gastric emptying delay within an individual is as follows. If a CGM user enters a bolus and a meal, then the following 4 hours of data are analyzed within the CGM. If there is a repeatable event which occurs for the individual which follows a trend, then a gastric emptying delay may be inferred. The inferred delay may then be applied to the bolus and/or modified basal rates as described above.

Figure 20:
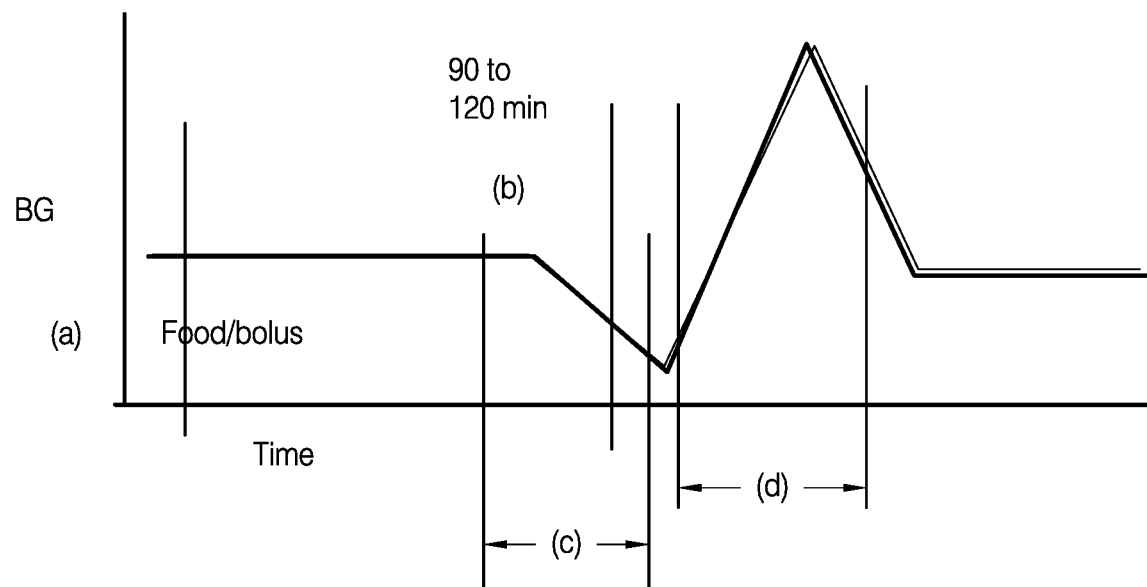
FIG. 20 is a chart illustrating gastric emptying duration, which can serve as an input into decision-support, e.g., for state definition and determination.

Referring to the example shown in FIG. 20, time period (a) indicates bolus and food entries. They are also offset from one another. Time period (b) indicates the period when food processing should occur, however, for this exemplary patient, the food processing is delayed. Time period (c) indicates when food should be processed normally as it would align with the bolus. Time period (d) indicates when actual food processing occurs in a gastric delay. The slope of the BG decline is indicative of the rate of gastric emptying delay as well as the general delay. This delay is also represented within the BG value signal by determining the deltas between the start of (c) & (d) as well as their durations. In order to isolate this signal within the general noise within the blood glucose signal, insulin sensitivity is calculated from the individual's blood glucose data.

Referring again back to FIG. 16, non real-time data may further include stored data, as stored and retrieved from memory or other storage. Stored data may include historical data, both of determined patterns and data used for determining patterns or other glucose events. Stored data may include prior user events. For example, if a HCP has previously commented on a pattern, if the pattern repeats, the HCP comment may be re-displayed on the user interface.

Inputs can be "fuzzy", e.g., may fall into certain categories, and the categories themselves used as inputs, e.g., small/medium/large meals, or "less than normal"/normal/ "more than normal", or alternatively the inputs may be crisp. Thus, also shown in the table are exemplary categorized or fuzzy inputs, as well as exemplary crisp inputs. The table also indicates an interpretation as to the type of context for the input, e.g., whether the same concerns lifestyle aspects, situational aspects, clinical aspects, or device aspects. In some cases, an input may occupy more than one category.

The way in which inputs are used and aggregated may vary. In one implementation, a function may be determined, or a user system model may be created, and the inputs used directly on the function or model. In another example, in a hierarchical approach, the decision-support application/functionality may be designed to use information obtained from different sources in a layered approach. Bare-bones systems will use CGM data, and as additional data are received, the same may be used for decision support. The confidence in estimates and decisions then generally improves as the amount of information increases. In the same way, users or use conditions may be categorized in buckets or layers of risk. Each time information is available, the system may move up or down the hierarchy in order to ensure safety.

In addition, as may be understood from the above, combinations of inputs may themselves result in an additional input. For example, an alternative empirical approach may be to control aggressiveness based on historical levels or success of predictions. For example, aggressiveness in decision-support may be reduced when the situation, e.g., time of day, day of week, type of event, and so on, has historically resulted in variable or poorly-predicted glucose levels. For example, a user may consume a very consistent lunch during the week and inconsistent lunches on weekends, where the consistency refers to timing, meal size, and meal content. The inconsistency may result in less predictable results of pre-lunch boluses on weekends. The decision-support application functionality may then detect this poor predictability and adjust aggressiveness accordingly.

Figure 21:
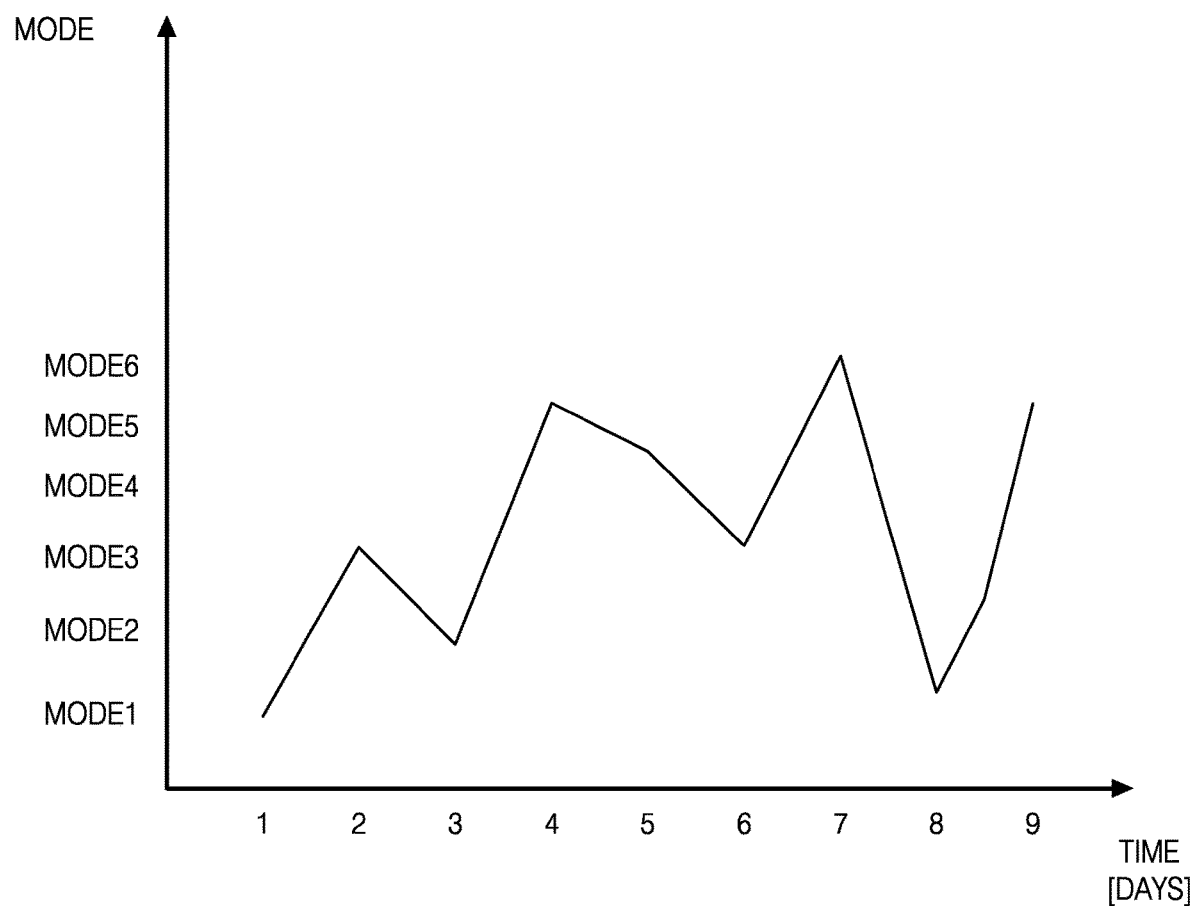
FIG. 21 is a chart illustrating modes, e.g., modes of operation of CGMs, and modes may be used as inputs into decision-support, e.g., for state definition and determination.

Referring to FIG. 21, modes of operation of the CGM app or decision-support application/functionality may serve as inputs which in turn may be categorized in different ways. For example, the mode of operation may refer to a calibration mode, such as device self-calibration or factory calibration. The mode of operation may also refer to a transmission mode (transmission of data to a display device), such as scheduled transmissions or unscheduled transmissions. It will be noted that all of these modes described are exemplary and that other modes of operation are also possible. The mode of operation may also refer to a decision-support mode, such as therapeutic, non-therapeutic, adjunctive, non-adjunctive, and so on. As may be seen in the figure, even where the modes may be thought of as being operationally sequential, the decision-support application/functionality may jump from one mode to an adjacent mode or from one mode to a nonadjacent mode. An example is the case of scheduled transmissions, where in mode 1 a transmission is made every 30 seconds, in mode 2 a transmission every minute, in mode 3 a transmission every 5 minutes, and so on for mode 4, mode 5, and mode 6. In many cases such modes will not be marked by just a change in a characteristic time, but rather by a change in functionality, e.g., from periodic to aperiodic.

Signals may be collected from sensors within smart watches such as the Apple Watch® smart watch and the Microsoft® Band smart watch to augment certain entered data, e.g., for hypoglycemia detection. The signals can include heart rate, sympathetic/parasympathetic balance (inferred from heart rate), perspiration, motion, and the like. The signals can be used in addition to the CGM signal. Algorithms employed to process the auxiliary signals can be trained on the patient's own data, using CGM to assist in the training. These outer limits can be optimized off-line, or in the cloud. Detection criteria then can be sent to the patient's smart phone and/or smart watch. For example, there may be instances when CGM fails to detect hypoglycemia, but when augmented with auxiliary signals indicating possible hypoglycemia, the patient may be alerted to suspected hypoglycemia and thereby enabled to avoid the consequences. Alternatively, after the algorithms used to process the auxiliary signals have been trained, the smart watch signals can be used to detect hypoglycemia without the use of CGM. In this use case, adjustments to the algorithms may be used to optimize sensitivity/specificity.

Detected cognitive ability may also serve as an input. In more detail, it is noted that cognitive ability and motor function may be affected by numerous varied inputs and effects. For example, an individual with diabetes may suffer from reduced cognition and/or motor functions as a function of hypoglycemia. As a hypoglycemic incident occurs, and blood sugar levels drop, the individual suffers from concentration and/or comprehension degradation. Additionally, due to the body responding to a lack of sugar, the muscles may tense and begin to act erratically.

With a capacitive ability on an input device, such as a smart phone or tablet, the user may view information, make decisions, and press on screen indicators to perform device interaction. As a user becomes familiar with an application on such a device, the ability of the user to make decisions increases, while the delay between interactions reduces. The users additionally develop a series of familiar sequences in order to perform common tasks that the user has become accustomed to.

However, when an individual suffers from a drug interaction, alcohol, or hypo/hyper glycaemia, these familiar tasks become less familiar. This results in a situation where the user must spend more time observing and comprehending a user interface which normally is intuitive and requires no concentration. The time spent on a user interface screen will lengthen compared to the historical norm of the individual. When the motor functions of a user degrade due to any of the mentioned influences, the ability to press an on screen indicator such as a button, a slider, or onscreen keyboard, become less uniform, and may deviate from the normal metrics for the user. In such situations, the initial press location in relation to the center point of the control may deviate from the user's normal press location. Additionally, where a press/lift action is the interaction to a button, in a motor control deficient situation, the press may be followed by a "drag" motion, and the lift location of the interaction may change. By accumulating the metrics of time and user interaction on a user interface screen, e.g., the press XY location for a control in relation to its center point, the XY distance travel prior to lifting the finger, the duration of pressed state, and the like, a profile of the user's interaction can be maintained. The data can then be correlated to the user blood sugar reading in order to determine a general population behavior, as well as sub populations based on gender, age, and so on. This information can further be used to determine where the cognitive ability/motor function ability of an individual rests, in relation to population groups which the individual is a part of. A degree of impairment for a particular individual may also be determined and used as an input. In other words, the decision-support application/functionality may make decisions and/or actions based on this information, e.g., by using the same in the definition of a state according to Step A. Such decisions and actions may be to alert another individual in order to notify or request assistance. It may also be used to disallow operation of a motor vehicle or other potentially unsafe action in such a condition.

In a related implementation, a guiding "wizard" component may instantiate if the cognitive ability is degraded. In this case, more verification may occur such as "You are about to change your settings, are you sure you want to do this?", safety guidance such as "you should wait until your blood sugar rises before changing your sensor" may occur, and so on.

In another implementation, once motor function degradation is detected, buttons and user interface components can be enlarged, or a larger press area may be utilized. It also may interpret a "drag" motion on a button as a "press" action, thus assisting the individual.

In this way, patients affected by hypo/hyper glycaemia may be assisted, and their followers notified of their condition. It may further keep those impaired by alcohol from trying to take unsafe or untimely actions. It may further identify anecdotally if a drug interaction or drug reaction is occurring. It may further track such data over time in order to accrue reaction over time to such events. It may generate data useful in determining a person's condition in relation to a population of similar people.

Another type of data which may be employed in providing decision-support is diabetic subtype. In particular, diabetes is currently categorized into two different categories. Type I diabetic patients are unable to produce insulin and thus rely on an external source of the same. Type II diabetic patients have a nonoptimal insulin production capability and generally rely on injected insulin in order to offset the physiological insulin production anomaly. Various subtypes of these may also be understood, generally corresponding to genetic mutation. Genetic mutation #1 involves a marker within the genetic sequence of individuals which results in a surfaced apology aberration on the sales of the subject. This aberration causes a reduced ability for insulin to adhere to the A and B receptors on the cell surface. The effect of the inhibition or reduced adherence results in a difficulty for insulin to perform its effect. This causes insulin to take a longer period of time to adhere to cellular surfaces, thereby reducing the effect of a known volume of insulin. Additionally, a longer period of time is required in order for the insulin to adhere to an adequate population of cells in order to cause a measurable effect on blood glucose levels. This is referred to as insulin resistance. Genetic mutation #2 is the opposite of genetic mutation #1, and results in a surfaced apology deviation in individuals which allows for easier than normal adherence of insulin, resulting in a quicker cellular response as well as a larger population of cells responding to the insulin. By dividing patients by subtype of diabetes, additional personalization and tuning/tailoring of therapy prompts may be provided.

Figure 22A:
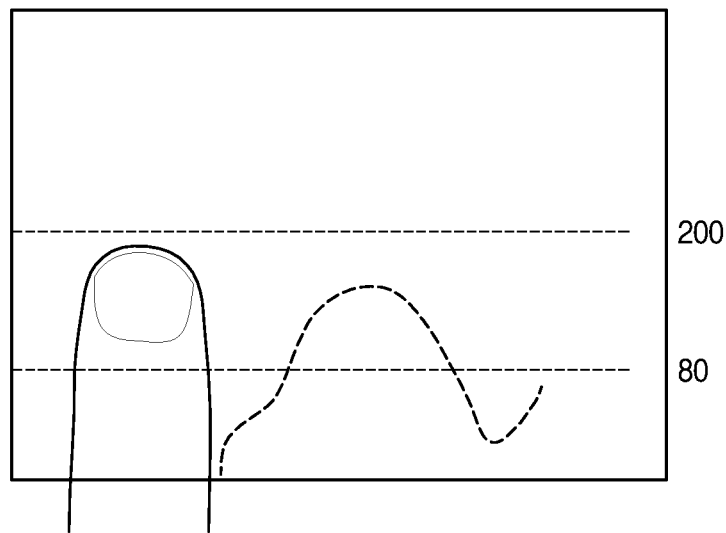
FIGS. 22A and 22B illustrate user input adjusting threshold levels.
Figure 22B:
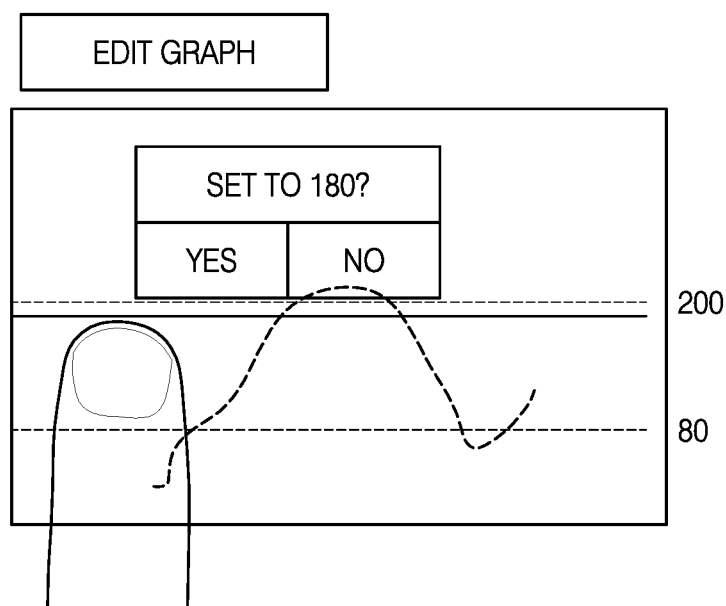

Another type of user-entered input which may be employed in the decision-support application/functionality is user input on alert thresholds so as to reduce alert batik. User-entered thresholds may reduce the number of clicks necessary for the user to set up alerts. In this implementation, and referring to FIGS. 22A and 22B, a user can, on the user interface, touch the actual threshold line on the graph and drag it to the alert threshold the user desires. A pop-up value informs the user of the current exact value of the threshold. When the user takes the user's finger off the line, a pop-up will ask the user if the threshold is correct. This functionality mitigates accidental touch and drag. In a variation, the graph could be one allowing the user to follow daily trends and set alerts corresponding to the daily activities of the user.

The above description has included various types of inputs. Other and more examples of inputs, and the use of the same in decision support, are described below with regard to specific examples. Examples are also provided in which variables are tied together to glean other and additional data, e.g., if GPS indicates very rapid movement, it may be inferred that the user is driving and this information used in decision-support. In addition, other examples of determining inputs, and in more detail the use of smart phones to glean lifestyle information, are disclosed in co-pending U.S. patent application Ser. No. 13/801,445, file Mar. 13, 2013, entitled "Systems and Methods for Leveraging Smartphone Features in Continuous Glucose Monitoring", owned by the assignee of the present application and herein incorporated by reference in its entirety.

System Details

Figure 23:
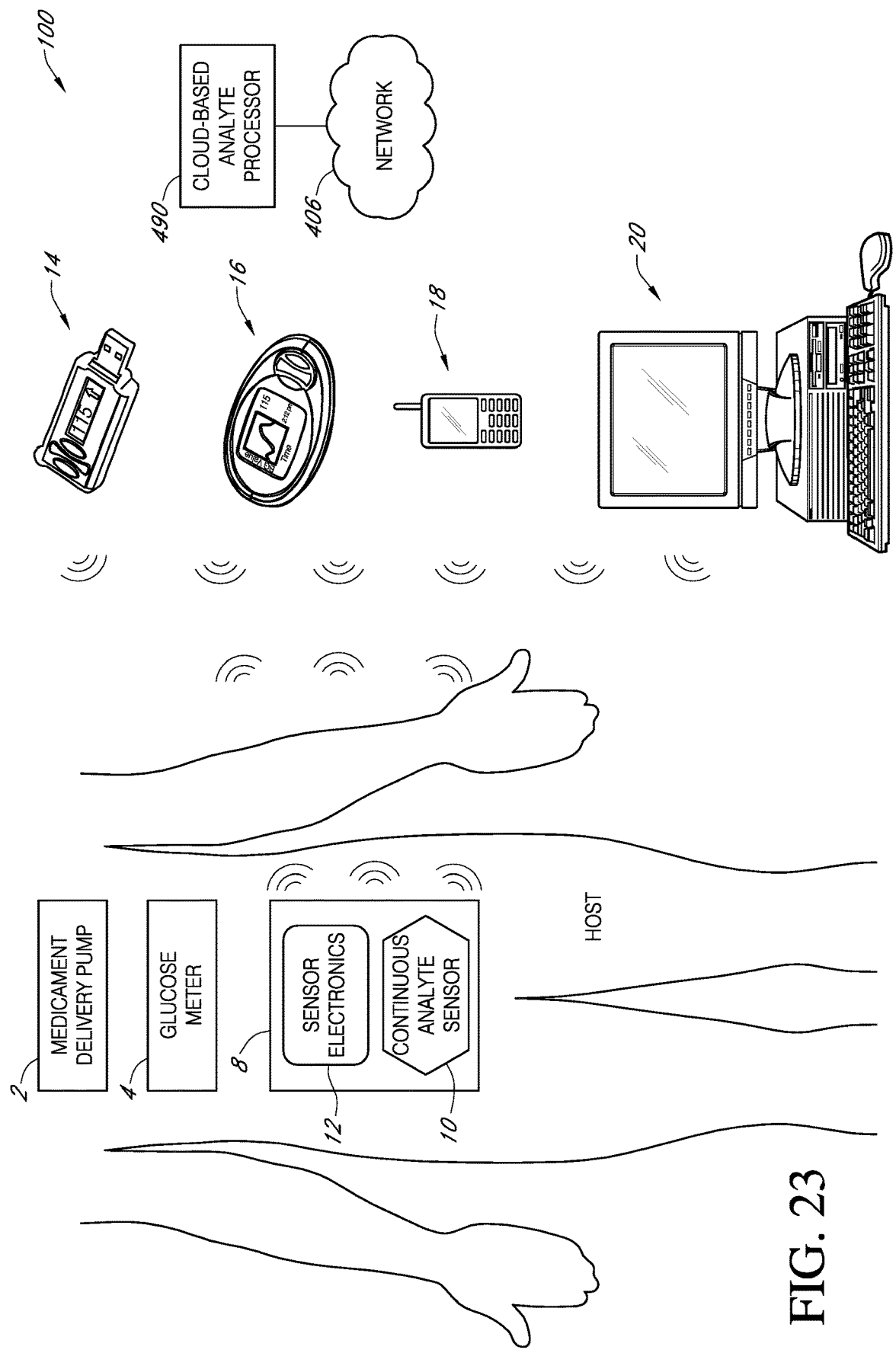
FIG. 23 is an illustration of an example system in which the methods discussed herein may be implemented.

FIG. 23 depicts in further detail elements of the example system 100, in accordance with some example implementations. The system 100 may include a continuous analyte sensor system 8 including sensor electronics 12 and a continuous analyte sensor 10. The system 100 may include other devices and/or sensors, such as medicament delivery pump 2 and glucose meter 4. The continuous analyte sensor 10 may be physically connected to sensor electronics 12 and may be integral with (e.g., non-releasably attached to) or releasably attachable to the continuous analyte sensor 10. The sensor electronics 12, medicament delivery pump 2, and/or glucose meter 4 may couple with one or more devices, such as display devices 14, 16, 18, and/or 20.

In some example implementations, the system 100 may include a cloud-based analyte processor 490 configured to analyze analyte data (and/or other patient-related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. A full discussion of using a cloud-based analyte processing system may be found in U.S. Patent Publication No. US-2013-0325352-A1, entitled "Cloud-Based Processing of Analyte Data" and filed on Mar. 7, 2013, herein incorporated by reference in its entirety. In some implementations, one or more steps of the factory calibration algorithm can be performed in the cloud.

In some example implementations, the sensor electronics 12 may include electronic circuitry associated with measuring and processing data generated by the continuous analyte sensor 10. The generated continuous analyte sensor data may also include algorithms, which can be used to process and calibrate the continuous analyte sensor data, although these algorithms may be provided in other ways as well. The sensor electronics 12 may include hardware, firmware, software, or a combination thereof, to provide measurement of levels of the analyte via a continuous analyte sensor, such as a continuous glucose sensor. An example implementation of the sensor electronics 12 is described further below with respect to FIG. 24.

In one implementation, the factory calibration algorithms described herein may be performed by the sensor electronics.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small, key fob-like display device 14, a relatively large, hand-held display device 16, a cellular phone 18 (e.g., a smart phone, a tablet, and the like), a computer 20, and/or any other user equipment configured to at least present information (e.g., medicament delivery information, discrete self-monitoring glucose readings, heart rate monitor, caloric intake monitor, and the like).

In one implementation, the factory calibration algorithms described herein may be performed at least in part by the display devices.

In some example implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information, such as a numerical value, and an arrow, or a color code.

In some example implementations, the relatively large, hand-held display device 16 may comprise a hand-held receiver device, a palm-top computer, and/or the like. This large display device may include a relatively larger display (e.g., larger than the small display device 14) and may be configured to display information, such as a graphical representation of the continuous sensor data including current and historic sensor data output by sensor system 8.

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include a continuous analyte sensor 10 comprising a glucose sensor, the continuous analyte sensor 10 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Figure 24:
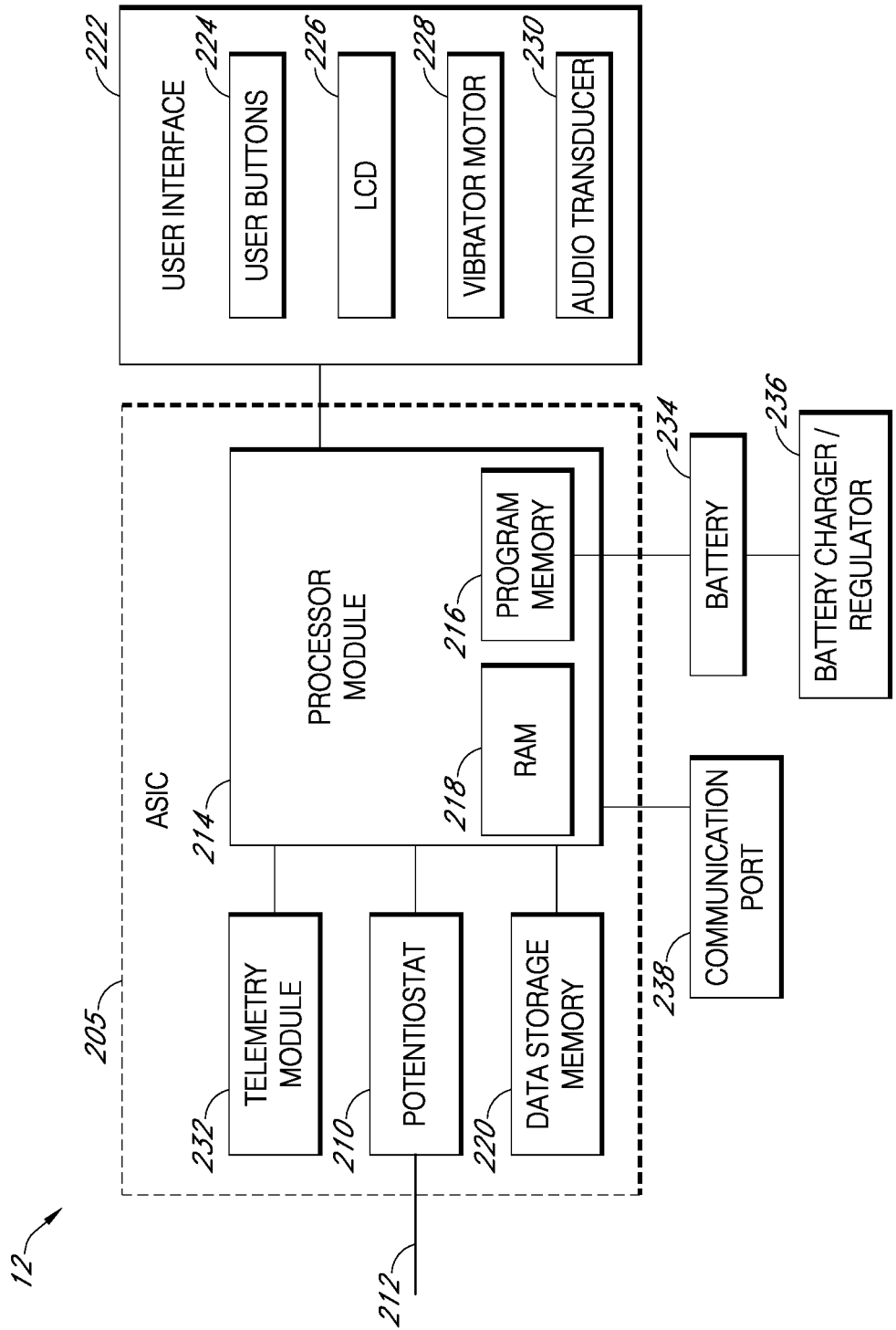
FIG. 24 is a block diagram of an example machine upon which any one or more of the techniques (e.g., methodologies) discussed herein may perform.

FIG. 24 depicts an example of sensor electronics 12, in accordance with some example implementations. The sensor electronics 12 may include sensor electronics that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by calibration algorithms, smoothing and/or filtering algorithms of sensor data, and/or the like.

In some embodiments, a processor module 214 is configured to achieve a substantial portion, if not all, of the data processing, including data processing pertaining to factory calibration. Processor module 214 may be integral to sensor electronics 12 and/or may be located remotely, such as in one or more of devices 14, 16, 18, and/or 20 and/or cloud 490. In some embodiments, processor module 214 may comprise a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronics 12 or other associated devices (e.g., 14, 16, 18, 20 and/or 490). For example, in some embodiments, processor module 214 may be located at least partially within a cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a calibration.

In some example implementations, the sensor electronics 12 may comprise an application-specific integrated circuit (ASIC) 205 coupled to a user interface 222. The ASIC 205 may further include a potentiostat 210, a telemetry module 232 for transmitting data from the sensor electronics 12 to one or more devices, such as devices 14, 16, 18, and/or 20, and/or other components for signal processing and data storage (e.g., processor module 214 and data storage memory 220). Although FIG. 24 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 24, through a first input port 211 of communication port 238 for sensor data the potentiostat 210 is coupled to a continuous analyte sensor 10, such as a glucose sensor to generate sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth® wireless communications technology, Bluetooth® Low-Energy wireless communications technology, ANT™ wireless communications technology, ANT+® wireless communications technology, ZigBee® wireless communications technology, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth wireless communications technology chip, although Bluetooth® technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (IIR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as a time stamp, displayable sensor information, transformed sensor data, an identifier code for the sensor and/or sensor electronics 12, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like).

Although audio and vibratory alarms are described with respect to FIG. 24, other alarming mechanisms may be used as well. For example, in some example implementations, a tactile alarm is provided including a poking mechanism configured to "poke" or physically contact the patient in response to one or more alarm conditions.

The battery 234 may be operatively connected to the processor module 214 (and possibly other components of the sensor electronics 12) and provide the necessary power for the sensor electronics 12. In some example implementations, the battery is a Lithium Manganese Dioxide battery; however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices; for example, a PC communication (com) port can be provided to enable communication with systems that are separate from, or integral with, the sensor electronics 12. The communication port, for example, may comprise a serial (e.g., universal serial bus or "USB") communication port, and allow for communicating with another computer system (e.g., PC, personal digital assistant or "PDA," server, or the like). In some example implementations, the sensor electronics 12 is able to transmit historical data to a PC or other computing device for retrospective analysis by a patient and/or HCP. As another example of data transmission, factory information may also be sent to the algorithm from the sensor or from a cloud data source.

The one or more communication ports 238 may further include a second input port in which calibration data may be received, and an output port which may be employed to transmit calibrated data, or data to be calibrated, to a receiver or mobile device. FIG. 24 illustrates these aspects schematically. It will be understood that the ports may be separated physically, but in alternative implementations a single communication port may provide the functions of both the second input port and the output port.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) may 31 be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 24, a variety of configurations may be used as well. For example, one or more memories may be used to provide storage space to support data processing and storage requirements at sensor electronics 12.

In a preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, U.S. Patent Publication No. US-2008-0119703-A1 (now abandoned), U.S. Patent Publication No. US-2008-0108942 A1 (now abandoned) and U.S. Pat. No. 7,828,728. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

Figure 28:
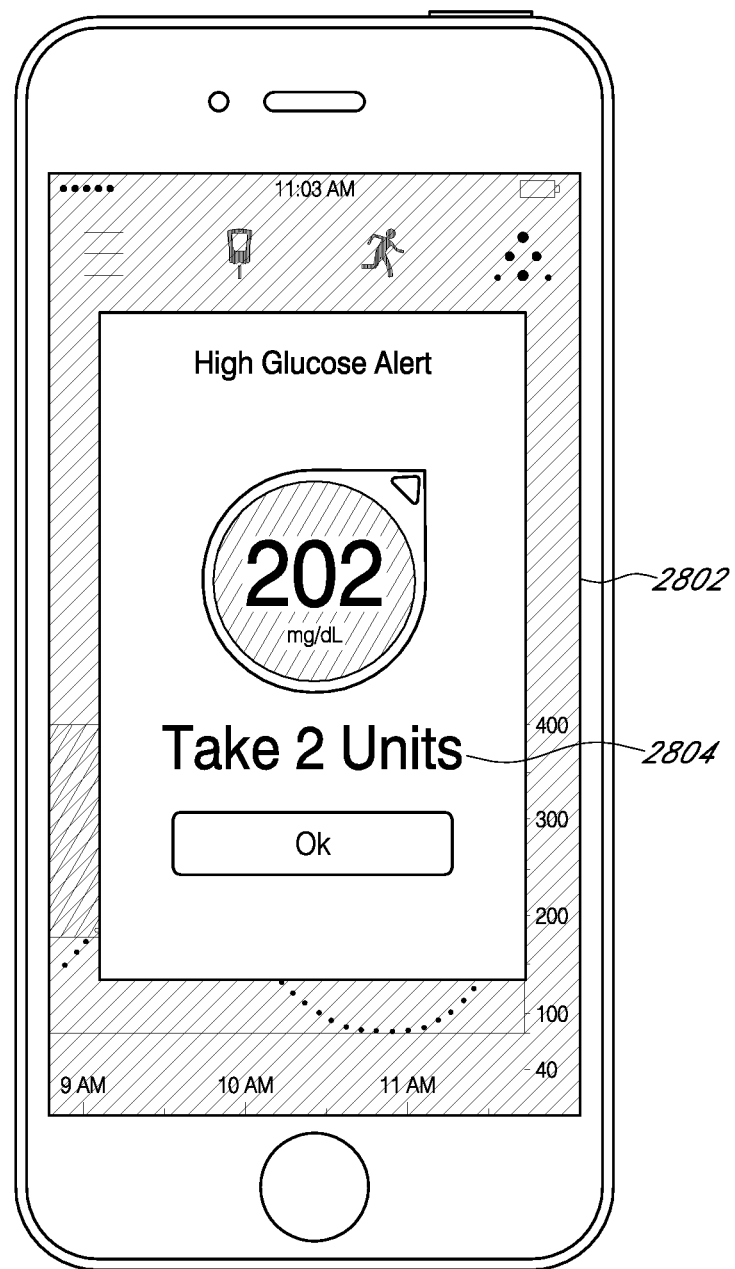
FIGS. 28-30 are illustrations of example guidance delivered on a user interface of a mobile device.

FIG. 28 is an illustration of an example user interface 2802 that includes guidance 2804 to take two units of insulin to correct a hypoglycemic excursion.

Figure 29:
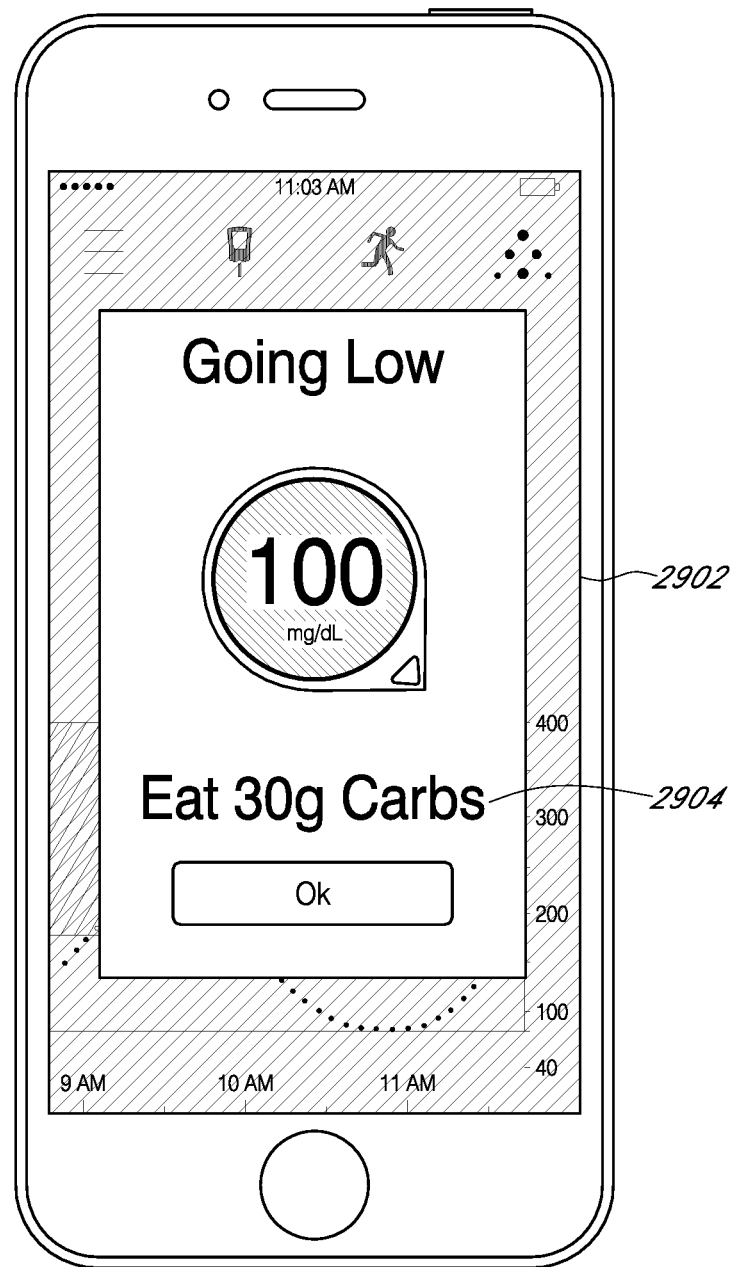
Figure 30:
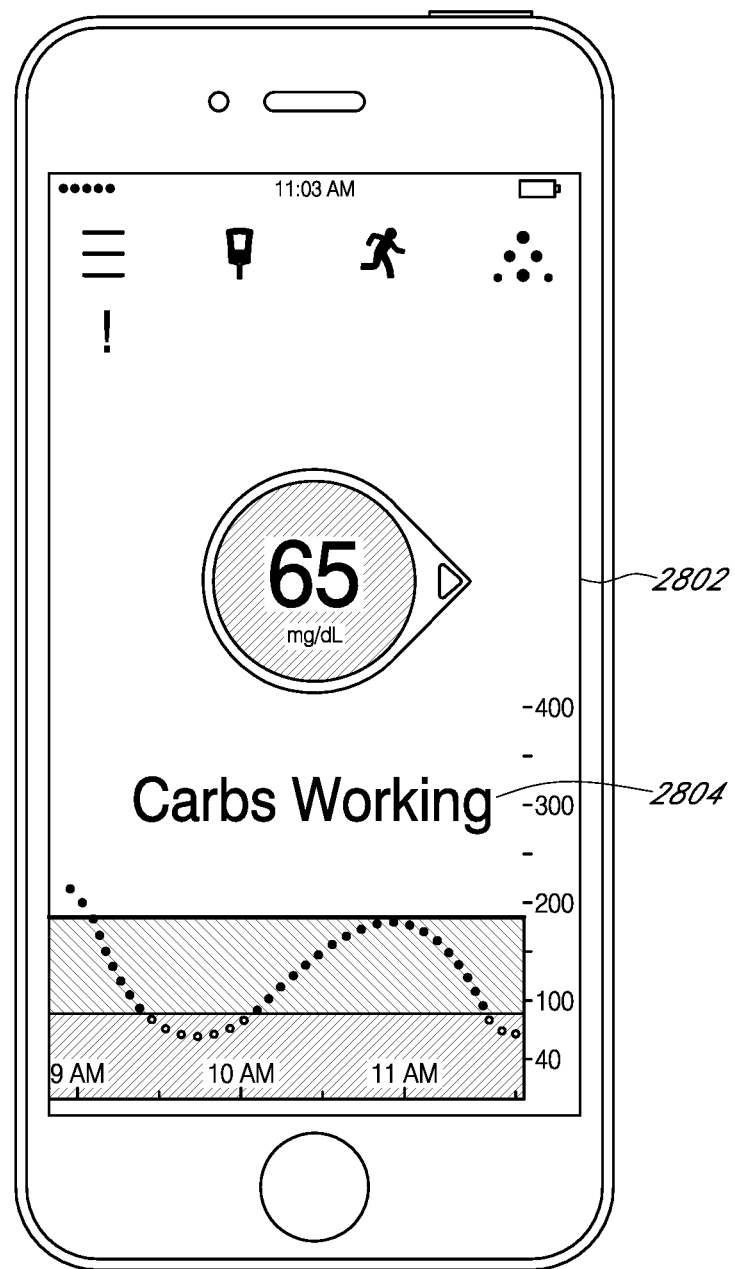

FIG. 29 is an illustration of an example user interface 2902 that includes guidance 2904 to eat some carbohydrates FIG. 30 is an illustration of an example user interface showing a notification that ingested carbohydrates are working, which may for example be determined from a shift in a trend in a glucose concentration level.

Figure 31A:
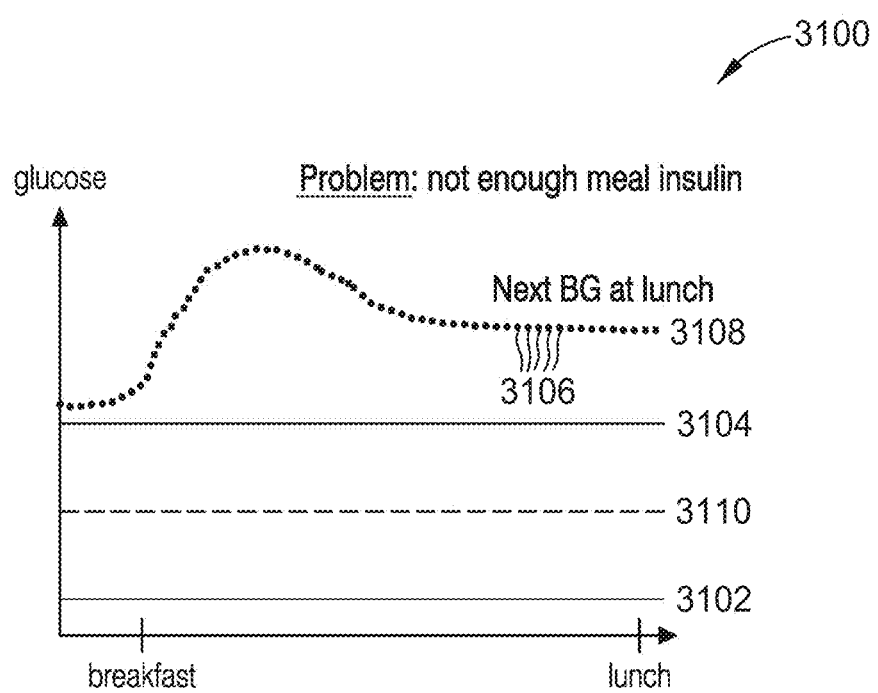
FIGS. 31A and 31B are illustrations of example glucose post-meal trends without (FIG. 31A) and with (FIG. 31B) timely decision-support guidance.
Figure 32A:
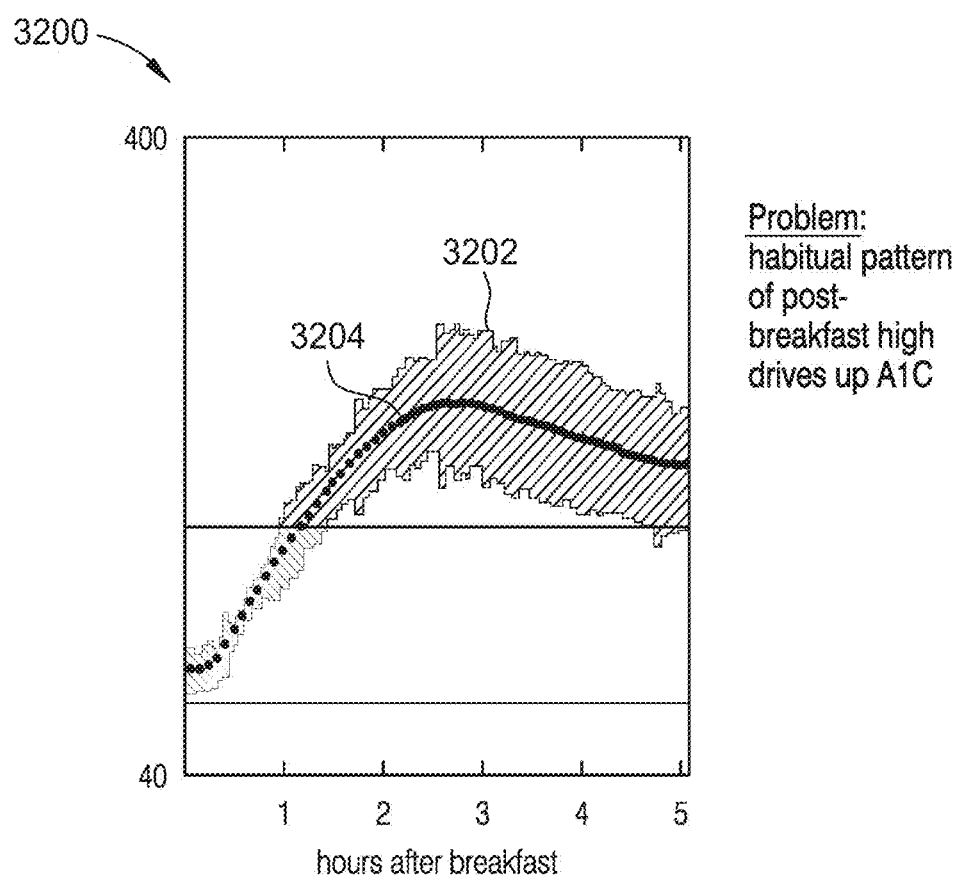
FIGS. 32A and 32B are illustrations of example post-meal insulin trend distribution patterns without (FIG. 32A) and with (FIG. 32B) decision-support guidance.

FIG. 31A is an illustration of a glucose excursion after a breakfast meal. The example graph 3100 on FIG. 31A may be presented on a user interface of a mobile device, tablet, or other computing device. The graph may include estimated glucose level (e.g., in mg/dL) on the y-axis and time (e.g. hours or other time divisions such as schedule breakfast/lunch/dinner) on the x-axis. The graph 3100 may include a low glucose threshold 3102, a high glucose threshold 3104, and a plurality of estimated glucose levels 3106 received from a glucose sensor, such as a continuous glucose monitor, that form a trend line 3108. The graph may also include a target 3110, which may for example be a midline between the high threshold 3104 and low threshold 3102. It can be seen in FIG. 31A that the trend line 3108 defined by the continuous glucose levels 3106 has moved above the high glucose threshold 3104, which may for example be a result of insufficient insulin bolus at a breakfast meal. FIG. 32A is an illustration of multiple trend lines (from multiple days) on a graph 3200 to show a distribution of trends 3202 and an average 3204. The example graph 3200 on FIG. 32A may be presented on a user interface of a device. A pattern of high glycemic excursions over a number of days (or weeks or months) can drive up the patient's A1C level. An A1C test is a blood test, the result of which reflects the average blood sugar level for a time period (e.g., two to three months). The A1C test actually measures the percentage of hemoglobin (a protein in red blood cells) that is glycated (coated with sugar).

Figure 31B:
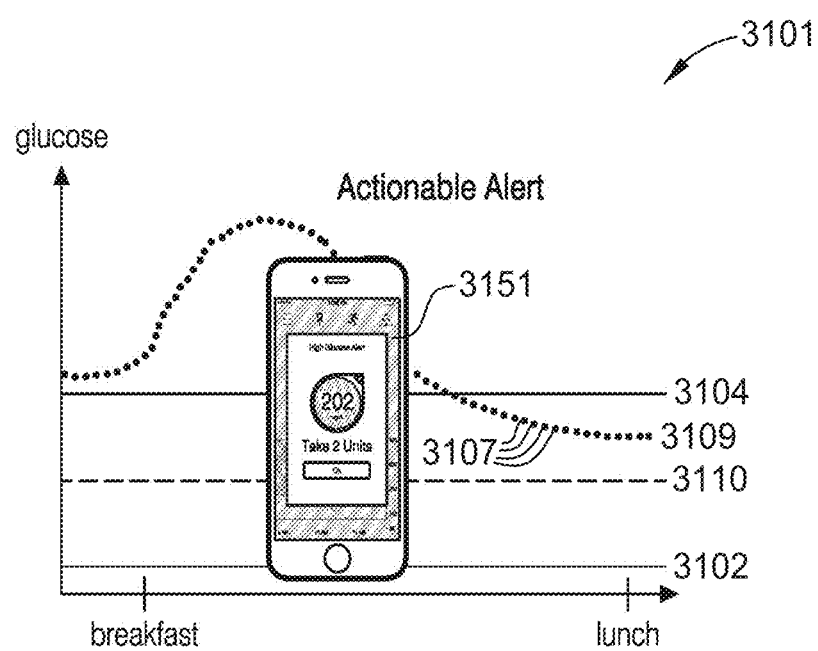
Figure 32B:
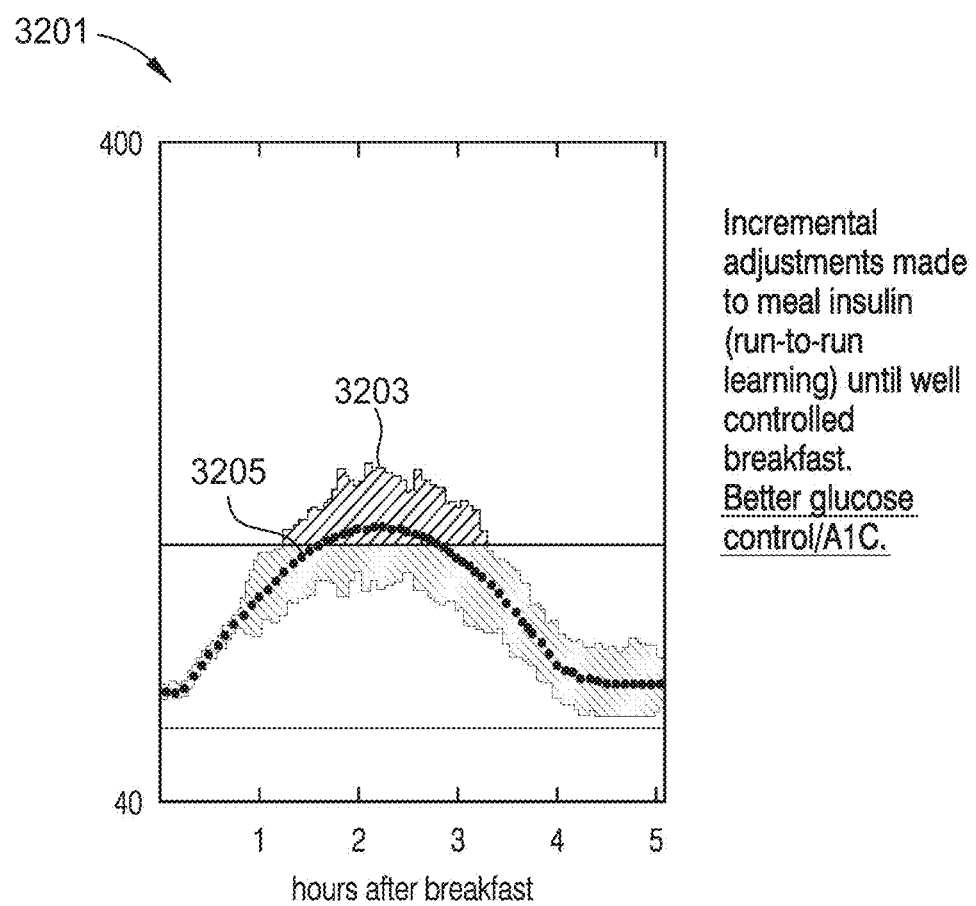

FIG. 31B is an illustration of a glucose excursion after a breakfast meal. The example graph 3101 of FIG. 31B may be presented on a user interface 3151 of a mobile device, tablet, or other computing device. The graph 3101 may include the low glucose threshold 3102, a high glucose threshold 3104, and target 3110 shown in FIG. 31A. It can be seen in FIG. 31B that the trend line 3109 defined by the continuous glucose levels 3107 moved above the high glucose threshold 3104, but timely delivery of a correction dose of insulin (e.g., when the estimated blood glucose concentration level hit 202 mg/dL as indicated by the example guidance) brought a later portion of the trend line back below the high threshold 3104. FIG. 32B is an illustration of multiple trend lines (from multiple days) on a graph 3201 to show a distribution of trends 3203 and an average 3205. By comparing the graph shown on the user interface in FIG. 32B with the graph shown in the user interface in FIG. 32A that the blood glucose is controlled (e.g., within a range defined by the high threshold 3104 and low threshold 3102) a larger amount of time, which results in a lower (better) A1C test result and correlates with better outcomes for the patient.

Figure 33:
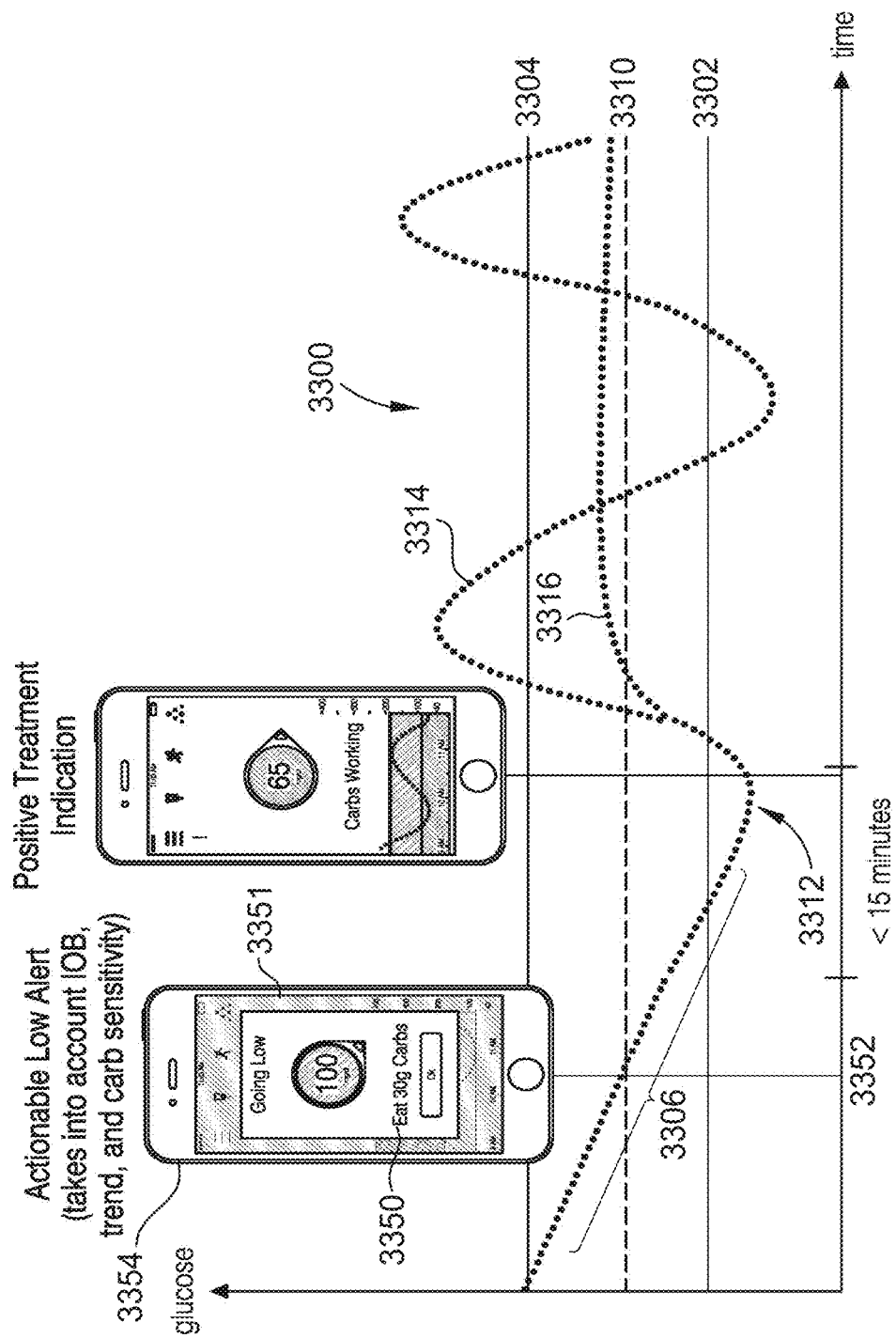
FIG. 33 is an illustration of example glucose trends involving intervention to address a hypoglycemic event.

FIG. 33 is an illustration of example glucose trends involving intervention to address a hypoglycemic event. The graph 3300 may be shown on a user interface 3301. The comments (e.g., Actionable Low Alert, Positive Treatment Indication) are provided for the purpose of illustration and explanation and may optionally be omitted from or included in the user interface. The user interface 3301 may show a low glucose concentration threshold (e.g., 70 mg/dL) 3302, a high glucose concentration threshold (e.g., 200 mg/dL) 3304, and a target 3310 graphed against a timeline (e.g., on the x-axis.) A first trend portion 3306 shows a trend that progresses into a hypoglycemic event 3312 where blood glucose is below the low threshold 3302. After the first trend portion, 3306, two trend scenarios 3114, 31163314, 3316 are illustrated with diverging trend lines. In a first scenario is evident from an unstable trend 3314, the patient consumes carbohydrates to treat the hypoglycemic event, which resolves the low, but the glucose trend "rebounds" into a hyperglycemic excursion 3118, which can be caused by excessive consumption of fast carbohydrates, or a Somogyi effect caused by release of glycogen by the body to treat the low. Continuing with the first scenario trend 3314, the hyperglycemic excursion 3118 is treated with insulin (guidance could optionally be shown in the UI, but is not shown in FIG. 33), which leads to another hypoglycemic event 3120, which rebounds into another hyperglycemic event.

A second scenario is represented by a more stable trend 3316. In an example, a decision support system calculates (or determines from a model) that a projected low glucose level is imminent. The system calculates guidance 3350 and a time 3352 to deliver the guidance. The guidance 3350 may, for example, include an instruction to eat an amount (e.g., 30 grams) of carbohydrates (as illustrated on the user interface 3351 of the device 3354 shown in FIG. 33). The determination (e.g., calculation) of guidance may for example take into account the amount of insulin on board (IOB), the trend (e.g. rate of change of blood glucose or $2^{nd}$ or $3^{rd}$ derivatives of blood glucose), the insulin sensitivity of the patient, or the carbohydrate sensitivity of the patient, all of which may be calculated by the system, determined from a model, or received from a user. In some examples, the guidance may specify a time or time window (not shown) to consume carbohydrates (e.g., "in the next 5 minutes"), and the guidance may also specify or differentiate (not shown) slow (e.g., complex starches or a blend of carbohydrates and fats/proteins), fast carbohydrates (e.g. glucose tablets or maple syrup or other high-sugar foods), or other foods. In some examples, a hypoglycemic event may be avoided by the timely consumption of carbohydrates. In the illustrated example, the hypoglycemic event still occurs, but carbohydrates already on board (due to the timely delivery of guidance) enter the bloodstream and resolve the hypoglycemic event. Additional guidance ("Carbs Working") guidance may be delivered during the hypoglycemic event to assure the patient that no further action (e.g., consumption of additional carbohydrates) is necessary. As shown in FIG. 33, the timely delivery of guidance, and action thereon, may avoid the rebound and oscillating hypoglycemic events and hyperglycemic excursions.

Figure 34:
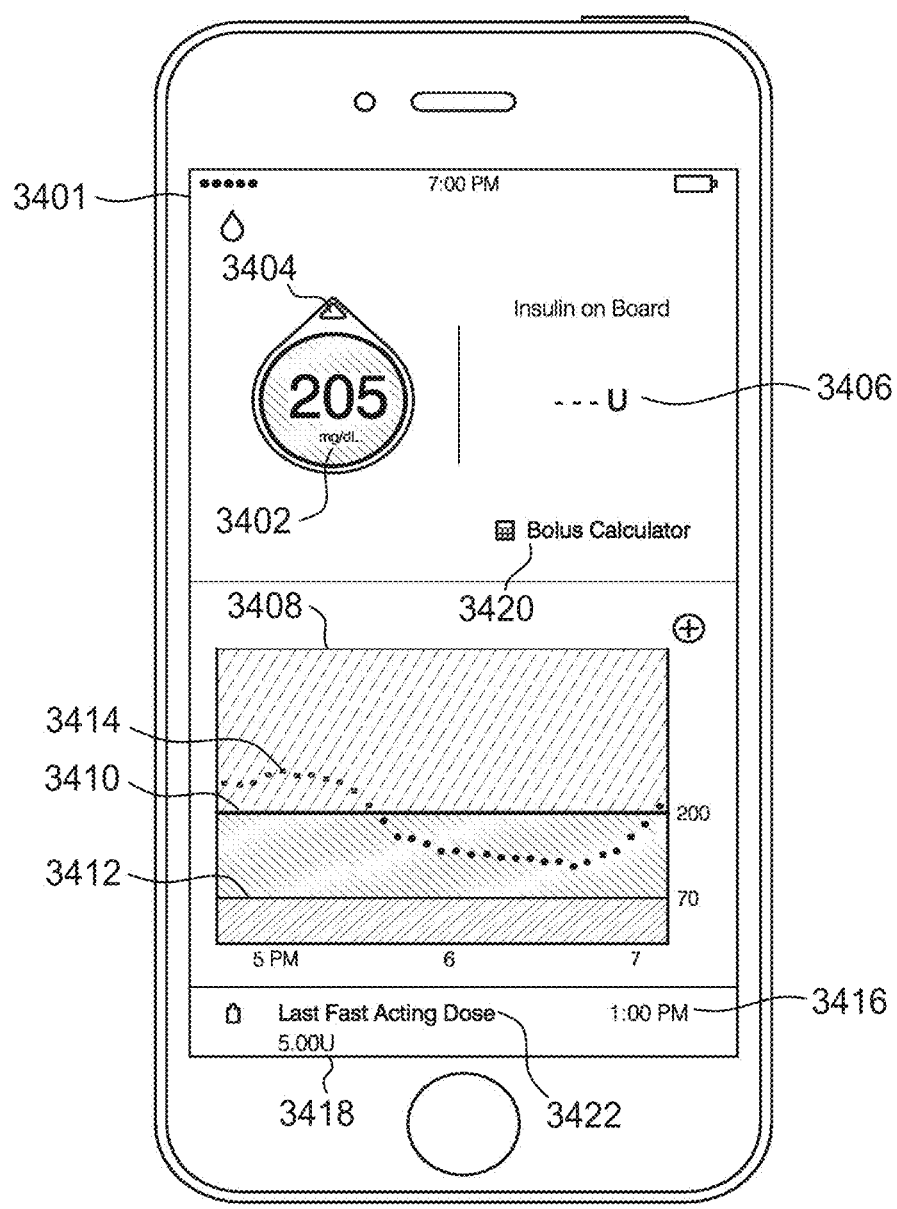
FIGS. 34-37 are illustrations of an example user interface on a device.
Figure 35:
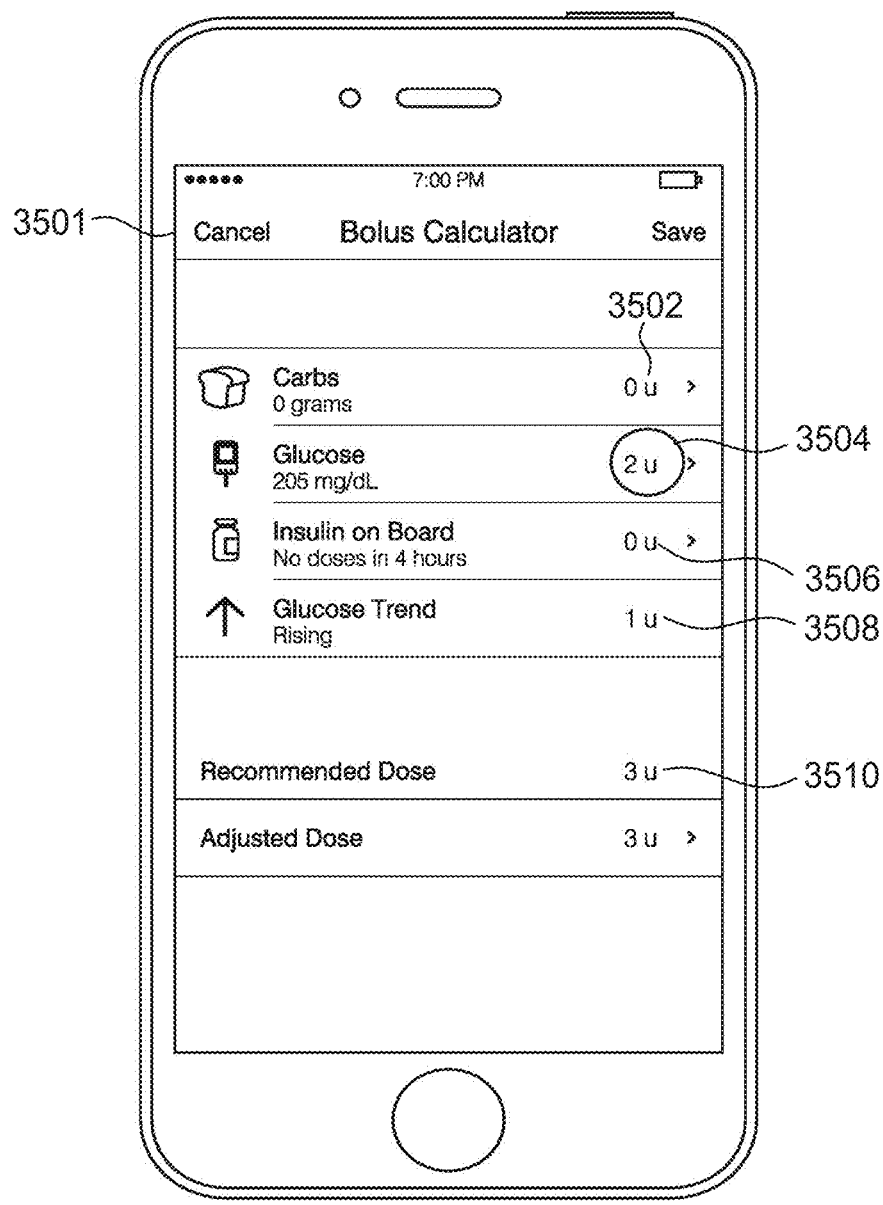
Figure 36:
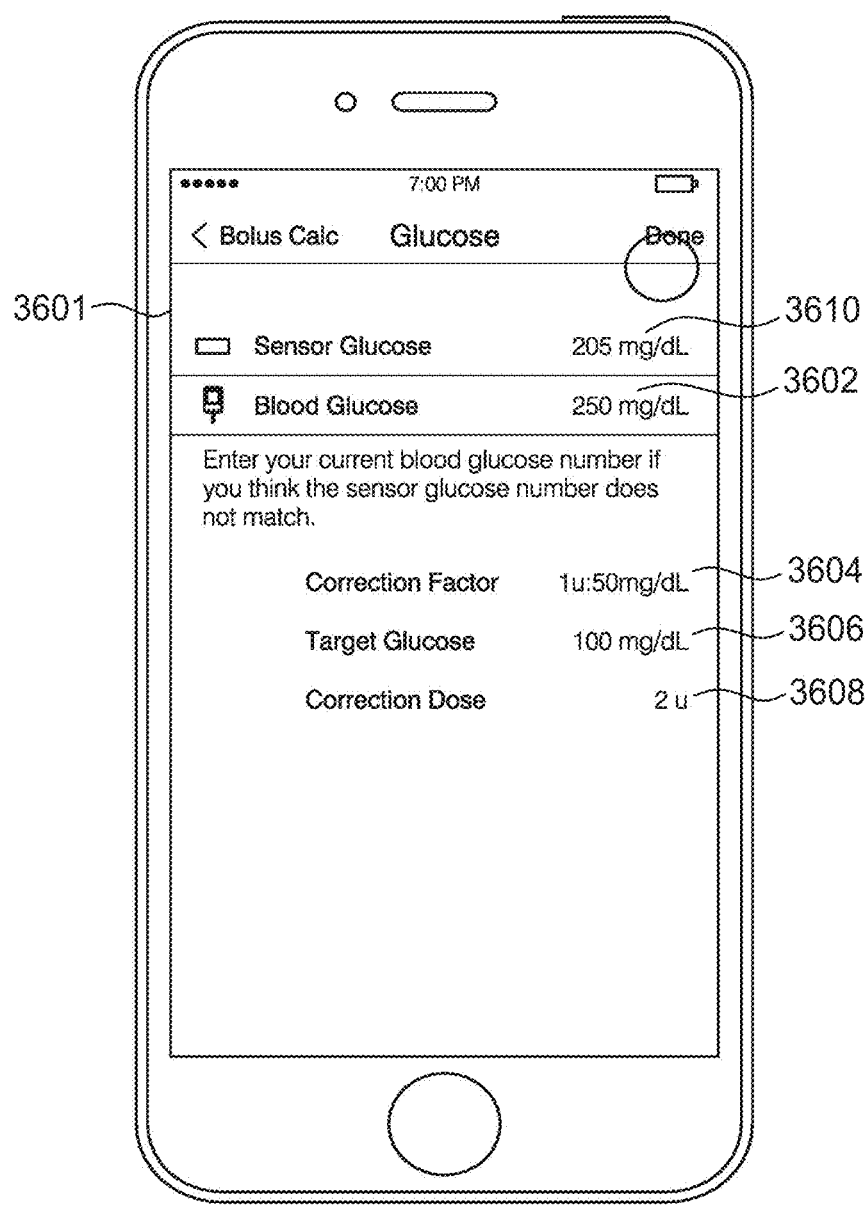
Figure 37:
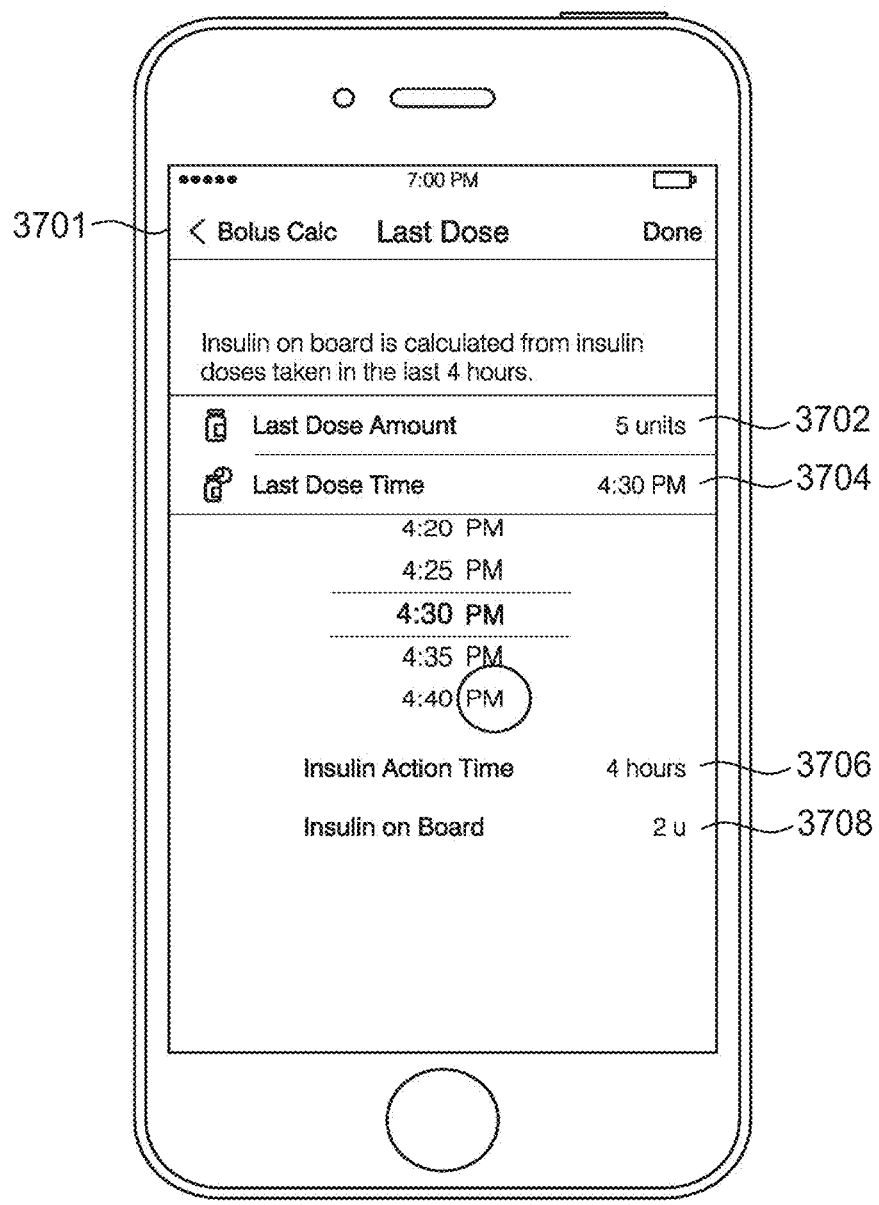

FIGS. 34-37 are illustrations of an example user interface on a device. FIG. 34 shows a user interface 3401 showing fields for an estimated blood glucose value (205 mg/Dl) 3402 and trend (arrow up around the number 205) 3404, insulin on board 3406, a time 3416 and amount 3418 for a last fasting insulin dose, a trend chart 3408 showing a high threshold 3410, a low threshold 3412, and a trend line 3414. Pressing the bolus calculator button 3420 may bring up the bolus calculator screen shown in FIG. 35. The bolus calculator interface 3501 may include an amount of carbohydrates 3502, a glucose concentration level 3504, insulin on board 3506, and a trend 3508. The bolus calculator application may use this information to determine a recommended insulin dose 3510. In an example, the bolus calculator interface 3501 may include an additional field where a percentage (e.g., 70% or 150%) may be entered by a user, and the insulin will be calculated as a percentage of the recommended insulin to allow a user to use the judgment of the user to make adjustments to account for the impact of exercise, illness, stress, or other factors. In some examples, the interface 3501 may also display "Carbs on Board" in addition to insulin on board as a convenience for the user to enable balancing or awareness of both carbohydrates and insulin. Selecting the glucose value in the interface 3501 may bring up a glucose interface 3601 shown in FIG. 36, which may allow a user to enter a glucose value in a blood glucose field 3602 and may allow a user to see, or edit, a correction factor 3604, target glucose concentration level 3606, and correction dose 3608. The interface 3601 may also show a CGM sensor glucose reading 3610, which may be useful for comparison to a blood glucose (e.g., finger stick) reading. Selecting a portion of a last acting dose field 3422 on the user interface 3401 shown in FIG. 34 may bring up a Last Dose interface 3701 which may allow a user to enter values in a last dose amount field 3702 or a last dose time field 3704 and may optionally show or allow a user to edit an insulin action time 3706 or an insulin on board amount 3708.

In some examples, a decision support system for determining guidance and timing of guidance, such as the system 100 or any of the other suitable systems described herein, is configured to modify its operation based on a disease state of the host. For example, when the decision support system is used by a host having Type I diabetes, the decision support system may be configured to respond differently when the host's disease state indicates that the host is in a "honeymoon" period during which the host's pancreas still generates some insulin than at a more advanced disease stage in which the host's pancreas makes less or sometimes no insulin.

In another example, the decision support system can be configured to base the guidance, timing of guidance, and other factors on the stages of Type II diabetes. Type II diabetes has distinct stages during which the decision support needs of the host are different. Different stages of Type II diabetes can be characterized by different courses of treatment, such as a prediabetic stage, an oral medication stage, an oral medication and basal insulin stage, a multiple daily injection (MDI) stage, etc.

When the host's disease state indicates these different stages, the decision support needs of the host may be different and the decision support system may, accordingly, behave differently. For example, when the host is in the prediabetic stage, the host's ability to process insulin may be impaired; however, the host may be able to obtain acceptable blood glucose concentration outcomes with a course of treatment involving management of diet and exercise. Accordingly, when the host's disease state indicates a prediabetic stage, the decision support system may be configured to emphasize functions related to meal memory and management as well as exercise and physical activity. For example, the decision support system may be configured to provide guidance as described herein related to the nutritional content (e.g., carbohydrate count) of the user's meals. The decision support system may also be configured to provide guidance related to exercise such as; for example, guidance that advises the host to make a dietary or exercise change as described herein.

When the host's disease stage indicates an oral medication stage, the focus of the decision support system may shift to emphasize compliance with the host's medication treatment. For example, the decision support system may provide guidance and/or insights reminding the host to take his or her medication. The guidance and/or insights, in some examples, provide the host with a description of the benefits of taking the medication, for example, to motivate the user to take the medication on schedule. In some examples, the decision support system configures the timing of guidance or insights to correspond to the time when the host is scheduled to receive an oral medication. In this way guidance or insights can include a reminder for the host to take his or her oral medication at the time that the medication should be taken. In some examples described herein, the messaging frequency (e.g., frequency of guidance and/or insight) is modified based on factors such as the host or other user's engagement stage. When the frequency of guidance and/or insights is limited, the decision support system may prioritize guidance and/or insights based on the disease stage. For example, in an oral medication stage, the decision support system may provide the host with guidance and/or insights related to diet and exercise but may adjust the priority of guidance and/or insights to include insights related to medication compliance, for example, at the time that medication is to be taken.

When the host's disease stage indicates insulin usage, such as basal or MDI treatments, the decision support system may configure guidance, insight, and/or the timing to emphasis titration of basal or bolus insulin doses. For example, the decision support system may increase the messaging frequency of messages or guidance related to detecting and displaying blood glucose patterns. If the host is receiving MDI treatments, the decision support system may provide guidance and/or insight related to bolus calculation and meal planning, for example, as described herein.

Figure 39:
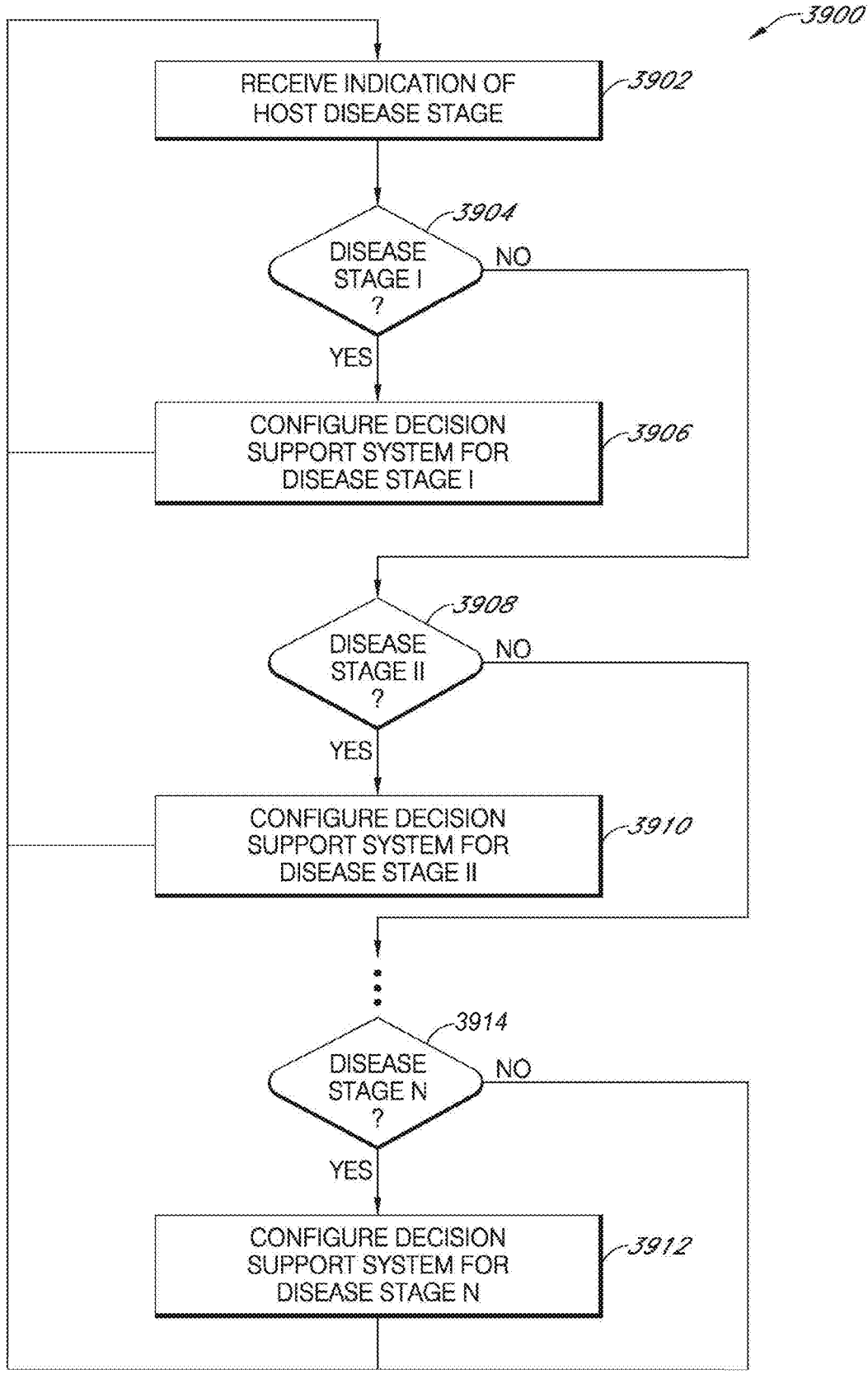
FIG. 39 is a flowchart showing one example of a process flow that can be executed by a decision support system to change in response to changes in the disease stage of the host.

In some examples, a decision support system can modify the insight, guidance, and/or the timing thereof as the disease stage of a host changes. FIG. 39 is a flowchart showing one example of a process flow 3900 that can be executed by a decision support system to change in response to changes in the disease stage of the host. At step 3902, the decision support system receives an indication of a host disease state. This can occur in one or more of a number of different ways. In some examples, a user device 256 (FIG. 17), display device 14-20 (FIG. 23) or other suitable device provides a user interface including a set-up wizard feature. When executed, the set-up wizard may prompt the host or other user via a user interface to provide data regarding the host's disease state, which may be related to Type II diabetes or another condition. For example, the host or other user may indicate treatments that the host is receiving (e.g., diet and exercise, oral medications, basal insulin plus oral medication, basal insulin plus MDI, etc.).

In some examples, the decision support system considers various other inputs describing the host to determine the hosts disease state. Referring again to FIG. 2B, the physiology model 112 may be used to generate a disease state for the host using, for example, the inputs shown in FIG. 2B.

At step 3904, the decision support system determines if the host disease state indicates a first disease stage, such as a prediabetic stage or other stage for Type II diabetes, as described herein. If yes, then the decision support system is configured for the first disease stage at step 3906, for example, as described herein. If first disease stage is not indicated, the decision support system determines at step 3908 whether a second disease stage is indicated. If yes, then the decision support system is configured for the second disease stage at step 3910, for example, as described herein. The process flow 3900 may continue for a number of disease stages (indicated as "N" in FIG. 36). For example, the decision support system determines at step 3914 whether an Nth disease stage is indicated. If yes, then the decision support system is configured for the Nth disease stage at step 3912. After configuring the decision support for an indicated disease stage at steps 3906, 3910, 3912, etc., the decision support system may operate in the generated configuration and may await a next indication of the host's disease stage at operation 3902.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system comprising:
   a glucose concentration sensor configured to detect a glucose concentration level of a host;
   a communication circuit configured to receive the glucose concentration level from the glucose concentration sensor; and
   a processor configured to:
      receive a real-time datum indicative of the glucose concentration level;

determine a temporal pattern of behavior of the host, an engagement state of the host with decision support guidance, a risk tolerance of the host, and an unavailability of the host to receive a guidance message, wherein:
  the temporal pattern of behavior corresponds to a learned pattern of behavior of the host correlated to time;
  the engagement state is determined based on a consistency and response time of the host responding to prior guidance messages as correlated to time;
  the risk tolerance corresponds to at least one of:
    a comfort of the host based on experience of the host with intervention; or
    an availability of caregivers for intervention; and
  the unavailability of the host is due to one or more of: a location of the host, a calendar event scheduled for the host, and the host being in a car;
predict, based on the temporal pattern and the engagement state, a time period during which the host will be unavailable to receive the guidance message;
predict, based on the real-time datum, that the glucose concentration level of the host will not be within a first range during the time period during which the host will be unavailable;
determine, based on the real-time datum, a risk level associated with the glucose concentration level of the host not being within the first range during the time period;
determine a content of the guidance message based at least in part on the real-time datum, the temporal pattern, and the engagement state, wherein the content of the guidance message is related to an action to be performed prior to the time period; and
provide the guidance message to the host prior to the time period, wherein providing the guidance message to the host is based on a function of the risk tolerance of the host, the risk level associated with the glucose concentration level of the host not being within the first range during the time period, and the unavailability of the host.

2. The system of claim 1, further comprising a memory circuit configured to store a physiologic model, wherein the processor is further configured to determine a physiologic state of the host using the physiologic model and the real-time datum, and wherein the processor is configured to predict that the glucose concentration level of the host will not be within the first range further based on the physiologic state.

3. The system of claim 2, wherein the content of the guidance message is further based at least in part on the physiologic state.

4. The system of claim 2, wherein in determining the physiologic state, the processor is configured to determine an insulin state, an energy absorption state, or an energy expenditure state.

5. The system of claim 1, further comprising a mobile device including a memory circuit, the processor, and a user interface configured to display the guidance message, wherein the mobile device is configured to receive user input through the user interface, and wherein the processor is configured to predict that the glucose concentration level of the host will not be within the first range further based on the user input.

6. The system of claim 1, wherein the system includes a mobile device, the mobile device including a memory circuit and the processor, and wherein the mobile device includes a user interface configured to provide the guidance message, the system further comprising an insulin delivery system.

7. The system of claim 1, wherein the processor is further configured to predict the time period based at least in part on an upcoming event in a calendar.

8. The system of claim 7, wherein the processor is configured to predict that the glucose concentration level of the host will not be within the first range further based at least in part on a projected change in insulin sensitivity calculated based at least in part on the upcoming event in the calendar.

9. The system of claim 7, wherein the processor is further configured to automatically receive event data about the upcoming event whenever the upcoming event is newly input by the host, and wherein the processor is configured to predict the time period based on the received event data.

10. The system of claim 1, further comprising a memory configured to store a physiologic model, wherein the processor is configured to predict that the glucose concentration level of the host will not be within the first range further based at least in part on the physiologic model indicating that a transition to an undesirable physiologic state is likely to occur.

11. The system of claim 10, the processor is further configured to determine an intervention to avoid the transition to the undesirable physiologic state; and wherein the content of the guidance message indicates the intervention.

12. The system of claim 1, wherein the processor is further configured to determine a delivery time before the time period for delivery of the guidance message using the temporal pattern.

13. The system of claim 12, wherein the processor is configured to select the delivery time when the host is likely to be available based at least in part on the temporal pattern.

14. The system of claim 1, wherein the action is configured to promote glucose concentration stability during the time period.

15. The system of claim 1, wherein the processor is further configured to:
  determine a messaging frequency based at least in part on the engagement state; and
  determine a time before the time period for delivering the guidance message based at least in part on the messaging frequency.

16. The system of claim 15, wherein the processor is further configured to:
  determine that the engagement state has changed to a changed engagement state;
  determine a new messaging frequency based at least in part on the changed engagement state; and
  determine a second time for delivering a second guidance message based at least in part on the new messaging frequency.

17. The system of claim 1, wherein the time period is predicted further based on a behavioral input.

18. The system of claim 17, wherein the behavioral input comprises patient activity information.

19. The system of claim 1, wherein the processor is further configured to automatically adjust a predicted patient glucose concentration level of the host based on the real-time datum.

20. The system of claim 1, wherein the processor is further configured to:
  predict a second time period during which a caregiver of the host will be unavailable; and
  provide the guidance message to the host or caregiver prior to the second time period.

21. The system of claim 1, wherein the unavailability of the host to receive the guidance message further due to the host being asleep.

22. A method of delivering physiologic glucose concentration management guidance comprising:
- receiving a real-time datum indicative of a glucose concentration level of a host, wherein the glucose concentration level is detected by a glucose concentration sensor;
- determining a temporal pattern of behavior of the host, an engagement state of the host with decision support guidance, a risk tolerance of the host, and an unavailability of the host to receive a guidance message, wherein:
  - the temporal pattern of behavior corresponds to a learned pattern of behavior of the host correlated to time;
  - the engagement state is based on a consistency and response time of the host responding to prior guidance messages as correlated to time;
  - the risk tolerance corresponds to at least one of:
    - a comfort of the host based on experience of the host with intervention; or
    - an availability of caregivers for intervention; and
  - the unavailability of the host is due to one or more of: a location of the host, a calendar event scheduled for the host, and the host being in a car;
- predicting, based on the temporal pattern and the engagement state, a time period during which the host will be unavailable to receive the guidance message;
- predicting, based on the real-time datum, that the glucose concentration level of the host will not be within a first range during the time period during which the host will be unavailable;
- determining, based on the real-time datum, a risk level associated with the glucose concentration level of the host not being within the first range during the time period;
- determining a content of the guidance message based at least in part on the real-time datum, a temporal pattern, and the engagement state, wherein the content of the guidance message is related to an action to be performed prior to the time period; and
- providing the guidance message to the host prior to the time period, wherein providing the guidance message to the host is based on a function of the risk tolerance of the host, the risk level associated with the glucose concentration level of the host not being within the first range during the time period, and the unavailability of the host.

* * * * *